US006403307B1

(12) United States Patent
Stone et al.

(10) Patent No.: US 6,403,307 B1
(45) Date of Patent: Jun. 11, 2002

(54) GLAUCOMA THERAPEUTICS AND DIAGNOSTICS

(75) Inventors: Edwin M. Stone, Iowa City; Val C. Sheffield, Coralville; Wallace L. M. Alward; John Fingert, both of Iowa City, all of IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/056,285

(22) Filed: Apr. 7, 1998

Related U.S. Application Data

(63) Continuation-in-part of application No. 08/822,999, filed on Mar. 21, 1997.

(51) Int. Cl.[7] ............................ C12Q 1/68; C12P 19/34; C07H 21/04
(52) U.S. Cl. ........................ 435/6; 435/91.2; 536/23.1; 536/24.3
(58) Field of Search .................. 435/6, 91.2; 536/24.33

(56) References Cited

U.S. PATENT DOCUMENTS 5,606,043 A 2/1997 Nguyen et al. ............ 536/23.5

FOREIGN PATENT DOCUMENTS

| WO | WO 96/14411 | 5/1996 | ............ C12N/15/12 |
|----|-------------|--------|------------------------|
| WO | WO 96/33287 | 10/1996 | ............ C12Q/1/68 |
| WO | WO 98/20131 | 5/1998 | |
| WO | WO 98/32850 | 7/1998 | |

OTHER PUBLICATIONS

Kubota et al., Genomics, vol. 41, pp. 360–369, 1997.*
Kubota et al., Biochem, Biophys. Res. Comm., vol. 242, pp. 396–400, 1998.*
Levitan et al. Textbook of Human Genetics, 3rd edition, Oxford University press. pp. 32–33, 1988.*
Written opinion dated Oct. 23, 1998.
Database entry HSU85257, Mar. 2, 1997 (Nguyen et al.).
"CHLC Report" (Newsletter), Cooperative Human Linkage Center, 1: 1–18, (May 1993).
"Editorial: Genetic Associations of Glaucoma", *British Journal of Ophthalmology*, 64: 225–226, (1980).
Cotton, P., "Glaucoma Gene Mapped to Chromosome 1", *JAMA*, 269(21): 2715, (Jun. 2, 1993).
Escribano, J., et al., "Isolation and Characterization of Cell–Specific cDNA Clones from a Subtractive Library of the Ocular Ciliary Body of a Single Normal Human Donor: Transcription and Synthesis of Plasma Proteins", *J. Biochem.*, 118: 921–931,(1995).
Francois, J., "Genetics and Primary Open–Angle Glaucoma", *Am. J. Ophthalmol.*, 61: 652–665, (1966).
Harris, D., "The Inheritance of Glaucoma: A Pedigree of Familial Glaucoma", *Am. J. Ophthalmol.*, 60: 91–95, (1965).
Johnson, A.T. et al., "Clinical Features and Linkage Analysis of a Family with Autosomal Dominant Juvenile Glaucoma", *Ophthalmology*, 100 (4): 524–528, (Apr. 1993).
Kolker, A.E., "Glaucoma Family Study: Ten–Year Follow–up (Preliminary Report)", *Israel J. Med. Sci.*, 8(8–9): 1357–1361, (Aug.–Sep. 1972).
Leighton, D.A., "Survey of the First–degree Relatives of Glaucoma Patients", *Trans. Ophthal. Soc. U.K. 96*: 28–32, (1976).

(List continued on next page.)

Primary Examiner—Carla J. Myers
Assistant Examiner—Jehanne Souya
(74) Attorney, Agent, or Firm—Needle & Rosenberg, P.C.

(57) ABSTRACT

Methods and compositions for preventing and treating glaucoma; and glaucoma diagnostics are disclosed.

13 Claims, 11 Drawing Sheets

OTHER PUBLICATIONS

Figure 2:
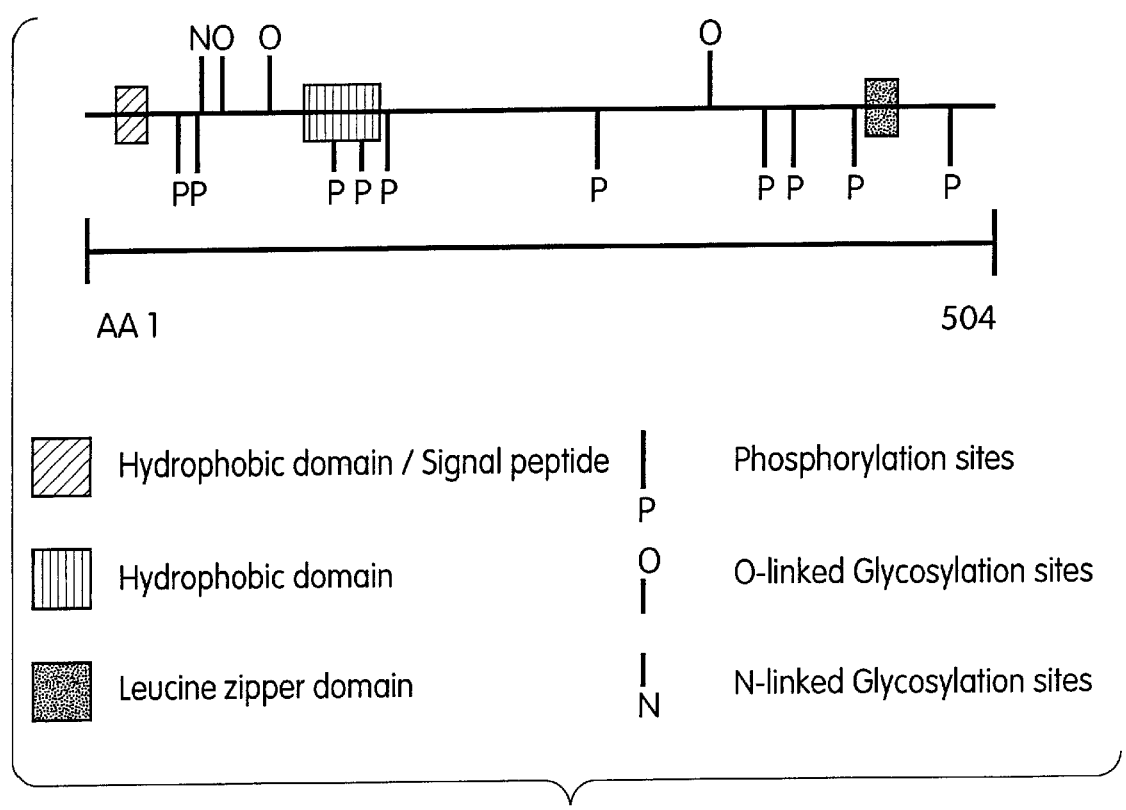

Martin, J.P. and E.C. Zorab, "Familial Glaucoma in Nine Generations of a South Hampshire Family", *Brit. J. Ophthal.*, 536–542, (1974).

Miller, S.J.H. and G.D. Paterson, "Studies on Glaucoma Relatives", *Brit. J. Ophthalmol.*, 46: 513–522, (1962).

Orita, M. et al., "Detection of Polymorphisms of Human DNA by Gel Electrophoresis as Single–Strand Conformation Polymorphisms", *Proc. Natl. Acad. Sci. USA*, 86: 2766–2770, (Apr. 1989).

Ortega, J. et al., "Cloning and Characterization of Subtracted cDNAs from a Human Ciliary Body ibrary Encoding TIGR, a Protein Involved in Juvenile Open Angle Glaucoma with Homology to Myosin and Olfactomedin", *FEBS Letters*, 413: 349–353, (1997).

Perkins, E.S., "Family Studies in Glaucoma", *Brit. J. Ophthal.*, 58: 529–535, (1974).

Ortega, J. et al., "Cloning and Characterization of Subtracted cDNAs from a Human Ciliary Body ibrary Encoding TIGR, a Protein Involved in Juvenile Open Angle Glaucoma with Homology to Myosin and Olfactomedin", *FEBS Letters*, 413: 349–353, (1997).

Sheffield, V.C., et al., "Attachment of a 40–Base–Pair G+C–Rich Sequence (GC–clamp) to Genomic DNA Fragments by the Polymerase Chain Reaction Results in Improved Detection of Single–Base Changes", *Proc. Natl. Acad. Sci. USA*, 86: 232–236, (Jan. 1989).

Sheffield, V.C., et al., "Genetic Linkage of Familial Open Angle Glaucome to Chromosome 1q21–q31", *Nature Genetics*, 4: 47–50, (May 1993).

Stone, E.M. et al., "Identification of a Gene that Causes Primary Open Glaucoma", *Science*, 275: 668–670, (1997).

Sunden, S.L.F. et al., "Fine Mapping of the Autosomal Dominant Juvenile Open Angle Glaucoma (GLCIA) Region and Evaluation of Candidate Genes", *Genome Res.*, 6: 862–869, (1996).

Weatherill, J.R. and Hart, C.T., "Familial Hypoplasia of the Iris Stroma Associated with Glaucoma", *Brit. J. Ophthal.*, 53: 433–438, (1969).

Wallace L.M. Alward, Clinical Features Associated with Mutations in the Chromosome 1 Open–Angle Glaucoma Gene (GLCIA), The New England Journal of Medicine, 1998, 1022–1027.

International Search Report dated Nov. 16, 1999.

* cited by examiner

Fig. 1A-1

Fig. 1A-2

```
huGLC1A  acagagtaagaactgattagaggctaacattgacattgtgcctgagatgcaagactgaaattagaaagttctcccaagatacacagttgttttaaag
moGLC1A  gttatctttcagaggtgggcacacagtttcaccccgtagggtttgggggcacactcatcctaaagcctggtccagagcattggcacagttcctgagac
                 GR                                                              GR huGLC1A  ctaggggtgaggggggaaatctgccgcttctatagaatgctctccctgagccctgatgggtagggtgctgtccttgttctggctgttatttttctct
moGLC1A  aagagctgtggttaggagcttttctgagatgttcacagttcacagttcaggcaacatcatgttctcatccctctgtaggaaccaggagcct
                GR                GR                                                     GR huGLC1A  gtccctgctacgtcttaaaggacttgtttgatctccagttcctagcatagtgcctgcacagtgcaggttctcaatgagtttgcagagtgaatgaaat
moGLC1A  ggaggcattgggctctccttgactctcttgtctctgctacaggacgtgtctactcaggcatgtctgtctccctagttccttatgctgtccagtga
                           GR (CA) repeat polymorphism
huGLC1A  ataaactagaaatatatccttgttgaaatcagcacaccagtagtcctggtgtacgtgtgtgtgtgtgtacgtgtgtgtgtgtaagtgtgtgtgtgtaaaaccag
moGLC1A  aacacaaaatagacttatatccctgttcaaactgcttcctgtcagacaaggtgcgcatatgttcacaagcacacacaaacagacta
                                                                   GR huGLC1A  gtggagatataggaactattattgggtatggtgcataaattgggatgttctttttaaaagaaactccaaacagacttctggaagttatttctaag
moGLC1A  gaaacttaggggttattattgggatgtgggtacatgcacgggactttcaaatgcctccggcactttgttttttaaagact
                                                                     GR huGLC1A  aatcttgctggcagcgtgaaggcaaccccctgtgcacagcccccaccagcctcacgtgcaccctctgtcttcccatgaagggctgctcccagta
moGLC1A  cttgctgcagtgtgagtgtgtaatcctcctatccccccatgctgtccaaccagttcatgtgatcaccctctccctcccccacacagggctgggtccc
                                                                          GR
```

Fig. 1A-3

Fig. 1A-4

```
huGLC1A   CTGGCCAGGAGGAGTTGGAAAAGCAGCAGCCAGGAGGAGTAGCAAGGCTGAGAAGGGGCCAGTGTCCCCAGACCCGAGACACTGCTCGGGCTGTGCCACCAGGCT
          ********** * ************* ********** * *** ** *** ******
moGLC1A   TTGGCCAGGAGGCTAGAAAGCAGCAGCGAGGAGTAACAAGGCTGCGGAGGGGCCAGTGTCCTTCCACCCAGTACCCCTCTCAGGACATGCTGCCAGGCT huGLC1A   CCAGAGAAAGgtaagaatgcagagtgggggactctgagttcagcaggtgatatggctcgtagtgacctgctacagcgcctccaggcctcccctgcctgccc
          ** **
moGLC1A   CCAGGGAAAGgtaagagtgcaggtgagtgtggagtagcaagtttgctggtgaccattacaggaccccagcttctccttctgtt huGLC1A   tttctcctagagactgcacagctagcacagacagatgaattaaggaaagcacagcgatcaccttcaagtattactagtaattagctcctgagagcttc
moGLC1A   ttgtcttttctcagaaactgcaaatccagcagtagtttcattaaggagagcaaagcaaacactttttgcatgcttctagaaagttggctccttgt huGLC1A   atttagattagtggttcagagttcttgtgccctccatgtcagtttccacagtccatagcaaaaggagaataaaagaccgggtgagatgtgtctgcat
moGLC1A   ttaggtcagtgatctggatctgagctcttgtgccccagtcagtcatgacaaaatgatcatgcccacagcagcccaaatgacaaacatgggccaggtggcagtggcagatacatatgat
```

Fig. 1A-5

Exon 2 huGLC1A  caccatgttggccaggctggtctcgaactcctgacctcaggtgatccgctgcctcggcctcccaaagtgctgggattacaggcatgagccaccgcct
moGLC1A  aagctttttaattatgccaatttctcccgattgagaccatcaccctagttcaatgagctaccaacgtggttcagtcatgttacatcttcagataacaa huGLC1A  ggccggcagcctatttaaatgtcatcctcaacatagtcaatcctggccatttttcttacagtaaaatttgtctctcttttaatgcagTTTCTAC
                                                                                               * *** moGLC1A  gtatttgggaacatatcaaacatcaccctccacagagtccgtcttcttgccctttctactacaagtgccaattttttctctcttgaatacagTCTCTCA huGLC1A  GTGGAATTTGGACACTTTGGCCTTCCAGGAACTGAAGTCCGAGCTAACTGAAGTTCCTGCTTCCCGAATTTGAAGGAGAGCCCATCTGGCTATCTCAGG
         ************ **** ************* * ***** ********** * ******** * ******** * ****
moGLC1A  GTGGAATTTGGACACGTTGGCCTTCCAGGAATTGAAGTCAGAGTTAACTGAGTTCCTGCTTCCCAAATCTTGAAGGAAATCCATCTGGCCGACCCAGG huGLC1A  AGTGGAGAGGGAGACACCGgtatgaagttaagtttctccctttgtgccacatgtcttattcatgtctagtgctgttcagagaatcagtataagg
          * ******** *
moGLC1A  AGCAAAGAAGGAGACAAAGgtatgaagttagactctctccctttgagcctactgctctccctctccctctcctctccctctcctctccctctccct huGLC1A  gtaaatgccaccaaggggaaattaactctccctggagcagagagggaggaggaacagagagaactctctctctctctgttccttgtcaga
moGLC1A  ctctcccctctccctctccctctccctctccctccctcctgtgtgtgagtgagtgcatgtagtgttcatatgtgtgtgtgtgtgt huGLC1A  gcaggtctgcaggagtcagcctttcccttacaaagccctctatccaccacttgggaggctgggctgcacagggcaagatgagagatgt
moGLC1A  gtgtgtgtgtgtgtcatgtcgtgccatgtataccttgttcagtagtataccttgttcagtacggaaagagcaactgttcacccagaagagaagacaggtgattcc huGLC1A  gttgattcatccactgattgtcatgtagaattagatatactttgagaagttacatttttcagtagcgcttcatatctt
moGLC1A  ccaaggcagagttgggagaagaagctgaaacctgtctgctgcctttctagacatatgtactgaagcttgga

Fig. 1B

Exon 3 huGLC1A cttacaactgatactgagtgaattgtactttaaatatttatagctcccactccatgatgcccctcagtgatagcaataattgtcaataacatgaaac
moGLC1A ctttgtctatcaaggaaaagagcatttgtgcctcaaaaaaaaaaaagttgtcgatagaaatatggctgctgtttccagaaaataacattgac huGLC1A acagagattgatcatatagcatttacctatctatacccagcacttaactatctataataattacatttaaaattacaacagccctactaccaaaac
moGLC1A tgtttattagcaatccctgctaacactgaagtctctatgagaggctaacacgaaggggtatgttgagggatccgacaccctcacacagacatacatgca huGLC1A actattagtatcccctttacacatgcgataactgaggcgtagagagctaagtaacttactgaaagtcacacagccagcgggtggtagagcctagcttta
moGLC1A ggcaaaacaccaatgcacacaaaagaaaaacaaatgagaaaagtcaaggctcacagagctaagtacctcactgtcactgtgggcagcggggttc huGLC1A aacccagacgatttgtctccaggggctgtcacatctccaagcttccgcatgatcattgtctctgtgtttgaaagattatgattaagtggtg
moGLC1A agaggtcaaccactctgtctctgccttctgtttgccactactgtccagtctgcagtctgtattcggaagacatagatactaaatacatgcaactc huGLC1A cttcgtttcttttttctgaatttaccagGATGTGGAGAGAACTAGTTTGGGTAGGAGAGCCTCTCACGCTGAGAACAGCAGAAACAATTACTGGCAAGTATGG
 ******** * **********  ** * **** ******
moGLC1A tttttttttgttttaattcatcagGATGTGGAGCGCTAGTGGAGAGCCAGTCACCCTGAGGAGCCAGCTGAAACAATGCTGGCAAGTATGG huGLC1A TGTGTGGATGCGAGACCCCAAGCCCCACCTACACCCCTACACCCAGGAGAGAGCCACGTTGGCACGAGAATCGACACAGTTGGCACGGATGTCCGCCAGGATGTCCGCCAGGTTTTTGAGTAT
 ******** * ********** ***** * * **  * ** *  ******
AGTGTGGATGAGAGAGACCCCAAGCCCCACCCCCTACACCCAGGAAAGCACACATGGAGGATTGACACGGTTGGCCACAGATCCGCCAGGTGTTTGAGTAC huGLC1A GACCCTCATCAGCAGTTTATGCAGGGCTACCCTTCTAAGGTTCACATACTGCCTAGGCCACTGGAAAGCACGGGTGCTGTGTGGTGTGTGGGGAGCCTCT
 *  **  **** *   *** ** * ** * ******* *********
AGTCAGATAAGCCAGTTCGAGCAGGCTATCCTTCCAAGGTCCATGTGCTCCCCTCGGGCACTGGAGAGCACGGGTGCTGTGGTGTATGCGGGGAGCCTCT

Fig. 1C-1

```
huGLC1A  ATTTCCAGGGGCGCTGAGTCCAGAAACTGTCATAAGATATGAGCTGAATACCGAGAACAGTGAAGGCTGAGAAGGAAATCCCTGGAGCTGGCTACCACGGACA
         ********** ********** ** ********* * ** ********* * ** ********* ***********************************
moGLC1A  ATTTCCAGGGGCTGAGTCCAGAAACTGTGGTCAGTATGAGCTAGACACGGAGAACCGTGAAGGCAGAGAAGGAGAATTCCTGAGCTGGCTACCACGGACA huGLC1A  GTTCCCGTATTCTTGGGGTGGCTAGACGGACATTGACTTGGCTGTGTGGATGAAGCAGGCCCTCTGGGTCATTTACAGCACCGATGAGGCCAAAGGTGCCATT
         ********** * ********* ******* ********* ***** ******   **  *****
moGLC1A  CTTCCCGTACGCGTGGGGTGGCTACACAGACATTGACTTAGCTGTGTGGATGAGAGCGGCCCTCTGGGTCATCTCAGCACGGAGGAAGCCAAGGGGGCCATA huGLC1A  GTCCTCTCCAAACTGAACCCAGAGAATCTGGAACTCGAACAAACCTGGGAGACAAACATCCGTAAGCAGTCAGTCGCCAATGCCTTCATCATCGTGGCA
         ******** * ****** ********  *  ********  *********************************
moGLC1A  GTCCTCTCCAAATTGAACCCAGCCGTGGGGTGGCTACACATGGGAGACTAACATCCGTAAGCAGTCAGTCGCTGTGGCCAATGCCTTTGTTATCGTGGCA huGLC1A  CCTTGTACACCGTCAGCAGCTACACCTCAGCAGATGCTACCGTCAACTTTGCTTATGACACAGGCACAGATCAGCAAGACCCTGACCATCCATTCAA
           *   *  *   * * *********************************
moGLC1A  TCTTGTACACGGTGAGCAGCTACTCTCTTCAGCCCATGCAACCGTCAACCTCCGCCTACGACACAGATAAAACGGGACCAGTAAGACCCTGACCATCCATTCAC huGLC1A  GAACCGCTATAAGTACAGCAGCATGATTGACTACTACAACCCCCTGGAGAAGAGCTCTTTGCCTGGGACAACTTGAACATGGTCACTTATGACATCAAGCTC
         * ** ******* ********** * ******** * *********************************
moGLC1A  GAATCGCTACAAGTACACAGCAGTATGATTGACTATGACTACAACCCCCTGGAGAGGAAGAGCTGTTTGCCTGGGACAACTTCAACATGGTCACCTATGATATCAAGCTC huGLC1A  TCCAAGATGtgaaaagcctccaagctgtacaggcaatgcagaaggagatgtcagggctcctggggagcaggctgaaggagagcagccagcagg
         * ********
moGLC1A  TTGGAGATGtgaggagctcagccctctatgcctaccagcaaggccagaaaaggtgaagttccggctcccgggtgaagcagctgtcagcagaggcagccagatgc huGLC1A  gcccaggcagctttgactgctttccaagttttcattaatccagaaggatgaacatgtcaccatctaactattcaggaattgtagtctgagggcgtagac
moGLC1A  atggagtttctcctcctgctaaagattttgtttatccgggtcaatgtacacgtagctagctccctctgactgacacgtcctccagcttgtatagtcgcatag
```

Fig. 1C-2

```
                    poly-A
huGLC1A   aatttcatatataataatatccttatcttctgtcagcatttatggatgtgtttaatgacatagttcaagtttcttgtgatttggggcaaaagctgtaagg
moGLC1A   actctgttctctccttttctgtcagctttcaaagggctgttcctcttttaaaaatcacata
                                                                              poly-A
huGLC1A   cataatagttcttcctgaaaaccatgctctgcatgttacatggttaccacaagccacaataaaagcataacttctaaaggaagcagaatagctcct huGLC1A   ctggccagcatcgaatataagtaagatgcatttactacagttggcttctaatgcttcagatagaatacagttgggtctcacataaccctttacattgtga
          poly-A
huGLC1A   aataaattttcttaccacgttctctcttcctgaactttgtgggaatctttgcttaagagaagatatagattccaaccatcagtaattccttcagt
                         (CA) repeat polymorphism
huGLC1A   tgggagatgtgattgcaggatgttaaaggtggtgtgtgtgtgtgtgtgtgtgtaactgagaggcttgtgcctgttttgaggtgctgccaggatg huGLC1A   acgccaagcaaatagcagcatccacactttccacctccatctcctggtgctctcggcactaccggagcaatctttccatctctcccctgaaccaccct
```

Fig. 1C-3

Sequence conservation between huGLC1A and moGLC1A

```
                              H
1    huGLC1A    MRFFCARCCS FGPEMPAVQL LLLACLVWDV GARTAQLRKA NDQSGRCQYT
                ***        * * ****** ****** *** ** *******
     moGLC1A               MPALHL LFLACLVWGM GARTAQFRKA NDRSGRCQYT

C
51   huGLC1A    FSVASPNESS CPEQSQAMSV IHNLQRDSST QRLDLEATKA RLSSLESLLH
                * ******** **    **** * ****** * *** *** * *******
     moGLC1A    FTVASPNESS CPREDQAMSA IQDLQRDSSI QHADLESTKA RVRSLESLLH 101  huGLC1A    QLTLDQAARP QETQEGLQRE LGTLRRERDQ LETQTRELET AYSNLLRDKS
                *         ***   ***** **    *****
     moGLC1A    QMTLGRVTGT QEAQEGLQGQ LGALRRERDQ LETQTRDLEA AYNNLLRDKS 151  huGLC1A    VLEEEKKRLR QENENLARRL ESSSQEVARL RRGQCPQTRD TARAVPPGSR
                *****   *  **       **** *         ****
     moGLC1A    ALEEEKRQLE QENEDLARRL ESSSEEVTRL RRGQCPSTQY PSQDMLPGSR 201  huGLC1A    EVSTWNLDTL AFQELKSELT EVPASRILKE SPSGYLRSGE GDTGCGELVW
                * ** ****** *    *   ** *  * ***
     moGLC1A    EVSQWNLDTL AFQELKSELT EVPASQILKE NPSGRPRSKE GDKGCGALVW

R        K
251  huGLC1A    VGEPLTLRTA ETITGKYGVW MRDPKPTYPY TQETTWRIDT VGTDVRQVFE
                **** ***** *** ****** ******* ** *** ****** ***   *****
     moGLC1A    VGEPVTLRTA ETIAGKYGVW MRDPKPTHPY TQESTWRIDT VGTEIRQVFE 301  huGLC1A    YDLISQFMQG YPSKVHILPR PLESTGAVVY SGSLYFQGAE SRTVIRYELN
                *  **  **** * ******* *****   **
     moGLC1A    YSQISQFEQG YPSKVHVLPR ALESTGAVVY AGSLYFQGAE SRTVVRYELD

S V  1           M G                      2
351  huGLC1A    TETVKAEKEI PGAGYHGQFP YSWGGYTDID LAVDEAGLWV IYSTDEAKGA
                ********** *******  ** *  ******** ***** **** **** *****
     moGLC1A    TETVKAEKEI PGAGYHGHFP YAWGGYTDID LAVDESGLWV IYSTEEAKGA

H                    H         V
401  huGLC1A    IVLSKLNPEN LELEQTWETN IRKQSVANAF IICGTLYTVS SYTSADATVN
                ******** * **** ***** ********** *** ***** ** ** ****
     moGLC1A    IVLSKLNPAN LELERTWETN IRKQSVANAF VICGILYTVS SYSSAHATVN

C         N                           R
451  huGLC1A    FAYDTGTGIS KTLTIPFKNR YKYSSMIDYN PLEKKLFAWD NLNMVTYDIK
                ***** **   ******* ** ********** *** ****** **********
     moGLC1A    FAYDTKTGTS KTLTIPFTNR YKYSSMIDYN PLERKLFAWD NFNMVTYDIK 501  huGLC1A    LSKM
                *  *
     moGLC1A    LLEM
```

Fig. 3

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 2800 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 1:

```
AGCGCAGGGG AGGAGAAGAA AAGAGAGGGA TAGTGTATGA GCAAGAAAGA CAGATTCATT       60

CAAGGGCAGT GGGAATTGAC CACAGGGATT ATAGTCCACG TGATCCTGGG TTCTAGGAGG      120

CAGGGCTATA TTGTGGGGGG AAAAAATCAG TTCAAGGGAA GTCGGGAGAC CTGATTTCTA      180

ATACTATATT TTTCCTTTAC AAGCTGAGTA ATTCTGAGCA AGTCACAAGG TAGTAACTGA      240

GGCTGTAAGA TTACTTAGTT TCTCCTTATT AGGAACTCTT TTTCTCTGTG GAGTTAGCAG      300

CACAAGGGCA ATCCCGTTTC TTTTAACAGG AAGAAAACAT TCCTAAGAGT AAAGCCAAAC      360

AGATTCAAGC CTAGGTCTTG CTGACTATAT GATTGGTTTT TTGAAAAATC ATTTCAGCGA      420

TGTTTACTAT CTGATTCAGA AAATGAGACT AGTACCCTTT GGTCAGCTGT AAACAAACAC      480

CCATTTGTAA ATGTCTCAAG TTCAGGCTTA ACTGCAGAAC CAATCAAATA AGAATAGAAT      540

CTTTAGAGCA AACTGTGTTT CTCCACTCTG GAGGTGAGTC TGCCAGGGCA GTTTGGAAAT      600

ATTTACTTCA CAAGTATTGA CACTGTTGTT GGTATTAACA ACATAAAGTT GCTCAAAGGC      660

AATCATTATT TCAAGTGGCT TAAAGTTACT TCTGACAGTT TTGGTATATT TATTGGCTAT      720

TGCCATTTGC TTTTTGTTTT TTCTCTTTGG GTTTATTAAT GTAAAGCAGG GATTATTAAC      780

CTACAGTCCA GAAAGCCTGT GAATTTGAAT GAGGAAAAAA TTACATTTTT GTTTTTACCA      840

CCTTCTAACT AAATTTAACA TTTTATTCCA TTGCGAATAG AGCCATAAAC TCAAAGTGGT      900
```

```
AATAACAGTA CCTGTGATTT TGTCATTACC AATAGAAATC ACAGACATTT TATACTATAT    960

TACAGTTGTT GCAGATACGT TGTAAGTGAA ATATTTATAC TCAAAACTAC TTTGAAATTA   1020

GACCTCCTGC TGGATCTTGT TTTTAACATA TTAATAAAAC ATGTTTAAAA TTTTGATATT   1080

TTGATAATCA TATTTCATTA TCATTTGTTT CCTTTGTAAT CTATATTTTA TATATTTGAA   1140

AACATCTTTC TGAGAAGAGT TCCCCAGATT TCACCAATGA GGTTCTTGGC ATGCACACAC   1200

ACAGAGTAAG AACTGATTTA GAGGCTAACA TTGACATTGG TGCCTGAGAT GCAAGACTGA   1260

AATTAGAAAG TTCTCCCAAA GATACACAGT TGTTTTAAAG CTAGGGGTGA GGGGGGAAAT   1320

CTGCCGCTTC TATAGGAATG CTCTCCCTGG AGCCTGGTAG GGTGCTGTCC TTGTGTTCTG   1380

GCTGGCTGTT ATTTTTCTCT GTCCCTGCTA CGTCTTAAAG GACTTGTTTG GATCTCCAGT   1440

TCCTAGCATA GTGCCTGGCA CAGTGCAGGT TCTCAATGAG TTTGCAGAGT GAATGGAAAT   1500

ATAAACTAGA AATATATCCT TGTTGAAATC AGCACACCAG TAGTCCTGGT GTAAGTGTGT   1560

GTACGTGTGT GTGTGTGTGT GTGTGTGTGT GTAAAACCAG GTGGAGATAT AGGAACTATT   1620

ATTGGGGTAT GGGTGCATAA ATTGGGATGT TCTTTTTAAA AAGAAACTCC AAACAGACTT   1680

CTGGAAGGTT ATTTTCTAAG AATCTTGCTG GCAGCGTGAA GGCAACCCCC CTGTGCACAG   1740

CCCCACCCAG CCTCACGTGG CCACCTCTGT CTTCCCCCAT GAAGGGCTGG CTCCCCAGTA   1800

TATATAAACC TCTCTGGAGC TCGGGCATGA CCAGCAAGG CCACCCATCC AGGCACCTCT    1860

CAGCACAGCA GAGCTTTCCA GAGGAAGCCT CACCAAGCCT CTGCAATGAG GTTCTTCTGT   1920

GCACGTTGCT GCAGCTTTGG GCCTGAGATG CCAGCTGTCC AGCTGCTGCT TCTGGCCTGC   1980

CTGGTGTGGG ATGTGGGGGC CAGGACAGCT CAGCTCAGGA AGGCCAATGA CCAGAGTGGC   2040

CGATGCCAGT ATACCTTCAG TGTGGCCAGT CCCAATGAAT CCAGCTGCCC AGAGCAGAGC   2100

CAGGCCATGT CAGTCATCCA TAACTTACAG AGAGACAGCA GCACCCAACG CTTAGACCTG   2160

GAGGCCACCA AAGCTCGACT CAGCTCCCTG GAGAGCCTCC TCCACCAATT GACCTTGGAC   2220

CAGGCTGCCA GGCCCCAGGA GACCCAGGAG GGGCTGCAGA GGGAGCTGGG CACCCTGAGG   2280

CGGGAGCGGG ACCAGCTGGA AACCCAAACC AGAGAGTTGG AGACTGCCTA CAGCAACCTC   2340

CTCCGAGACA AGTCAGTTCT GGAGGAAGAG AAGAAGCGAC TAAGGCAAGA AAATGAGAAT   2400

CTGGCCAGGA GGTTGGAAAG CAGCAGCCAG GAGGTAGCAA GGCTGAGAAG GGGCCAGTGT   2460

CCCCAGACCC GAGACACTGC TCGGGCTGTG CCACCAGGCT CCAGAGAAGG TAAGAATGCA   2520

GAGTGGGGGG ACTCTGAGTT CAGCAGGTGA TATGGCTCGT AGTGACCTGC TACAGGCGCT   2580

CCAGGCCTCC CTGCCTGCCC TTTCTCCTAG AGACTGCACA GCTAGCACAA GACAGATGAA   2640

TTAAGGAAAG CACAGCGATC ACCTTCAAGT ATTACTAGTA ATTTAGCTCC TGAGAGCTTC   2700

ATTTAGATTA GTGGTTCAGA GTTCTTGTGC CCCTCCATGT CAGTTTTCAC AGTCCATAGC   2760

AAAAGGAGAA ATAAAAGGAC CGGGTGAGAT GTGTCTGCAT                         2800
```

(2) INFORMATION FOR SEQ ID NO: 2:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

```
CACCATGTTG GCCAGGCTGG TCTCGAACTC CTGACCTCAG GTGATCCGCC TGCCTCGGCC    60
```

-continued

```
TCCCAAAGTG CTGGGATTAC AGGCATGAGC CACCACGCCT GGCCGGCAGC CTATTTAAAT       120

GTCATCCTCA ACATAGTCAA TCCTTGGGCC ATTTTTTCTT ACAGTAAAAT TTTGTCTCTT       180

TCTTTTAATG CAGTTTCTAC GTGGAATTTG GACACTTTGG CCTTCCAGGA ACTGAAGTCC       240

GAGCTAACTG AAGTTCCTGC TTCCCGAATT TTGAAGGAGA GCCCATCTGG CTATCTCAGG       300

AGTGGAGAGG GAGACACCGG TATGAAGTTA AGTTTCTTCC CTTTTGTGCC CACATGGTCT       360

TTATTCATGT CTAGTGCTGT GTTCAGAGAA TCAGTATAGG GTAAATGCCC ACCCAAGGGG       420

GAAATTAACT TCCCTGGGAG CAGAGGGAGG GGAGGAGAAG AGGAACAGAA CTCTCTCTCT       480

CTCTCTGTTC CCTTGTCAGA GCAGGTCTGC AGGAGTCAGC CTTTCCCTAA CAAAGCCCTC       540

TATCCTATCA CCCACACTTG GGAGGCTGGG CTGGGCTGCA CAGGGCAAGA TGAGAGATGT       600

GTTGATTTCA TCCACTTGAT TGTCATGTAG AATTAGATAT ACTTGAGAAG TTACATTTTT       660

CAGTAGCGCC TTCATATCTT                                                  680
```

(2) INFORMATION FOR SEQ ID NO: 3:

(i) SEQUENCE CHARACTERISTICS:
        (A) LENGTH: 2000 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

```
CTTACAACTG ATACTGAGTG AATTGTACTT TAAATATTTT ATAGCTCCCA CTCCCATGCA        60

TGCCCCTCAG TGATAGCAAT AATTGTCAAT AACATGAAAC ACAGATTGAT CATATAGCAT       120

TTACCATATA TTTACTCTAT ACCAAGCACT TAACATATAT AATTACATTT AAAATTTACA       180

ACAGCCCTAC TACCCAAAAC ACTATTAGTA TCCCCTTTTA CACATGCGAT AACTGAGGCG       240

TAGAGAGCTA AGTAACTTAC TGAAAGTCAC ACAGCCAGCG GGTGGTAGAG CCTAGCTTTA       300

AACCCAGACG ATTTGTCTCC AGGGCTGTCA CATCTACTGG CTCTGCCAAG CTTCCGCATG       360

ATCATTGTCT GTGTTTGGAA AGATTATGGA TTAAGTGGTG CTTCGTTTTC TTTTCTGAAT       420

TTACCAGGAT GTGGAGAACT AGTTTGGGTA GGAGAGCCTC TCACGCTGAG AACAGCAGAA       480

ACAATTACTG GCAAGTATGG TGTGTGGATG CGAGACCCCA AGCCCACCTA CCCCTACACC       540

CAGGAGACCA CGTGGAGAAT CGACACAGTT GGCACGGATG TCCGCCAGGT TTTTGAGTAT       600

GACCTCATCA GCCAGTTTAT GCAGGGCTAC CCTTCTAAGG TTCACATACT GCCTAGGCCA       660

CTGGAAAGCA CGGGTGCTGT GGTGTACTCG GGGAGCCTCT ATTTCCAGGG CGCTGAGTCC       720

AGAACTGTCA TAAGATATGA GCTGAATACC GAGACAGTGA AGGCTGAGAA GGAAATCCCT       780

GGAGCTGGCT ACCACGGACA GTTCCCGTAT TCTTGGGGTG GCTACACGGA CATTGACTTG       840

GCTGTGGATG AAGCAGGCCT CTGGGTCATT TACAGCACCG ATGAGGCCAA AGGTGCCATT       900

GTCCTCTCCA AACTGAACCC AGAGAATCTG GAACTCGAAC AAACCTGGGA GACAAACATC       960

CGTAAGCAGT CAGTCGCCAA TGCCTTCATC ATCTGTGGCA CCTTGTACAC CGTCAGCAGC      1020

TACACCTCAG CAGATGCTAC CGTCAACTTT GCTTATGACA CAGGCACAGG TATCAGCAAG      1080

ACCCTGACCA TCCCATTCAA GAACCGCTAT AAGTACAGCA GCATGATTGA CTACAACCCC      1140

CTGGAGAAGA AGCTCTTTGC CTGGGACAAC TTGAACATGG TCACTTATGA CATCAAGCTC      1200

TCCAAGATGT GAAAAGCCTC CAAGCTGTAC AGGCAATGGC AGAAGGAGAT GCTCAGGGCT      1260

CCTGGGGGGA GCAGGCTGAA GGGAGAGCCA GCCAGCCAGG GCCCAGGCAG CTTTGACTGC      1320
```

-continued

```
TTTCCAAGTT TTCATTAATC CAGAAGGATG AACATGGTCA CCATCTAACT ATTCAGGAAT    1380

TGTAGTCTGA GGGCGTAGAC AATTTCATAT AATAAATATC CTTTATCTTC TGTCAGCATT    1440

TATGGGATGT TTAATGACAT AGTTCAAGTT TTCTTGTGAT TTGGGGCAAA AGCTGTAAGG    1500

CATAATAGTT TCTTCCTGAA AACCATTGCT CTTGCATGTT ACATGGTTAC CACAAGCCAC    1560

AATAAAAAGC ATAACTTCTA AAGGAAGCAG AATAGCTCCT CTGGCCAGCA TCGAATATAA    1620

GTAAGATGCA TTTACTACAG TTGGCTTCTA ATGCTTCAGA TAGAATACAG TTGGGTCTCA    1680

CATAACCCTT TACATTGTGA AATAAAATTT TCTTACCCAA CGTTCTCTTC CTTGAACTTT    1740

GTGGGAATCT TTGCTTAAGA GAAGGATATA GATTCCAACC ATCAGGTAAT TCCTTCAGGT    1800

TGGGAGATGT GATTGCAGGA TGTTAAAGGT GGTGTGTGTG TGTGTGTGTG TGTGTGTAAC    1860

TGAGAGGCTT GTGCCTGGTT TTGAGGTGCT GCCCAGGATG ACGCCAAGCA AATAGCAGCA    1920

TCCACACTTT CCCACCTCCA TCTCCTGGTG CTCTCGGCAC TACCGGAGCA ATCTTTCCAT    1980

CTCTCCCCTG AACCCACCCT                                                2000

(2) INFORMATION FOR SEQ ID NO: 4:

(i) SEQUENCE CHARACTERISTICS:
        (A) LENGTH: 2800 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

TACCTGGTAC TTGTTGGCTG GCCAATCTAA CCAAATCAGT GATCCCCAAG CTCAGCGAGA      60

CAATCCGTCT CAAAAAAACA AAGTGGAGAA TGAAAGAAGA CAACGCCTGA CATAAGCCTC     120

TAGCTCACAC ACACACACAC ACACACACGC CTATACACAT GAGTGTGCAC CCACCCAGGT     180

GAACGCAGAT GCACACATAC CCCACCCACA CAAGAATGGA TTTAGAGCAA GAGGCACTTG     240

CTCAGTCTTC AGGCGAATCT GCTATGGGAA CATCAGAGAA ATTTATCACA CAGATATCAC     300

AAATGCTATT ATTAGTATCT GAGAACCAAG TTGCTCAAAT GCAAATGTTG CTCTAAGGAA     360

CCCATGAGGG GGCAGTGAGG TGGCTGAGAG GGGGAGGTGC TTAGTGAGCA GGCCTTACAG     420

ACTGAGGTCA GTCCCTAAAG CCCATGCCAG GAGGAGAGAA CTGGACCCCA AAAGTTGTCC     480

TCTGACCACA ACACGGCATG CATGGCCCAT GTGTGCTCAT ATACCCCCCA TATGAGCACA     540

CACCAGTAAG TAAACATTTA TAAAGATGTT CATGAGGCTT CCACGCACAC ACTGGCTTAT     600

GTGAACTTCT GACAAGCCTT GGTACTTGGT ACTTGGTTCT CCTGCTTGGT TTTGGTTTTT     660

TTCATTTATC TTATTTTTTT ATTTGGAGGA AGGTGTGTGT GTGTGTGTGT CTCTCTGTGT     720

GTGTGTCTGT GTGTGTGTGT GTGTGTTGTT GTTGTTGTTG TTGTTGACAG TTTCTTTTTT     780

TAGGAGAAGT CTCATTATAC TGCCCAGTTG TTCTTGAACT CTTTTTGAGA CTTAACAATT     840

CCCTTACATT GCATTCAAAG TAGTGGGCTC TCTTTGAAAA GGGAGTACTA TTAGCTTACA     900

GCCCGTGAAT TTGAATTAGT AAGTAAACTA AATCTCCATT TTCACAACCT TCTCACTCAG     960

TTATTTCATC TCCTCATGGA TAGCTACCTA AACCTAAAGT TATGATAACA ATACCTGTAT    1020

TTTCATCCCT ATGTTACAGT TGATACAGGT TTCATGAAAT ACTGTGTATA CTCAAAAGTA    1080

CTTTAAAATT AAGCCTTATG TTGAATAGCT TATGTAGCAT ACACTTCTGG CATTTAAATA    1140

TTTTCATATT GCTAACTAAA TAACGTGTTT CTTTGAGTCC TTACGTTTTA TACGTTTGGA    1200

GTTATCTTTC AGAGGTGGGC ACACAGGTTT CACCCGTAGG GTTTGGGGGG CACACTCATC    1260
```

```
CTAAAGCCTG GTCCAGAGCA TTGGCACAGG TTCCTGAGAC AAGAGCTGTG GTTAGGGAGC      1320

TTTTCTGAGG ATGTTCACAG GTTTATTCTA AATCTAGGGC AACATCATGT TCTCATCCCC      1380

TCTGTAGGAA CCAGGAGCCT GGAGGCATTG GGCTCTCCTT TGGACTCTTC TTCGTCTCTG      1440

CTACAGGACG TGTCTACTCA GGCATGTCTG TCTCCCTAGT TCCTTATGCT GGTCCAGTGA      1500

AACACAAAAT AGACTTATAT CCCTGTTCAA ACTAGCACAC AACCAGCTTC TCCTGTCAGA      1560

CAAGGTGCGC ATATGTTCAC AAGCACACAC AAACAGACTA GAAACTTAGG GGTTATTATT      1620

GGGATGTGGG GTACATGCAC GGGGACTTCT AAAAAGAAAA TAAATTCAAA ATAGCCTCCG      1680

GCACTTTGTT TTTAAAGACT CTTGCTGGCA GTGTGAGTGT AATCCTCCTA TCCCCCCATG      1740

GCTGGTCCAA CCCAGCTTCA TGTGATCACC TCTCCCTCCC TCCACACAGG GCTGGGTCCC      1800

CAGGATATAT AAATGTCTTT GGACTTCAGG CTTGAGCCAG CAGGGCCACC CATCCAGACA      1860

CCTTGCAGGA GAACTTTCCA GAAGAAACCT CACCCAGCCT CCACACTGCT GTCCTTCTCT      1920

GCACGCTGCT GCAGCTGTGG TCCCAAGATG CCAGCTCTCC ATCTGCTGTT TCTGGCCTGC      1980

TTGGTGTGGG GAATGGGGGC CAGGACAGCA CAGTTCCGAA AGGCCAATGA TCGGAGTGGC      2040

CGATGCCAAT ACACCTTCAC TGTGGCCAGC CCCAATGAAT CTAGCTGCCC AAGGGAGGAC      2100

CAGGCCATGT CAGCCATCCA AGACCTTCAG AGAGACAGCA GCATCCAGCA TGCAGACCTA      2160

GAGTCCACCA AGGCCCGGGT CAGATCCCTG GAGAGTCTCC TCCACCAGAT GACCTTGGGC      2220

CGAGTTACTG GGACCCAGGA GGCCCAAGAG GGGCTGCAGG GCCAGTTGGG TGCCCTGAGG      2280

AGAGAACGGG ACCAGCTGGA GACCCAAACC AGGGATCTGG AGGCAGCCTA TAACAATCTC      2340

CTTCGAGATA AGTCGGCTTT AGAGGAAGAG AAGAGGCAGC TGGAACAAGA GAATGAAGAT      2400

TTGGCCAGGA GGCTAGAAAG CAGCAGCGAG GAGGTAACAA GGCTGCGGAG GGGCCAGTGT      2460

CCTTCCACCC AGTACCCCTC TCAGGACATG CTGCCAGGCT CCAGGGAAGG TAAGAGTGCA      2520

GGGTGGAGTG GCCACCTGAC CCAGAAGGTA GCAAGTTTGC TGGTGACCCA TTACAGGACC      2580

CCCAGGCTTC TCCTTCTGTT TTGTCTTTTC TCTCAGAAAC TGCAAATCCA GCATGCAGTA      2640

GTTTCATTAA GGAGAGCAAA GCAAACACTT TTGCATGCTT CTAGAAAGTT GGCTCCTTGT      2700

TTAGGTCAGT GGATCTGAGC TCTTGTGCCC AGTCATGACA AAATGATCAT GGCCCACAGC      2760

CAAATGACAA ACATGGGGCC AGGTGGCAGA TACATATGAT                            2800
```

(2) INFORMATION FOR SEQ ID NO: 5:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
AAGCTTTTTA ATTATGCCAA TTTCTCCCCG ATTGAGACCA TCACCCTAGT TCCAATGAGC        60

TACCAACGTG GTTCAGTCAT GTTACATCTT CAGATAACAA GTATTTGGGA ACATATCAAA       120

CATCACCCTC CACAGAGTCC GTTCTTGTGC CCTTTCTACT ACAAGTGCCA ATTTTTTCTC       180

TCTTTGAATA CAGTCTCTCA GTGGAATTTG GACACGTTGG CCTTCCAGGA ATTGAAGTCA       240

GAGTTAACTG AGGTTCCTGC TTCCCAAATC TTGAAGGAAA ATCCATCTGG CCGACCCAGG       300

AGCAAAGAAG GAGACAAAGG TATGAAGTTA GACTTCTCCC TTTTGAGCCT ACCTGGCCTC       360

CTCTCCCTCT CTCCCTCTCT CCCTCTCTCC CTCTCTCCCT CTCTCCCTCT CTCCCTCTCT       420
```

```
CCCTCTCTCC CCTCTCCCCT CCCCCTCTCC CTCCCTGTGT GTGTGTGTGA GTGCATGTAT    480

ATGTGTGTGT GTGTGTGTGT GTGTGTGTGT GTGTGTGCAT GTGCGTGTGC ATGTATACCT    540

TGTTCTGTGT TCAGTTCGGA AAGAGCAACT GTTCACCCAG AAGAGAAGAC AGGTGATTCC    600

CCAAGGCAGA GTTGGGGAGA AGGAAGCTGA AACCTGTCTG CTGCCTTTTC TAGACATATG    660

TACTGGAAGC CAACCTTGGA                                                680
```

(2) INFORMATION FOR SEQ ID NO: 6:

(i) SEQUENCE CHARACTERISTICS:
        (A) LENGTH: 1456 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

```
CTTTGTCTAT CAAGGAAAAG AGCATTTGTG CCTCAAAAAA AAAAAAAAAA AAAAGTGTTC     60

GATAGAAATA TGGCTGCTGT TTCCAGAAAA TAACATTGAC TGTTTTATTA GCAATCCCTG    120

CTAACACTGA AGTCTATGTA GAGGCTAACA CGGAAGGGTA TGTTGAGGGG ATCCGACACC    180

CTCACACAGA CATACATGCA GGCAAAACAC CAATGCACAC AAAAGAAAAA CAAATGAGAA    240

AGTCAAGGCT CACAGAGCTA AGTACCTCAC TGGTCACATG GTCAGTGGGC AGCGGGGTTC    300

AGAGGTCAAC CCACTCTGTC TCTGCCTTCT CTGTTTTGCC ACTACTGTCC AGTCTGCAGT    360

CTGTATTCGG AAGACATAGA ACTAAATAC ATGGCAACTC TTTTTTTTGT TTGTTTTAAT     420

TCATCAGGAT GTGGAGCGCT AGTCTGGGTA GGAGAGCCA TCACCCTGAG ACAGCTGAA     480

ACAATCGCTG GCAAGTATGG AGTGTGGATG AGAGACCCCA AGCCCACCCA CCCCTACACC    540

CAGGAAAGCA CATGGAGGAT TGACACGGTT GGCACAGAGA TCCGCCAGGT GTTTGAGTAC    600

AGTCAGATAA GCCAGTTCGA GCAGGGCTAT CCTTCCAAGG TCCATGTGCT CCCTCGGGCA    660

CTGGAGAGCA CGGGTGCTGT GGTGTATGCG GGGAGCCTCT ATTTCCAGGG GGCTGAGTCC    720

AGAACTGTGG TCAGGTATGA GCTAGACACG GAGACCGTGA AGGCAGAGAA GGAAATTCCT    780

GGAGCTGGCT ACCACGGACA CTTCCCGTAC GCGTGGGGTG GCTACACAGA CATTGACTTA    840

GCTGTGGATG AGAGCGGCCT CTGGGTCATC TACAGCACGG AGGAAGCCAA GGGGGCCATA    900

GTCCTCTCCA AATTGAACCC AGCGAACCTG GAACTTGAGC GTACCTGGGA GACTAACATC    960

CGTAAGCAGT CTGTGGCCAA TGCCTTTGTT ATCTGTGGCA TCTTGTACAC GGTGAGCAGC   1020

TACTCTTCAG CCCATGCAAC CGTCAACTTC GCCTACGACA CTAAAACGGG GACCAGTAAG   1080

ACCCTGACCA TCCCATTCAC GAATCGCTAC AAGTACAGCA GTATGATTGA CTACAACCCC   1140

CTGGAGAGGA AGCTGTTTGC CTGGGACAAC TTCAACATGG TCACCTATGA TATCAAGCTC   1200

TTGGAGATGT GAGGAGCCTC TATGCCTACC AGCAAAGGCC AGAAAAGGTG AAGTTCCGGG   1260

CTCCCGGGTG AAGCAGCTGT CAGCAGAGGC AGCCAGATGC ATGGAGTTTC TCCTCCTGCT   1320

AAAGATTTTG TTTATCCGGG TCAATGTACA GCTAGCTCCC CTCTGACTGA CACGTCCTCC   1380

AGGCTTGTAT AGTCGCATAG ACTCTGTTCT CTTCTGTCAG CTTTCAAAGG GCTGTTCCTC   1440

TTTTAAAAAT CACATA                                                  1456
```

(2) INFORMATION FOR SEQ ID NO: 7:

(i) SEQUENCE CHARACTERISTICS:
        (A) LENGTH: 1515 base pairs

```
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1512

(xi) SEQUENCE DESCRIPTION: SEQ ID NO: 7:

ATG AGG TTC TTC TGT GCA CGT TGC TGC AGC TTT GGG CCT GAG ATG CCA      48
Met Arg Phe Phe Cys Ala Arg Cys Cys Ser Phe Gly Pro Glu Met Pro
 1               5                  10                  15

GCT GTC CAG CTG CTG CTT CTG GCC TGC CTG GTG TGG GAT GTG GGG GCC      96
Ala Val Gln Leu Leu Leu Leu Ala Cys Leu Val Trp Asp Val Gly Ala
             20                  25                  30

AGG ACA GCT CAG CTC AGG AAG GCC AAT GAC CAG AGT GGC CGA TGC CAG     144
Arg Thr Ala Gln Leu Arg Lys Ala Asn Asp Gln Ser Gly Arg Cys Gln
         35                  40                  45

TAT ACC TTC AGT GTG GCC AGT CCC AAT GAA TCC AGC TGC CCA GAG CAG     192
Tyr Thr Phe Ser Val Ala Ser Pro Asn Glu Ser Ser Cys Pro Glu Gln
 50                  55                  60

AGC CAG GCC ATG TCA GTC ATC CAT AAC TTA CAG AGA GAC AGC AGC ACC     240
Ser Gln Ala Met Ser Val Ile His Asn Leu Gln Arg Asp Ser Ser Thr
 65                  70                  75                  80

CAA CGC TTA GAC CTG GAG GCC ACC AAA GCT CGA CTC AGC TCC CTG GAG     288
Gln Arg Leu Asp Leu Glu Ala Thr Lys Ala Arg Leu Ser Ser Leu Glu
                 85                  90                  95

AGC CTC CTC CAC CAA TTG ACC TTG GAC CAG GCT GCC AGG CCC CAG GAG     336
Ser Leu Leu His Gln Leu Thr Leu Asp Gln Ala Ala Arg Pro Gln Glu
            100                 105                 110

ACC CAG GAG GGG CTG CAG AGG GAG CTG GGC ACC CTG AGG CGG GAG CGG     384
Thr Gln Glu Gly Leu Gln Arg Glu Leu Gly Thr Leu Arg Arg Glu Arg
        115                 120                 125

GAC CAG CTG GAA ACC CAA ACC AGA GAG TTG GAG ACT GCC TAC AGC AAC     432
Asp Gln Leu Glu Thr Gln Thr Arg Glu Leu Glu Thr Ala Tyr Ser Asn
    130                 135                 140

CTC CTC CGA GAC AAG TCA GTT CTG GAG GAA GAG AAG AAG CGA CTA AGG     480
Leu Leu Arg Asp Lys Ser Val Leu Glu Glu Glu Lys Lys Arg Leu Arg
145                 150                 155                 160

CAA GAA AAT GAG AAT CTG GCC AGG AGG TTG GAA AGC AGC AGC CAG GAG     528
Gln Glu Asn Glu Asn Leu Ala Arg Arg Leu Glu Ser Ser Ser Gln Glu
                165                 170                 175

GTA GCA AGG CTG AGA AGG GGC CAG TGT CCC CAG ACC CGA GAC ACT GCT     576
Val Ala Arg Leu Arg Arg Gly Gln Cys Pro Gln Thr Arg Asp Thr Ala
            180                 185                 190

CGG GCT GTG CCA CCA GGC TCC AGA GAA GTT TCT ACG TGG AAT TTG GAC     624
Arg Ala Val Pro Pro Gly Ser Arg Glu Val Ser Thr Trp Asn Leu Asp
        195                 200                 205

ACT TTG GCC TTC CAG GAA CTG AAG TCC GAG CTA ACT GAA GTT CCT GCT     672
Thr Leu Ala Phe Gln Glu Leu Lys Ser Glu Leu Thr Glu Val Pro Ala
    210                 215                 220

TCC CGA ATT TTG AAG GAG AGC CCA TCT GGC TAT CTC AGG AGT GGA GAG     720
Ser Arg Ile Leu Lys Glu Ser Pro Ser Gly Tyr Leu Arg Ser Gly Glu
225                 230                 235                 240

GGA GAC ACC GGA TGT GGA GAA CTA GTT TGG GTA GGA GAG CCT CTC ACG     768
Gly Asp Thr Gly Cys Gly Glu Leu Val Trp Val Gly Glu Pro Leu Thr
                245                 250                 255

CTG AGA ACA GCA GAA ACA ATT ACT GGC AAG TAT GGT GTG TGG ATG CGA     816
Leu Arg Thr Ala Glu Thr Ile Thr Gly Lys Tyr Gly Val Trp Met Arg
            260                 265                 270
```

```
GAC CCC AAG CCC ACC TAC CCC TAC ACC CAG GAG ACC ACG TGG AGA ATC        864
Asp Pro Lys Pro Thr Tyr Pro Tyr Thr Gln Glu Thr Thr Trp Arg Ile
        275                 280                 285

GAC ACA GTT GGC ACG GAT GTC CGC CAG GTT TTT GAG TAT GAC CTC ATC        912
Asp Thr Val Gly Thr Asp Val Arg Gln Val Phe Glu Tyr Asp Leu Ile
        290                 295                 300

AGC CAG TTT ATG CAG GGC TAC CCT TCT AAG GTT CAC ATA CTG CCT AGG        960
Ser Gln Phe Met Gln Gly Tyr Pro Ser Lys Val His Ile Leu Pro Arg
305                 310                 315                 320

CCA CTG GAA AGC ACG GGT GCT GTG GTG TAC TCG GGG AGC CTC TAT TTC       1008
Pro Leu Glu Ser Thr Gly Ala Val Val Tyr Ser Gly Ser Leu Tyr Phe
                325                 330                 335

CAG GGC GCT GAG TCC AGA ACT GTC ATA AGA TAT GAG CTG AAT ACC GAG       1056
Gln Gly Ala Glu Ser Arg Thr Val Ile Arg Tyr Glu Leu Asn Thr Glu
                340                 345                 350

ACA GTG AAG GCT GAG AAG GAA ATC CCT GGA GCT GGC TAC CAC GGA CAG       1104
Thr Val Lys Ala Glu Lys Glu Ile Pro Gly Ala Gly Tyr His Gly Gln
        355                 360                 365

TTC CCG TAT TCT TGG GGT GGC TAC ACG GAC ATT GAC TTG GCT GTG GAT       1152
Phe Pro Tyr Ser Trp Gly Gly Tyr Thr Asp Ile Asp Leu Ala Val Asp
        370                 375                 380

GAA GCA GGC CTC TGG GTC ATT TAC AGC ACC GAT GAG GCC AAA GGT GCC       1200
Glu Ala Gly Leu Trp Val Ile Tyr Ser Thr Asp Glu Ala Lys Gly Ala
385                 390                 395                 400

ATT GTC CTC TCC AAA CTG AAC CCA GAG AAT CTG GAA CTC GAA CAA ACC       1248
Ile Val Leu Ser Lys Leu Asn Pro Glu Asn Leu Glu Leu Glu Gln Thr
                405                 410                 415

TGG GAG ACA AAC ATC CGT AAG CAG TCA GTC GCC AAT GCC TTC ATC ATC       1296
Trp Glu Thr Asn Ile Arg Lys Gln Ser Val Ala Asn Ala Phe Ile Ile
                420                 425                 430

TGT GGC ACC TTG TAC ACC GTC AGC AGC TAC ACC TCA GCA GAT GCT ACC       1344
Cys Gly Thr Leu Tyr Thr Val Ser Ser Tyr Thr Ser Ala Asp Ala Thr
        435                 440                 445

GTC AAC TTT GCT TAT GAC ACA GGC ACA GGT ATC AGC AAG ACC CTG ACC       1392
Val Asn Phe Ala Tyr Asp Thr Gly Thr Gly Ile Ser Lys Thr Leu Thr
        450                 455                 460

ATC CCA TTC AAG AAC CGC TAT AAG TAC AGC AGC ATG ATT GAC TAC AAC       1440
Ile Pro Phe Lys Asn Arg Tyr Lys Tyr Ser Ser Met Ile Asp Tyr Asn
465                 470                 475                 480

CCC CTG GAG AAG AAG CTC TTT GCC TGG GAC AAC TTG AAC ATG GTC ACT       1488
Pro Leu Glu Lys Lys Leu Phe Ala Trp Asp Asn Leu Asn Met Val Thr
                485                 490                 495

TAT GAC ATC AAG CTC TCC AAG ATG TGA                                   1515
Tyr Asp Ile Lys Leu Ser Lys Met
                500
```

(2) INFORMATION FOR SEQ ID NO: 8:

(i) SEQUENCE CHARACTERISTICS:
        (A) LENGTH: 504 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Arg Phe Phe Cys Ala Arg Cys Cys Ser Phe Gly Pro Glu Met Pro
 1               5                  10                  15

Ala Val Gln Leu Leu Leu Leu Ala Cys Leu Val Trp Asp Val Gly Ala
                20                  25                  30
```

-continued

```
Arg Thr Ala Gln Leu Arg Lys Ala Asn Asp Gln Ser Gly Arg Cys Gln
        35                  40                  45

Tyr Thr Phe Ser Val Ala Ser Pro Asn Glu Ser Ser Cys Pro Glu Gln
    50                  55                  60

Ser Gln Ala Met Ser Val Ile His Asn Leu Gln Arg Asp Ser Ser Thr
65                  70                  75                  80

Gln Arg Leu Asp Leu Glu Ala Thr Lys Ala Arg Leu Ser Ser Leu Glu
                85                  90                  95

Ser Leu Leu His Gln Leu Thr Leu Asp Gln Ala Ala Arg Pro Gln Glu
            100                 105                 110

Thr Gln Glu Gly Leu Gln Arg Glu Leu Gly Thr Leu Arg Arg Glu Arg
            115                 120                 125

Asp Gln Leu Glu Thr Gln Thr Arg Glu Leu Glu Thr Ala Tyr Ser Asn
    130                 135                 140

Leu Leu Arg Asp Lys Ser Val Leu Glu Glu Lys Lys Arg Leu Arg Arg
145                 150                 155                 160

Gln Glu Asn Glu Asn Leu Ala Arg Arg Leu Glu Ser Ser Ser Gln Glu
                165                 170                 175

Val Ala Arg Leu Arg Arg Gly Gln Cys Pro Gln Thr Arg Asp Thr Ala
            180                 185                 190

Arg Ala Val Pro Pro Gly Ser Arg Glu Val Ser Thr Trp Asn Leu Asp
    195                 200                 205

Thr Leu Ala Phe Gln Glu Leu Lys Ser Glu Leu Thr Glu Val Pro Ala
    210                 215                 220

Ser Arg Ile Leu Lys Glu Ser Pro Ser Gly Tyr Leu Arg Ser Gly Glu
225                 230                 235                 240

Gly Asp Thr Gly Cys Gly Glu Leu Val Trp Val Gly Glu Pro Leu Thr
                245                 250                 255

Leu Arg Thr Ala Glu Thr Ile Thr Gly Lys Tyr Gly Val Trp Met Arg
            260                 265                 270

Asp Pro Lys Pro Thr Tyr Pro Tyr Thr Gln Glu Thr Thr Trp Arg Ile
    275                 280                 285

Asp Thr Val Gly Thr Asp Val Arg Gln Val Phe Glu Tyr Asp Leu Ile
    290                 295                 300

Ser Gln Phe Met Gln Gly Tyr Pro Ser Lys Val His Ile Leu Pro Arg
305                 310                 315                 320

Pro Leu Glu Ser Thr Gly Ala Val Val Tyr Ser Gly Ser Leu Tyr Phe
                325                 330                 335

Gln Gly Ala Glu Ser Arg Thr Val Ile Arg Tyr Glu Leu Asn Thr Glu
            340                 345                 350

Thr Val Lys Ala Glu Lys Glu Ile Pro Gly Ala Gly Tyr His Gly Gln
    355                 360                 365

Phe Pro Tyr Ser Trp Gly Gly Tyr Thr Asp Ile Asp Leu Ala Val Asp
    370                 375                 380

Glu Ala Gly Leu Trp Val Ile Tyr Ser Thr Asp Glu Ala Lys Gly Ala
385                 390                 395                 400

Ile Val Leu Ser Lys Leu Asn Pro Glu Asn Leu Glu Leu Glu Gln Thr
                405                 410                 415

Trp Glu Thr Asn Ile Arg Lys Gln Ser Val Ala Asn Ala Phe Ile Ile
            420                 425                 430

Cys Gly Thr Leu Tyr Thr Val Ser Ser Tyr Thr Ser Ala Asp Ala Thr
    435                 440                 445

Val Asn Phe Ala Tyr Asp Thr Gly Thr Gly Ile Ser Lys Thr Leu Thr
```

```
                450                  455                  460
Ile Pro Phe Lys Asn Arg Tyr Lys Tyr Ser Ser Met Ile Asp Tyr Asn
465                 470                  475                  480

Pro Leu Glu Lys Lys Leu Phe Ala Trp Asp Asn Leu Asn Met Val Thr
                485                  490                  495

Tyr Asp Ile Lys Leu Ser Lys Met
            500
```

(2) INFORMATION FOR SEQ ID NO: 9:

(i) SEQUENCE CHARACTERISTICS:
        (A) LENGTH: 1473 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1470

(xi) SEQUENCE DESCRIPTION: SEQ ID NO: 9:

```
ATG CCA GCT CTC CAT CTG CTG TTT CTG GCC TGC TTG GTG TGG GGA ATG        48
Met Pro Ala Leu His Leu Leu Phe Leu Ala Cys Leu Val Trp Gly Met
1               5                   10                  15

GGG GCC AGG ACA GCA CAG TTC CGA AAG GCC AAT GAT CGG AGT GGC CGA        96
Gly Ala Arg Thr Ala Gln Phe Arg Lys Ala Asn Asp Arg Ser Gly Arg
                20                  25                  30

TGC CAA TAC ACC TTC ACT GTG GCC AGC CCC AAT GAA TCT AGC TGC CCA       144
Cys Gln Tyr Thr Phe Thr Val Ala Ser Pro Asn Glu Ser Ser Cys Pro
            35                  40                  45

AGG GAG GAC CAG GCC ATG TCA GCC ATC CAA GAC CTT CAG AGA GAC AGC       192
Arg Glu Asp Gln Ala Met Ser Ala Ile Gln Asp Leu Gln Arg Asp Ser
    50                  55                  60

AGC ATC CAG CAT GCA GAC CTA GAG TCC ACC AAG GCC CGG GTC AGA TCC       240
Ser Ile Gln His Ala Asp Leu Glu Ser Thr Lys Ala Arg Val Arg Ser
65                  70                  75                  80

CTG GAG AGT CTC CTC CAC CAG ATG ACC TTG GGC CGA GTT ACT GGG ACC       288
Leu Glu Ser Leu Leu His Gln Met Thr Leu Gly Arg Val Thr Gly Thr
                85                  90                  95

CAG GAG GCC CAA GAG GGG CTG CAG GGC CAG TTG GGT GCC CTG AGG AGA       336
Gln Glu Ala Gln Glu Gly Leu Gln Gly Gln Leu Gly Ala Leu Arg Arg
                100                 105                 110

GAA CGG GAC CAG CTG GAG ACC CAA ACC AGG GAT CTG GAG GCA GCC TAT       384
Glu Arg Asp Gln Leu Glu Thr Gln Thr Arg Asp Leu Glu Ala Ala Tyr
            115                 120                 125

AAC AAT CTC CTT CGA GAT AAG TCG GCT TTA GAG GAA GAG AAG AGG CAG       432
Asn Asn Leu Leu Arg Asp Lys Ser Ala Leu Glu Glu Glu Lys Arg Gln
    130                 135                 140

CTG GAA CAA GAG AAT GAA GAT TTG GCC AGG AGG CTA GAA AGC AGC AGC       480
Leu Glu Gln Glu Asn Glu Asp Leu Ala Arg Arg Leu Glu Ser Ser Ser
145                 150                 155                 160

GAG GAG GTA ACA AGG CTG CGG AGG GGC CAG TGT CCT TCC ACC CAG TAC       528
Glu Glu Val Thr Arg Leu Arg Arg Gly Gln Cys Pro Ser Thr Gln Tyr
                165                 170                 175

CCC TCT CAG GAC ATG CTG CCA GGC TCC AGG GAA GTC TCT CAG TGG AAT       576
Pro Ser Gln Asp Met Leu Pro Gly Ser Arg Glu Val Ser Gln Trp Asn
                180                 185                 190

TTG GAC ACG TTG GCC TTC CAG GAA TTG AAG TCA GAG TTA ACT GAG GTT       624
Leu Asp Thr Leu Ala Phe Gln Glu Leu Lys Ser Glu Leu Thr Glu Val
            195                 200                 205
```

```
CCT GCT TCC CAA ATC TTG AAG GAA AAT CCA TCT GGC CGA CCC AGG AGC      672
Pro Ala Ser Gln Ile Leu Lys Glu Asn Pro Ser Gly Arg Pro Arg Ser
        210                 215                 220

AAA GAA GGA GAC AAA GGA TGT GGA GCG CTA GTC TGG GTA GGA GAG CCA      720
Lys Glu Gly Asp Lys Gly Cys Gly Ala Leu Val Trp Val Gly Glu Pro
225                 230                 235                 240

GTC ACC CTG AGG ACA GCT GAA ACA ATC GCT GGC AAG TAT GGA GTG TGG      768
Val Thr Leu Arg Thr Ala Glu Thr Ile Ala Gly Lys Tyr Gly Val Trp
                245                 250                 255

ATG AGA GAC CCC AAG CCC ACC CAC CCC TAC ACC CAG GAA AGC ACA TGG      816
Met Arg Asp Pro Lys Pro Thr His Pro Tyr Thr Gln Glu Ser Thr Trp
            260                 265                 270

AGG ATT GAC ACG GTT GGC ACA GAG ATC CGC CAG GTG TTT GAG TAC AGT      864
Arg Ile Asp Thr Val Gly Thr Glu Ile Arg Gln Val Phe Glu Tyr Ser
        275                 280                 285

CAG ATA AGC CAG TTC GAG CAG GGC TAT CCT TCC AAG GTC CAT GTG CTC      912
Gln Ile Ser Gln Phe Glu Gln Gly Tyr Pro Ser Lys Val His Val Leu
    290                 295                 300

CCT CGG GCA CTG GAG AGC ACG GGT GCT GTG GTG TAT GCG GGG AGC CTC      960
Pro Arg Ala Leu Glu Ser Thr Gly Ala Val Val Tyr Ala Gly Ser Leu
305                 310                 315                 320

TAT TTC CAG GGG GCT GAG TCC AGA ACT GTG GTC AGG TAT GAG CTA GAC     1008
Tyr Phe Gln Gly Ala Glu Ser Arg Thr Val Val Arg Tyr Glu Leu Asp
                325                 330                 335

ACG GAG ACC GTG AAG GCA GAG AAG GAA ATT CCT GGA GCT GGC TAC CAC     1056
Thr Glu Thr Val Lys Ala Glu Lys Glu Ile Pro Gly Ala Gly Tyr His
            340                 345                 350

GGA CAC TTC CCG TAC GCG TGG GGT GGC TAC ACA GAC ATT GAC TTA GCT     1104
Gly His Phe Pro Tyr Ala Trp Gly Gly Tyr Thr Asp Ile Asp Leu Ala
        355                 360                 365

GTG GAT GAG AGC GGC CTC TGG GTC ATC TAC AGC ACG GAG GAA GCC AAG     1152
Val Asp Glu Ser Gly Leu Trp Val Ile Tyr Ser Thr Glu Glu Ala Lys
    370                 375                 380

GGG GCC ATA GTC CTC TCC AAA TTG AAC CCA GCG AAC CTG GAA CTT GAG     1200
Gly Ala Ile Val Leu Ser Lys Leu Asn Pro Ala Asn Leu Glu Leu Glu
385                 390                 395                 400

CGT ACC TGG GAG ACT AAC ATC CGT AAG CAG TCT GTG GCC AAT GCC TTT     1248
Arg Thr Trp Glu Thr Asn Ile Arg Lys Gln Ser Val Ala Asn Ala Phe
                405                 410                 415

GTT ATC TGT GGC ATC TTG TAC ACG GTG AGC AGC TAC TCT TCA GCC CAT     1296
Val Ile Cys Gly Ile Leu Tyr Thr Val Ser Ser Tyr Ser Ser Ala His
            420                 425                 430

GCA ACC GTC AAC TTC GCC TAC GAC ACT AAA ACG GGG ACC AGT AAG ACC     1344
Ala Thr Val Asn Phe Ala Tyr Asp Thr Lys Thr Gly Thr Ser Lys Thr
        435                 440                 445

CTG ACC ATC CCA TTC ACG AAT CGC TAC AAG TAC AGC AGT ATG ATT GAC     1392
Leu Thr Ile Pro Phe Thr Asn Arg Tyr Lys Tyr Ser Ser Met Ile Asp
    450                 455                 460

TAC AAC CCC CTG GAG AGG AAG CTG TTT GCC TGG GAC AAC TTC AAC ATG     1440
Tyr Asn Pro Leu Glu Arg Lys Leu Phe Ala Trp Asp Asn Phe Asn Met
465                 470                 475                 480

GTC ACC TAT GAT ATC AAG CTC TTG GAG ATG TGA                         1473
Val Thr Tyr Asp Ile Lys Leu Leu Glu Met
                485                 490

(2) INFORMATION FOR SEQ ID NO: 10:

(i) SEQUENCE CHARACTERISTICS:
        (A) LENGTH: 490 amino acids
        (B) TYPE: amino acid
```

```
            (D) TOPOLOGY: linear (ii) MOLECULE TYPE: protein (xi) SEQUENCE DESCRIPTION: SEQ ID NO: 10:

Met Pro Ala Leu His Leu Leu Phe Leu Ala Cys Leu Val Trp Gly Met
  1               5                  10                  15

Gly Ala Arg Thr Ala Gln Phe Arg Lys Ala Asn Asp Arg Ser Gly Arg
             20                  25                  30

Cys Gln Tyr Thr Phe Thr Val Ala Ser Pro Asn Glu Ser Ser Cys Pro
             35                  40                  45

Arg Glu Asp Gln Ala Met Ser Ala Ile Gln Asp Leu Gln Arg Asp Ser
         50                  55                  60

Ser Ile Gln His Ala Asp Leu Glu Ser Thr Lys Ala Arg Val Arg Ser
 65                  70                  75                  80

Leu Glu Ser Leu Leu His Gln Met Thr Leu Gly Arg Val Thr Gly Thr
                 85                  90                  95

Gln Glu Ala Gln Glu Gly Leu Gln Gly Gln Leu Gly Ala Leu Arg Arg
            100                 105                 110

Glu Arg Asp Gln Leu Glu Thr Gln Thr Arg Asp Leu Glu Ala Ala Tyr
            115                 120                 125

Asn Asn Leu Leu Arg Asp Lys Ser Ala Leu Glu Glu Lys Arg Gln
130                 135                 140

Leu Glu Gln Glu Asn Glu Asp Leu Ala Arg Arg Leu Glu Ser Ser Ser
145                 150                 155                 160

Glu Glu Val Thr Arg Leu Arg Arg Gly Gln Cys Pro Ser Thr Gln Tyr
                165                 170                 175

Pro Ser Gln Asp Met Leu Pro Gly Ser Arg Glu Val Ser Gln Trp Asn
            180                 185                 190

Leu Asp Thr Leu Ala Phe Gln Glu Leu Lys Ser Glu Leu Thr Glu Val
            195                 200                 205

Pro Ala Ser Gln Ile Leu Lys Glu Asn Pro Ser Gly Arg Pro Arg Ser
210                 215                 220

Lys Glu Gly Asp Lys Gly Cys Gly Ala Leu Val Trp Val Gly Glu Pro
225                 230                 235                 240

Val Thr Leu Arg Thr Ala Glu Thr Ile Ala Gly Lys Tyr Gly Val Trp
                245                 250                 255

Met Arg Asp Pro Lys Pro Thr His Pro Tyr Thr Gln Glu Ser Thr Trp
            260                 265                 270

Arg Ile Asp Thr Val Gly Thr Glu Ile Arg Gln Val Phe Glu Tyr Ser
            275                 280                 285

Gln Ile Ser Gln Phe Glu Gln Gly Tyr Pro Ser Lys Val His Val Leu
            290                 295                 300

Pro Arg Ala Leu Glu Ser Thr Gly Ala Val Val Tyr Ala Gly Ser Leu
305                 310                 315                 320

Tyr Phe Gln Gly Ala Glu Ser Arg Thr Val Val Arg Tyr Glu Leu Asp
                325                 330                 335

Thr Glu Thr Val Lys Ala Glu Lys Glu Ile Pro Gly Ala Gly Tyr His
            340                 345                 350

Gly His Phe Pro Tyr Ala Trp Gly Gly Tyr Thr Asp Ile Asp Leu Ala
            355                 360                 365

Val Asp Glu Ser Gly Leu Trp Val Ile Tyr Ser Thr Glu Glu Ala Lys
            370                 375                 380

Gly Ala Ile Val Leu Ser Lys Leu Asn Pro Ala Asn Leu Glu Leu Glu
```

```
385                 390                 395                 400
Arg Thr Trp Glu Thr Asn Ile Arg Lys Gln Ser Val Ala Asn Ala Phe
                405                 410                 415

Val Ile Cys Gly Ile Leu Tyr Thr Val Ser Ser Tyr Ser Ser Ala His
                420                 425                 430

Ala Thr Val Asn Phe Ala Tyr Asp Thr Lys Thr Gly Thr Ser Lys Thr
                435                 440                 445

Leu Thr Ile Pro Phe Thr Asn Arg Tyr Lys Tyr Ser Ser Met Ile Asp
                450                 455                 460

Tyr Asn Pro Leu Glu Arg Lys Leu Phe Ala Trp Asp Asn Phe Asn Met
465                 470                 475                 480

Val Thr Tyr Asp Ile Lys Leu Leu Glu Met
                485                 490
```

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 11:

```
AGGGGCTGCA GAGGGAGCTG GGCACCCTG                                   29
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 12:

```
ATACTGCCTA GGCCACTGGA                                             20
```

(2) INFORMATION FOR SEQ ID NO: 13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 13:

```
CAATGTCCGT GTAGCCACC                                              19
```

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 14:

GAACTCGAAC AAACCTGGGA                                           20

(2) INFORMATION FOR SEQ ID NO: 15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 15:

CATGCTGCTG TACTTATAGC GG                                        22

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 16:

GGCTGGCTCC CCAGTATATA                                           20

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 17:

ACAGCTGGCA TCTCAGGC                                             18

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 18:

ACGTTGCTGC AGCTTTGG                                             18

(2) INFORMATION FOR SEQ ID NO: 19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 19:

GATGACTGAC ATGGCCTGG                                                    19

(2) INFORMATION FOR SEQ ID NO: 20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 20:

AGTGGCCGAT GCCAGTATAC                                                   20

(2) INFORMATION FOR SEQ ID NO: 21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 21:

CTGGTCCAAG GTCAATTGGT                                                   20

(2) INFORMATION FOR SEQ ID NO: 22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 22:

AGGCCATGTC AGTCATCCAT                                                   20

(2) INFORMATION FOR SEQ ID NO: 23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 23:

TCTCTGGTTT GGGTTTCCAG                                                   20

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "primer"

(xi) SEQUENCE DESCRIPTION: SEQ ID NO: 24:

TGACCTTGGA CCAGGCTG                                                   18

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 25:

CCTGGCCAGA TTCTCATTTT                                                 20

(2) INFORMATION FOR SEQ ID NO: 26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 26:

TGGAGGAAGA GAAGAAGCGA                                                 20

(2) INFORMATION FOR SEQ ID NO: 27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 27:

CTGCTGAACT CAGAGTCCCC                                                 20

(2) INFORMATION FOR SEQ ID NO: 28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 28:

AACATAGTCA ATCCTTGGGC C                                               21

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
            (A) DESCRIPTION: /desc = "primer"

(xi) SEQUENCE DESCRIPTION: SEQ ID NO: 29:

TAAAGACCAT GTGGGCACAA                                                    20

(2) INFORMATION FOR SEQ ID NO: 30:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 30:

TTATGGATTA AGTGGTGCTT CG                                                 22

(2) INFORMATION FOR SEQ ID NO: 31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 31:

ATTCTCCACG TGGTCTCCTG                                                    20

(2) INFORMATION FOR SEQ ID NO: 32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 32:

AAGCCCACCT ACCCCTACAC                                                    20

(2) INFORMATION FOR SEQ ID NO: 33:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO: 33:

AATAGAGGCT CCCCGAGTAC A                                                  21

(2) INFORMATION FOR SEQ ID NO: 34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
                 (A) DESCRIPTION: /desc = "primer"

(xi) SEQUENCE DESCRIPTION: SEQ ID NO: 34:

ATACTGCCTA GGCCACTGGA                                                        20

(2) INFORMATION FOR SEQ ID NO: 35:

(i) SEQUENCE CHARACTERISTICS:
                 (A) LENGTH: 19 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "primer"

(xi) SEQUENCE DESCRIPTION: SEQ ID NO: 35:

CAATGTCCGT GTAGCCACC                                                         19

(2) INFORMATION FOR SEQ ID NO: 36:

(i) SEQUENCE CHARACTERISTICS:
                 (A) LENGTH: 19 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "primer"

(xi) SEQUENCE DESCRIPTION: SEQ ID NO: 36:

TGGCTACCAC GGACAGTTC                                                         19

(2) INFORMATION FOR SEQ ID NO: 37:

(i) SEQUENCE CHARACTERISTICS:
                 (A) LENGTH: 20 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "primer"

(xi) SEQUENCE DESCRIPTION: SEQ ID NO: 37:

CATTGGCGAC TGACTGCTTA                                                        20

(2) INFORMATION FOR SEQ ID NO: 38:

(i) SEQUENCE CHARACTERISTICS:
                 (A) LENGTH: 20 base pairs
                 (B) TYPE: nucleic acid
                 (C) STRANDEDNESS: single
                 (D) TOPOLOGY: linear (ii) MOLECULE TYPE: other nucleic acid
                 (A) DESCRIPTION: /desc = "primer"

(xi) SEQUENCE DESCRIPTION: SEQ ID NO: 38:

GAACTCGAAC AAACCTGGGA                                                        20

(2) INFORMATION FOR SEQ ID NO: 39:

(i) SEQUENCE CHARACTERISTICS:
                 (A) LENGTH: 22 base pairs
                 (B) TYPE: nucleic acid
                 (C) STRANDEDNESS: single (D) TOPOLOGY: linear (ii) MOLECULE TYPE: other nucleic acid
        (A) DESCRIPTION: /desc = "primer"

(xi) SEQUENCE DESCRIPTION: SEQ ID NO: 39:

CATGCTGCTG TACTTATAGC GG                                          22

(2) INFORMATION FOR SEQ ID NO: 40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 40:

AGCAAGACCC TGACCATCC                                              19

(2) INFORMATION FOR SEQ ID NO: 41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 41:

AGCATCTCCT TCTGCCATTG                                             20

(2) INFORMATION FOR SEQ ID NO: 42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 42:

TTCCTTCAGG TTGGGAGATG                                             20

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 43:

GAGAGCACCA GGAGATGGAG                                             20

GLAUCOMA THERAPEUTICS AND DIAGNOSTICS

RELATED APPLICATIONS

This application is a continuation-in-part of U.S. Ser. No. 08/822,999 filed on Mar. 21, 1997.

1. GOVERNMENT SUPPORT

Work described herein has been supported, in part, by Public Health Service Research Grants EY10564, EY08905, EY02477, EY02162, EY08426, P50HG00835 and HG00457. The U.S. Government may therefore have certain rights in the invention.

2. BACKGROUND OF THE INVENTION

Glaucoma is an optic nerve disorder characterized by cupping of the optic nerve head and loss of peripheral vision. Occasionally there is also loss of central vision. In the majority of patients, an elevated intraocular pressure is present and is thought to contribute to the optic nerve damage. Glaucoma is the second leading cause of blindness in developed countries (Leske, M. C. (1983) *Am. J. of Epidemiology* 118:166–191). Its prevalence increases with age and is greater in black patients (Leske, M. C. (1983) *Am. J of Epidemiology* 118:166–191). Glaucoma affects approximately 2.3 million Americans and blinds approximately 12,000 of them per year (Tielsch, J. M. (1993) Therapy for glaucoma: costs and consequences. In *Transactions of the New Orleans Academy of Ophthalmologists*, S. F. Ball, Franklin, R. M. (Ed.), pp 61–68. Kugler, Amsterdam).

The most prevalent form of glaucoma is primary open angle glaucoma (POAG), a progressive disease of the optic nerve characterized by degeneration and cupping of the optic nerve, loss of peripheral visual field, and increased intra-ocular pressure. Evidence indicates that POAG is genetically heterogeneous with a complex mode of inheritance. An early onset form of POAG known as juvenile open angle glaucoma (JOAG) is an autosomal dominant disorder with high penetrance.

A significant fraction of glaucoma has a genetic basis (Benedict, T. W. G. Abhaundlungen zus dem Gebiete der Augenheilkunde. Breslau: L. Freunde (1842); Stokes, (1940) *W. Arch Ophthalmol* 24:885–909; Kellerman, L. and A. Posner, (1955) *Am. J. Ophthalmol.*; 40:681–685; Becker, B., et al., (1960) *Am. J. Ophthalmol.* 50:557–567; Francois, J., et. al., (1966) *Am. J. Ophthalmol.*; 62:1067–1071; Armaly, M. F. (1967) *Arch Ophthalmol*; 78:35–43; Davies, T. G. (1968) *Br. J. Ophthalmol.*: 52:31–39; Jay, B., Paterson, G. (1970) *Trans. Ophthalmol. Soc. U.K.*; 90:161–171; Paterson, G. (1970) *Trans. Ophthalmol. Soc. U.K.*; 90:515–525; Miller, S.J.H. (1978) Trans. Ophthalmol. Soc. U.K. 98:290–292), which allows genetic methods to be used to investigate the pathophysiological mechanisms of the disease at the molecular level. The chromosomal locations of genes causing three genetically distinct types of primary open angle glaucoma have been identified (Sheffield, V., et al. (1993) *Nature Genetics* 4:47–50; Sunden, S. L. F., et al. (1996) 6:862–869; Richards, J. E., et al. (1994) *Am. J. Hum. Genet.*: 54:62–70; Wiggs, J. L., et al. (1994) *Genomics*; 21:299–303; Stoilova, D., et al. (1996) *Genomics* 36:142–150; Wirtz, M. K., et al. (1997) *Am. J. Hum. Genet.* 60:296–304).

Therapeutics, which modulate (agonize or antagonize) genes (wild-type or mutant) involved in glaucoma, would be useful for the prevention and treatment of glaucoma. In addition, the detection of mutations in genes that correlate with the existence or a predisposition to the development of glaucoma can provide useful diagnostics.

3. SUMMARY OF THE INVENTION

In one aspect, the invention features isolated GLC1A nucleic acid molecules. The disclosed molecules can be non-coding, (e.g. probe, antisense or ribozyme molecules) or can encode a functional polypeptide (e.g. a polypeptide which specifically modulates, e.g., by acting as either an agonist or antagonist, at least one bioactivity of a myocilin polypeptide).

In further embodiments, the nucleic acid molecule is a GLC1A nucleic acid that is at least 70%, preferably 80%, more preferably 85%, and even more preferably at least 95% homologous in sequence to the nucleic acids shown as SEQ ID No. 7 or 9 or to the complement thereof In another embodiment, the nucleic acid molecule encodes a polypeptide that is at least 92% and more preferably at least 95% similar in sequence to the polypeptide shown in SEQ ID No: 8 or 10.

The invention also provides probes and primers comprising substantially purified oligonucleotides, which correspond to a region of nucleotide sequence which hybridizes to at least about 6 consecutive nucleotides of the sequences set forth as SEQ ID Nos: 1, 2, 3, 4, 5 or 6 or complements of the sequences set forth as SEQ ID Nos: 1, 2, 3, 4, 5 or 6 or naturally occurring mutants thereof. In preferred embodiments, the probe/primer further includes a label group attached thereto, which is capable of being detected.

For expression, the subject GLC1A nucleic acids can include a transcriptional regulatory sequence, e.g. at least one of a transcriptional promoter (e.g., for constitutive expression or inducible expression) or transcriptional enhancer or suppressor sequence, which regulatory sequence is operably linked to the GLC1A gene sequence. Such regulatory sequences in conjunction with a GLC1A nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing GLC1A proteins by employing said expression vectors.

In another aspect, the invention features isolated myocilin polypeptides, preferably substantially pure preparations, e.g. of plasma purified or recombinantly produced myocilin polypeptides. In one embodiment, the polypeptide is identical to or similar to a myocilin protein represented in SEQ ID No: 8 or 10. Related members of the vertebrate and particularly the mammalian myocilin family are also within the scope of the invention. Preferably, a myocilin polypeptide has an amino acid sequence at least about 92% homologous and preferably at least about 95%, 96%, 97%, 98% or 99% homologous to the polypeptide represented in SEQ ID No: 8 or 10. In a preferred embodiment, the myocilin polypeptide is encoded by a nucleic acid which hybridizes with a nucleic acid sequence represented in one of SEQ ID No: 7 or 9. The subject myocilin proteins also include modified proteins, which are resistant to post-translational modification, as for example, due to mutations which alter modification sites (such as tyrosine, threonine, serine or aspargine residues), or which prevent glycosylation of the protein, or which prevent interaction of the protein with intracellular proteins involved in signal transduction.

The myocilin polypeptide can comprise a full length protein, such as represented in SEQ ID No: 8 or 10, or it can comprise a fragment corresponding to one or more particular motifs/domains, or to arbitrary sizes, e.g., at least 5, 10, 25, 50, 100, 150, 175, 200, 225, 250, 275, 300, 325, 350, 375, 400, 425, 450, 460, 470, 475, 480, 485, or 490 amino acids in length.

Another aspect of the invention features chimeric molecules (e.g. fusion proteins) comprised of a myocilin protein. For instance, the myocilin protein can be provided as a recombinant fusion protein which includes a second polypeptide portion, e.g., a second polypeptide having an amino acid sequence unrelated (heterologous) to the myocilin polypeptide (e.g. the second polypeptide portion is glutathione-S-transferase, an enzymatic activity such as alkaline phosphatase or an epitope tag).

Yet another aspect of the present invention concerns an immunogen comprising a myocilin polypeptide in an immunogenic preparation, the immunogen being capable of eliciting an immune response specific for a myocilin polypeptide; e.g. a humoral response, an antibody response and/or cellular response. In preferred embodiments, the immunogen comprises an antigenic determinant, e.g. a unique determinant, from the protein represented in SEQ ID Nos: 8 or 10.

A still further aspect of the present invention features antibodies and antibody preparations specifically reactive with an epitope of the myocilin protein. In preferred embodiments the antibody specifically binds to at least one epitope represented in SEQ ID Nos: 8 or 10.

The invention also features transgenic non-human animals which include (and preferably express) a heterologous form of a GLC1A gene described herein, or which misexpress an endogenous GLC1A gene (e.g., an animal in which expression of one or more of the subject GLC1A proteins is disrupted). Such a transgenic animal can serve as an animal model for studying cellular and tissue disorders comprising mutated or mis-expressed GLC1A alleles or for use in drug screening. Alternatively, such a transgenic animal can be useful for expressing recombinant myocilin polypeptides.

In yet another aspect, the invention provides assays, e.g., for screening test compounds to identify inhibitors, or alternatively, potentiators, of an interaction between a myocilin protein and, for example, a virus, an extracellular ligand of the myocilin protein, or an intracellular protein which binds to the myocilin protein.

A further aspect of the present invention provides a method of determining if a subject is at risk for glaucoma or another disorder resulting from a mutant GLC1A gene. The method includes detecting, in a tissue of the subject, the presence or absence of a genetic lesion characterized by at least one of (i) a mutation of a gene encoding a myocilin protein, (e.g., a gene represented in one of SEQ ID Nos: 7 or 9, or a homolog thereof or a mutation of a GLC1A intronic sequence, e.g. as represented in SEQ ID Nos. 1–6); or (ii) the mis-expression of a GLC1A gene. In preferred embodiments, detecting the genetic lesion includes ascertaining the existence of at least one of: a deletion of one or more nucleotides from a GLC1A gene; an addition of one or more nucleotides to the gene, a substitution of one or more nucleotides of the gene, a gross chromosomal rearrangement of the gene; an alteration in the level of a messenger RNA transcript of the gene (e.g., due to a promoter mutation); the presence of a non-wild type splicing pattern of a messenger RNA transcript of the gene; a non-wild type level of the protein; and/or an aberrant level of soluble myocilin protein.

For example, detecting the genetic lesion can include (i) providing a probe/primer comprised of an oligonucleotide which hybridizes to a sense or antisense sequence of a GLC1A gene or naturally occurring mutants thereof, or intronic flanking sequences naturally associated with the GLC1A gene; (ii) contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the GLC1A gene and, optionally, of the flanking nucleic acid sequences. For instance, the primer can be employed in a polymerase chain reaction (PCR) or in a ligation chain reaction (LCR). In alternate embodiments, the level of a GLC1A protein is detected in an immunoassay using an antibody which is specifically immunoreactive with the myocilin protein.

Other features and advantages of the invention will be apparent from the following detailed description and claims.

3. BRIEF DESCRIPTION OF THE FIGURES

Figure 1A-1:
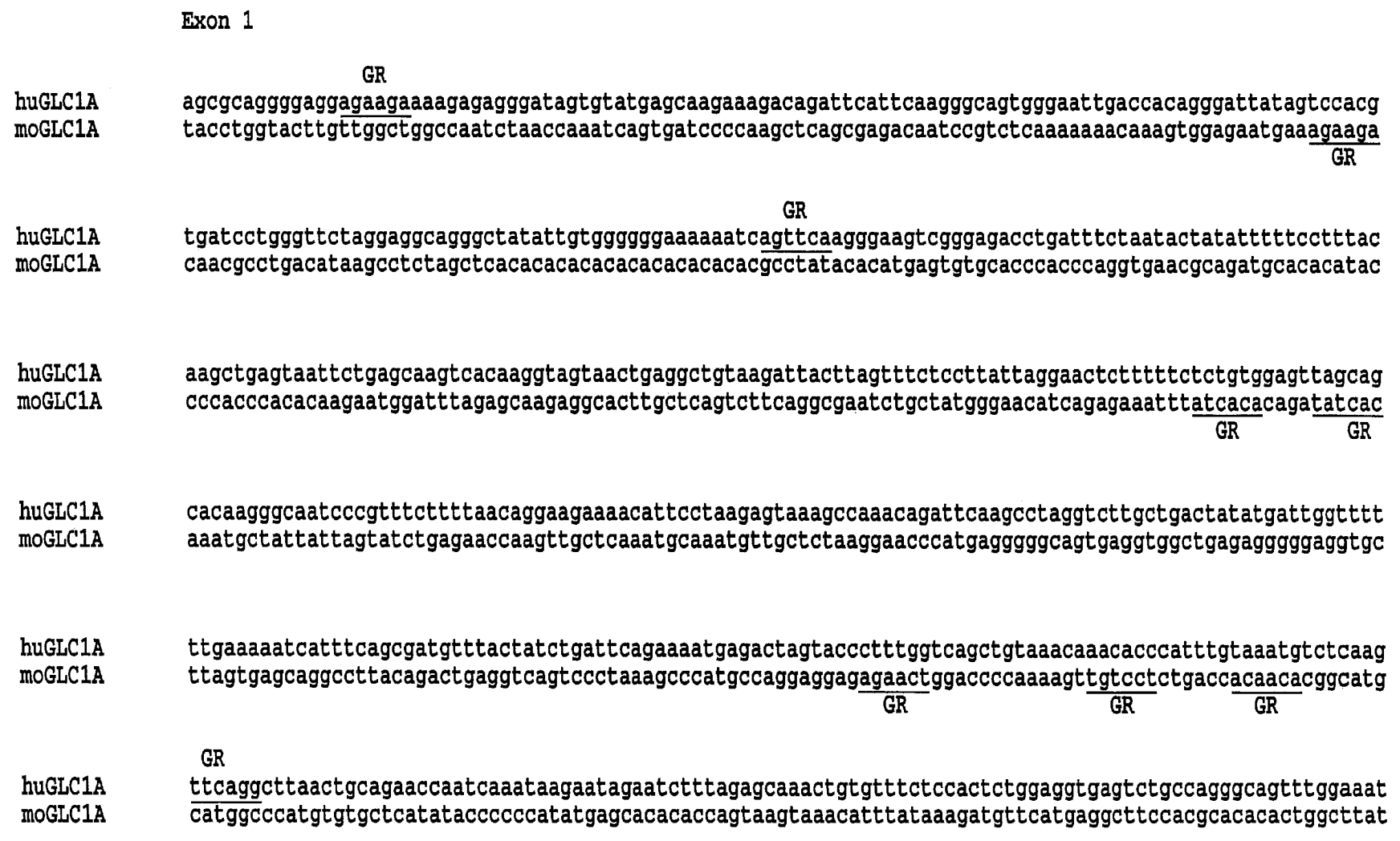
Figure 1A-2:
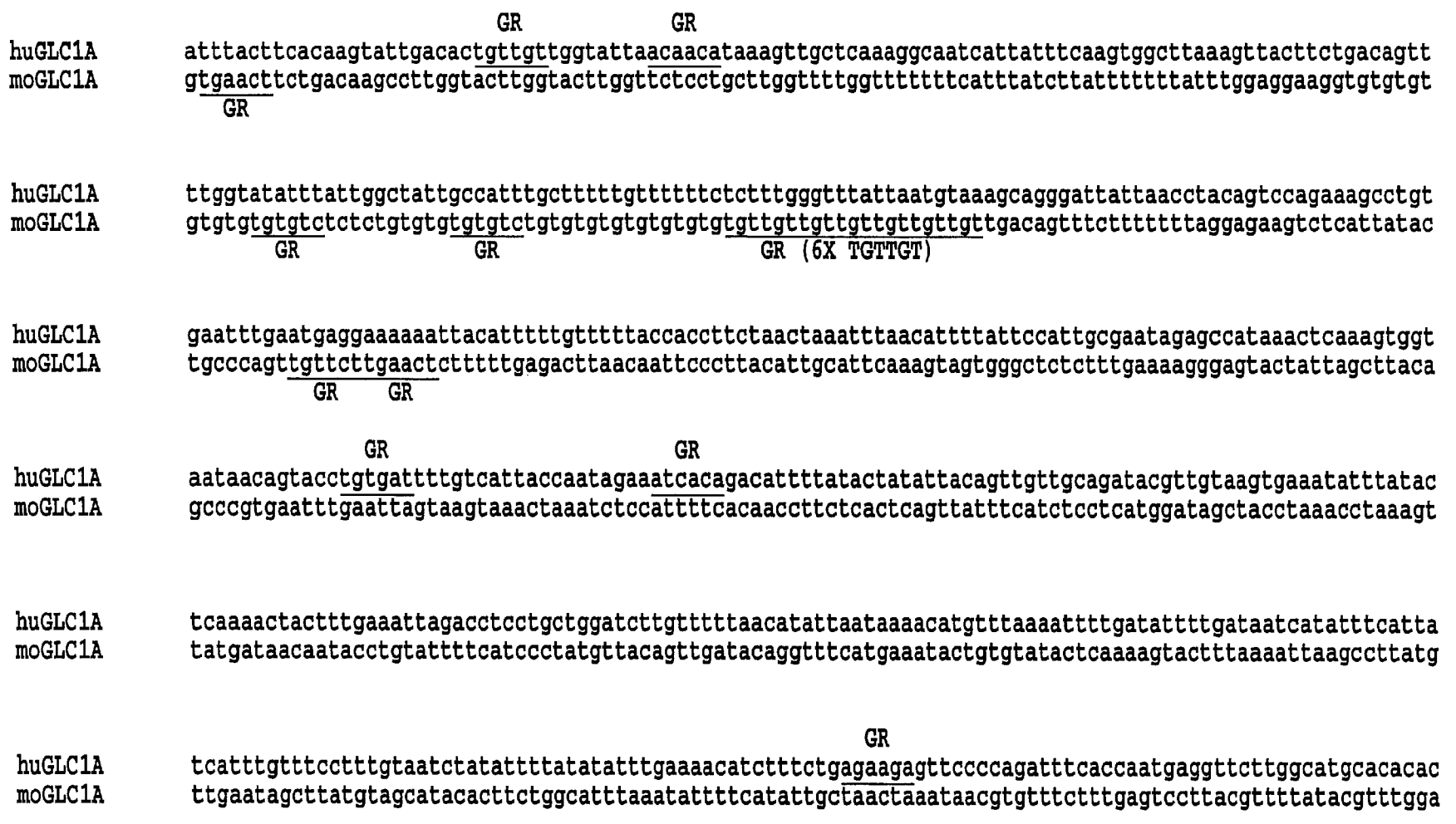
Figure 1A-4:
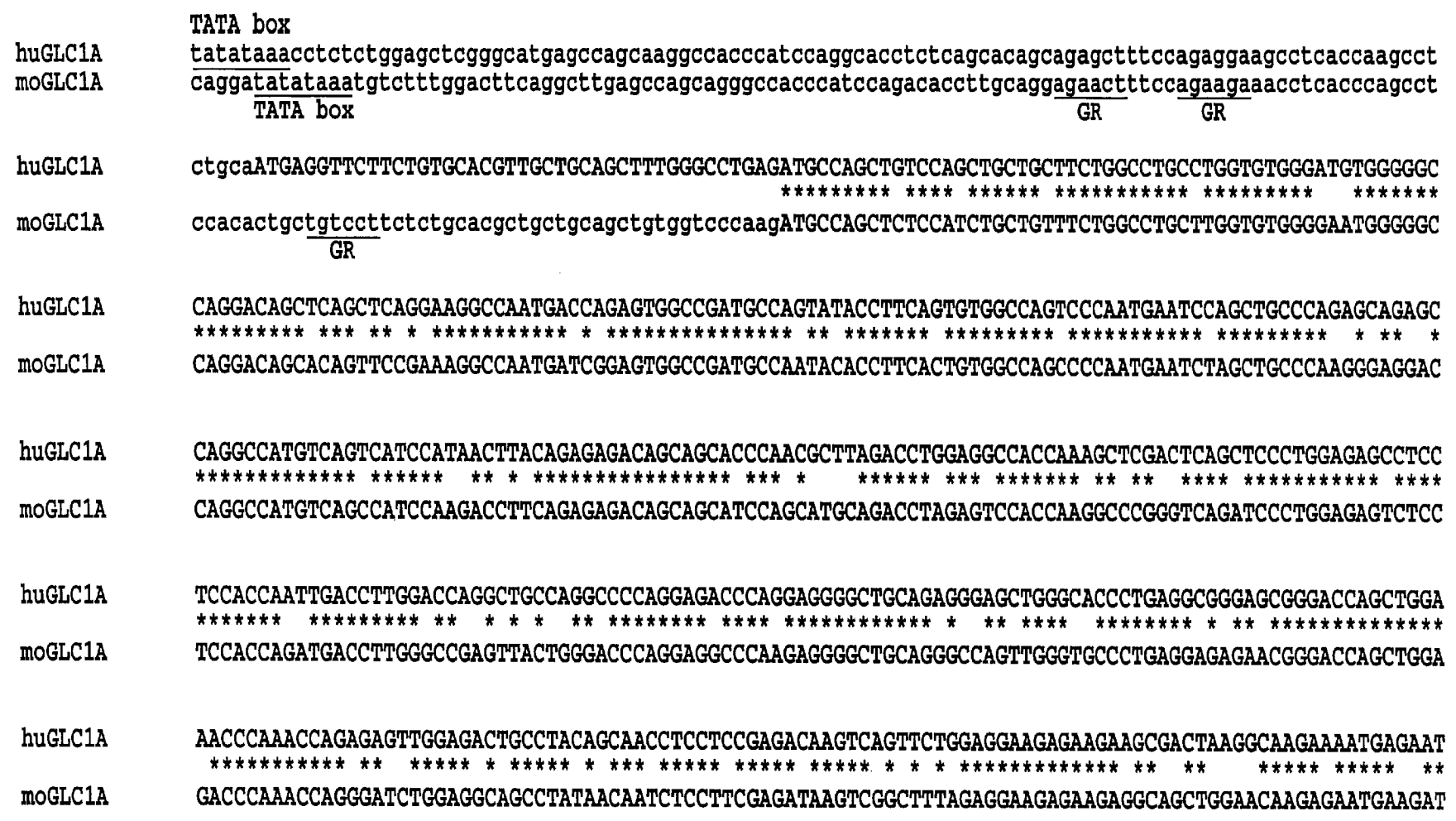

FIG. 1 is an alignment of human and mouse GLC1A gene sequences. The three exons of the human and mouse GLC1A genes and flanking sequences are aligned in panels A, B and C. These sequences are not continuous. Exon sequences are reported in capital letters while flanking sequences are in lower-case letters. Nucleotides conserved between mouse and human are indicated by a closed circle. In panel 1A, exon 1 and flanking promoter and intron 1 sequences are shown. A subset of putative promoter and enhancer elements are underlined and labeled. GRE half-sites are indicated by "GR". A (CA) repeat polymorphism in the 5' flanking region of the human GLC1A gene is also underlined and labeled "(CA) repeat polymorphism". In panel 1B, exon 2 and flanking intron 1 and intron 2 sequences are shown. In panel 1C, exon 3 and flanking intron 2 and downstream sequences are shown. Polyadenylation signal sequences are underlined and labeled "poly-A". A (CA) repeat polymorphism downstream of the human GLC1A gene is also underlined and labeled "(CA) repeat polymorphism".

FIG. 2 is a schematic representation of putative motifs that are conserved between human and mouse myocilin proteins.

FIG. 3 is an alignment of the proteins predicted by the mouse and human GLC1A genes. Amino acids conserved between mouse and human are indicated by a closed circle. The location of disease-causing mutations previously identified in the human GLC1A gene are indicated. For each missense mutation, the mutant residue is shown directly above the wild-type amino acid. The location of a nonsense mutation is indicated by a "1" and the location of an insertion mutation is indicated by a "2".

4. DETAILED DESCRIPTION OF THE INVENTION

4.1. General

As reported herein, a genetic locus associated with JOAG was identified on chromosome 1q21-q31 by genetic linkage analysis. Observed recombinations between the glaucoma phenotype and highly polymorphic genetic markers in two large JOAG kindreds allowed the interval containing GLC1A gene to be narrowed to a 3 cM region of chromosome 1q between markers D1S3665 and D1S3664. Further evaluation of marker haplotypes revealed that each of three pairs of glaucoma families shared alleles of the same eight contiguous markers suggesting that the GLC1A gene lies within a narrower interval defined by D1S1619 and D1S3664.

Several genes mapping to the GLC1A region of chromosome 1 were considered as candidates for the disease-causing gene. Three genes (LAMC1 (H. C. Watkins et. al., (1993) *Hum. Mol. Genet.* 2: 1084), NPRI (D. G. Lowe et al., (1990) *Genomics* 8:304), and CNR2 (S. Munro et al., (1993) *Nature* 365:61), were excluded from the candidate region by genetic linkage analysis using intragenic polymorphic markers. Five additional candidate genes were determined to lie within the observed recombinant interval by YAC STS content mapping: selectin E (M. P. Bevilacqua et al., (1989) *Science* 243:1160) (GenBank accession no. M24736); selectin L (T. F. Tedder et al., (1989) *J. Exp. Med.* 170:123) (GenBank accession no. M25280); TXGP-1 (S. Miura et al., (1991) *Mol. Cell Biol* 11:1313) (GenBank accession no. MD90224; APT1LG1 (T. Takahashi et al., (1994) *Int. Immunol.* 6, 1567); and TIGR (Trabecular meshwork Induced Glucocorticoid Response Protein) (J. R. Polansky et al., (1989) *Prog. Clin. Biol. Res* 12:113; J. Escribano et al., (1995) *J. Biochem.* 118:921; International Patent Application Publication No. WO 96/14411) (GenBank accession nos. R95491, R95447, R95443, R47209). However, two of these genes (selectin E, and selectin L) were found to lie outside of the shared haplotype interval with this approach. The remaining genes (APT1LG1, TXGP-1, and TIGR) were found to map within the narrowest JOAG interval by both YAC STS content and radiation hybrid mapping.

Two of these genes (APT1LG1 and TIGR) were screened for mutations in families with JOAG. Primers were selected from the available sequence (T. Takahashi et al., (1994) *Int. Immunol.* 6, 1567, J. Escribano et al., (1995) *J. Biochem.* 118:921; International Patent Application Publication No. WO 96/14411) (GenBank accession nos. R95491, R95447, R95443, R47209) and overlapping PCR amplification products were evaluated by single strand conformation polymorphism analysis (B. J. Bassam et al., (1991) *Anal. Biochem.* 196: 80) and direct DNA sequencing. Although the complete cDNA sequence of the APT1LG1 and TIGR genes have been published, the presence of intervening sequences permitted only 85–90% of their coding sequences to be screened in genomic DNA. Eight unrelated JOAG patients were screened with the APT1LG1 assay but no sequence variants were identified.

The TIGR gene assay was initially used to screen affected members of four different 1q-linked glaucoma families, and affected members of four smaller families implicated by haplotypic data. Amino-acid-altering mutations were detected in four of eight families. A tyrosine to histidine mutation in codon 437 was detected in all 22 affected members of the original family (V. C. Sheffield et al., (1993) *Nature Genet.* 4:47) linked to 1q. A glycine to valine mutation in codon 364 was detected in two families including one previously unreported adult-onset open angle glaucoma family with 15 affected members. A nonsense mutation (glutamine to stop) at codon 368 was detected in two families. The latter mutation would be expected to result in a truncation of the gene product.

The prevalence of mutations in the two PCR amplimers that harbored these three changes was then estimated by screening four different populations: glaucoma patients with a family history of the disease; unselected primary open angle glaucoma probands seen in a single clinic; the general population (approximated by patients with heritable retinal disease and spouses from families who participated in prior linkage studies); and, unrelated volunteers over the age of 40 with normal intraocular pressures and no personal or family history of glaucoma. PCR products determined to contain a sequence variation by SSCP were sequenced and compared to sequence generated from an unaffected individual as well as the normal chromosome in each affected individual. Overall, missense or nonsense mutations were found in about 3–5% of unrelated glaucoma patients and in about 0.2% of controls. A Chi-square test revealed this difference to be significant ($p<0.001$).

In a subsequent study, SSCP screening followed by sequencing of DNA from 1312 unrelated individuals revealed a total of 33 GLC1A sequence changes. Sequencing of the entire GLC1A coding region amplified from the probands of three families with 1q-linked glaucoma, but without SSCP shifts revealed three additional sequence changes. Sixteen of these 36 sequence variations (Table 1) met the following criteria for a "probable" disease causing mutation: 1) presence in one or more glaucoma patients; 2) alteration of the predicted amino acid sequence; 3) presence in less than 1% of the general population; 4) absence in the 91 normal volunteers. These sixteen mutations were found in 34 of the 716 glaucoma probands (4.7%). Ten sequence changes failed to alter the predicted amino acid sequence of GLC1A and are therefore likely to be non-disease-causing polymorphisms (Table 3). Nine sequence changes altered the predicted amino acid sequence of GLC1A (eight) or the 5' flanking region (one) but were judged likely to be non-disease-causing polymorphisms (Table 2) for one of the following reasons: they were present in more than 1% of the general population (three), they were found only in the normal or general population (five), or they were found in the same allele as a more likely disease-causing mutation (one).

TABLE 1

| Probable Mutations |
| --- |
| 1) GLN19HIS |
| 2) ARG82CYS |
| 3) TRP286ARG |
| 4) THR293LYS |
| 5) PRO361SER |
| 6) GLY364VAL |
| 7) GLN368STOP |
| 8) THR377MET |
| 9) ASP380GLY |
| 10) 396INS397 |
| 11) ARG422HIS |
| 12) TYR437HIS |
| 13) ALA445VAL |
| 14) ARG470CYS |
| 15) ILE477ASN |
| 16) LYS500ARG |

TABLE 2

| Probable Polymorphism |
| --- |
| 1) GLU352LYS |
| 2) CYS9SER |
| 3) ASN73SER |
| 4) ARG76LYS |
| 5) LYS398ARG |
| 6) ARG422CYS |
| 7) SER425PRO |
| 8) TYR473CYS |
| 9) VAL495ILE7 |

TABLE 3

Third Nucleotide (Wobble) Polymorphisms

1) PRO13PRO
2) GLY122GLY
3) LEU159LEU
4) LYS266LYS
5) THR285THR
6) THR325THR
7) VAL329VAL
8) TYR347TYR
9) GLU396GLU
10) VAL439VAL

Bacterial artificial chromosomes (BACs) containing the human GLC1A gene and its mouse orthologue were subcloned and sequenced to reveal the genomic structure of the genes. Both the human and mouse GLC1A genes are composed of three exons. Human exon 1 (including the 5' promoter region of exon 1, base pairs 1–1905; exon 1, base pairs 1906–2509; and the 5' end of intron 1, base pairs 2510–2800) is set forth as SEQ ID No: 1. Human exon 2 (including the 3' end of intron 1, base pairs 1–193; exon 2, base pairs 194–319; and the 5' end of intron 2, base pairs 320–680) is set forth as SEQ ID No:2. Human exon 3 (including the 3' end of intron 2, base pairs 1–427; exon 3, base pairs 428–1212; and the 3' UTR, base pairs 1213–2000) is set forth as SEQ ID No:3. Mouse exon 1 (including the 5' promoter region of exon 1; base pairs 1–1947; exon 1, base pairs 1948–2509; and the 5' end of intron 1, base pairs 2510–2800) is set forth as SEQ ID No:4. Mouse exon 2 (including the 3' end of intron 1, base pairs 1–193; exon 2, base pairs 194–319; and the 5' end of intron 2, base pairs 320–680) is set forth as SEQ ID No:5 and mouse exon 3 (including the 3' end of intron 2, base pairs 1–427; exon 3, base pairs 428–1212 and the 3' UTR, base pairs 1213–1456) is set forth as SEQ ID No:6. Exons two and three are 126 base pairs and 782 base pairs long in both genes, while exon one is 604 base pairs in the human gene and 562 base pairs in the mouse gene. Exon-intron borders are completely conserved between mouse and human. The human coding GLC1A nucleotide sequence is comprised of 1512 nucleotides (SEQ ID No: 7) and encodes a 504 amino acid myocilin protein (SEQ ID NO. 8) having a molecular weight of about 57 kDa. The mouse coding GLC1A nucleotide sequence is comprised of 1470 nucleotides (SEQ ID No: 9) and encodes a 490 amino acid myocilin protein (SEQ ID No: 10) having a molecular weight of about 55 kDa. The human and mouse coding sequences are 83% identical at the nucleotide level and predict proteins that are 82% identical at the amino acid level.

Many putative transcription regulatory sequences were identified in the upstream region of the GLC1A genes (Table 4). Three poly-adenylation sites were located in the 3' UTR of the human gene at positions 1714, 1864 and 2006 base pairs following the putative start codon. Additionally the human GLC1A gene was found to be closely flanked by two CA simple tandem repeat polymorphisms (STRPs) that proved to be useful genetic markers for tracing the segregation of the gene within families.

TABLE 4

Putative GLCIA promoter and enhancer elements

| Human and Mouse | Human only | Mouse only |
|---|---|---|
| AP-1 | AFP1 | DTF-1 |
| AP-2 | CF2-II | GATA-2 |
| AP-3 | CP2 | Hb |
| AR | DBP | Lva |
| c-ETS | Elk-1 | Lvb-binding factor |
| c-Myc | G6 Factor | MAF |
| C/EBP | HNF-1 | MAZ |
| CAC-binding protein | HOX-D8 | muEBP-C2 |
| Dr | HOX-D9 | NF-E2 |
| En | HOX-10 | PTFI-beta |
| F2F | IRF | TF3-s |
| GATA-1 | LyF-1 | USF |
| GFII | MBF-1 | |
| GR | MCBF | |
| HiNF-A | Myogenin | |
| HNF-3 | NF-InsE | |
| MBF-l | TCF-2alpha | |
| MEP-1 | TDEF | |
| NF-1 | TGT3 | |
| NF-GMb | TII | |
| N-Oct-3 | UBP-1 | |
| Oct | WT-1 | |
| PEA3 | Pit-1a | |
| PPAR | | |
| PR | | |
| PU.1 | | |
| PuF | | |
| Sp1 | | |
| SRY | | |
| TCF-lA | | |
| TFIIB | | |
| TFIIE | | |
| TFIIF | | |
| TMF | | |
| YY1 | | |
| Zeste | | |

The human GLC1A gene has been placed on the chromosome 1 physical map between four flanking genes (SELL, SELE, GLC1A, APT1LG1, AT3). The mouse homologs of these flanking genes are present in the same order on the mouse chromosome 1, suggesting that the mouse GLC1A gene is located in this syntenic region between the mouse homologues of SELE and APT1LG1.

The expression of human GLC1A was examined by Northern blot analysis of RNA from adult tissues. High levels of expression of the 2.3 kb mRNA was found in a wide range of tissues including: heart, skeletal muscle, stomach, thyroid, trachea, bone marrow, thymus, prostate, small intestine and colon. Less abundant GLC1A expression was observed in lung, pancreas, testis, ovary, spinal cord, lymph node and adrenal gland. GLC1A transcripts were not detected in brain, placenta, liver, kidney, spleen or leukocytes. A similar expression pattern was observed in the mouse. To test the possibility that certain regions of the brain were under represented in poly-A selected mRNA of total brain tissue, a Northern blot prepared with RNA from several different regions of the brain were hybridized using a GLC1A probe. Hybridization was observed in the spinal cord, but not in the cerebellum, cerebral cortex, medulla, occipital lobe, frontal lobe, temporal lobe, or putamen.

FIG. 2 illustrates protein motifs that are present in both human and mouse GLC1A proteins. Both the GLC1A nucleic acid sequence and encoded myocilin amino acid sequence show homology to nonmuscle myosin in the N-terminal region and to olfactomedin in the C-terminal region. In addition, both human and mouse GLC1A proteins contain a leucine zipper domain similar to that seen in kinectin and other cytoskeletal proteins in the myosin-like domain (spanning amino acids 71–152). This motif consists of two subregions spanning amino acids 71–85 and 103–152 in which leucine residues appear three to eight times at every seventh position. Both the human and the mouse GLC1A nucleic acids include 10 putative phosphorylation sites and 4 putative glycosylation sites. In addition to these functional domains, a hydrophobic domain appears at the N-terminus of the myocilin protein and includes a sequence resembling a signal peptide in which the alanine residue at position 18 may be a possible cleavage site.

Further analysis reveals a hydrophobic region between amino acids 17–37 and 426–44. However, the length and degree of hydrophobicity of these domains suggests that they are not membrane spanning. The carboxy-terminal three amino acids of human GLC1A protein are serine, lysine and methionine. This sequence has been shown to function as a peroxisome targeting sequence in other proteins (Subramani, S (1993) *Ann. Rev. of Cell Bio.* 9:445–478). However, no such putative targeting sequence is present in the mouse protein. Western blot analysis of human GLC1A protein reveals bands at 57 and 59 kD, confirming the predicted protein size and providing evidence that the protein may be glycosylated. These findings suggest that myocilin is a novel cytoskeletal protein involved in the development of neuroepithelium, such as photoreceptor cells.

FIG. 3 shows an alignment of the predicted amino acid sequence for the mouse and human GLC1A genes and indicates the position of sixteen mutations with respect to the mouse and human GLC1A protein seqeuences. Fourteen of these mutations are missense mutations that result in single amino acid substitutions. Twelve of these occur at amino acids that are conserved between human and mouse while two occur at amino acids that are not conserved. The two remaining mutations include an insertion that disrupts two conserved amino acids and a nonsense mutation that results in the truncation of the terminal 136 amino acids of the GLC1A protein and the loss of 121 conserved residues. Thus, the percentage of disease causing mutations found in amino acids conserved between mouse and human (88%) is not significantly different from the overall protein conservation across species (82%).

Importantly, the GLC1A nucleic acid sequence differs substantially from the TIGR gene sequence reported in International Patent Application No. WO 96/14411 (GenBank accession nos. R95491, R95447, R95443 and R947209). In fact, as reported, the TIGR gene sequence does not encode a functional protein.

A summary of the differences between the GLC1A gene disclosed herein, and the TIGR gene are presented in Table 5.

TABLE 5

Differences Between GLC1A and TIGR Gene Sequences

1. The "C" at bp #331 of the GLC1A DNA coding sequence is not present in the TIGR sequence.
2. The 29 bps "AGGGGCTGCAGAGGGAGCTGGGCACCCTG" (SEQ ID NO. 11) at bp #344-372 ofthe GLG1A DNA coding sequence are not included in the TIGR sequence.
   Errors 1 and 2 cause the TIGR sequence to wrongly predict 4 amino acids and exclude 10 amino acids from the protein sequence.

TABLE 5-continued

Differences Between GLC1A and TIGR Gene Sequences

3. The "C" at bp #559 of the GLC1A DNA coding sequence is not present in the TIGR sequence.
4. A "T" is wrongly inserted between bp #560 and #561 of the GLC1A DNA coding sequence in the TIGR sequence.
   Errors 3 and 4 cause the TIGR sequence to incorrectly predict a serine amino acid at residue #187 instead of a glutamine.
5. The 9 bps "CTCAGGAGT" present at bps 706-714 of the GLC1A DNA coding sequence are wrongly duplicated and inserted between bp 714 and 715 in the TIGR sequence.
   Consequently, the TIGR DNA sequence incorrectly predicts that 3 amino acids are inserted into the GLC1A protein sequence.
6. A "T" is incorrectly inserted between bp #841 and #842 of the GLC1A DNA coding sequence in the TIGR sequence.
7. The "G" at bp #891 of the GLC1A DNA coding sequence is not present in the TIGR sequence.
   Errors 6 and 7 cause 17 amino acids predicted by the GLC1A DNA coding sequence to be out of frame in the TIGR sequence.
8. A "G" at bp #979 of the GLC1A DNA coding sequence is replaced with a "C" in the TIGR sequence.
9. A "C" at bp #980 of the GLC1A DNA coding sequence is replaced with a "G" in the TIGR sequence.
   Errors 8. and 9. cause the TIGR sequence to wrongly predict an arginine amino acid at residue #327 instead of an alanine.

The above 9 errors in the TIGR GLC1A sequence result in 45 nucleotide differences that cause 42 incorrect amino acid predictions. Therefore the human TIGR amino acid sequence is only about 91.67% identical to the human myocilin protein sequence and the human TIGR gene sequence is only about 97% identical to the human GLC1A sequence.

The identification of this disease gene increases the understanding of the pathophysiology of glaucoma, which in turn facilitates the development of assays for identifying molecules that modulate (e.g. agonize or antagonize) the bioactivity of a functional or mutant TIGR gene or protein. A therapeutically effective amount of these molecules can be administered to a subject with glaucoma or at risk for developing glaucoma to prevent or reduce the severity of the condition.

In addition, the establishment of the disease-causing nature of each GLC1A sequence variant and the associated penetrance and age of onset, as set forth herein, enables a clinician to provide patients, who harbor a particular sequence change, with useful information regarding their risk of developing glaucoma.

4.2 Definitions

For convenience, the meaning of certain terms and phrases employed in the specification, examples, and appended claims are provided below.

The term "agonist", as used herein, is meant to refer to an agent (e.g., a myocilin therapeutic) that directly or indirectly enhances, supplements or potentiates a wildtype or mutant myocilin bioactivity.

The term "antagonist", as used herein, is meant to refer to an agent (e.g. a myocilin therapeutic) that directly or indirectly prevents, minimizes or suppresses a wildtype or mutant myocilin bioactivity.

"Cells", "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the proteins. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-myocilin-Y, wherein myocilin represents at least a portion of the protein which is derived from one of the myocilin proteins, and X and Y are independently absent or represent amino acid sequences which are not related to one of the myocilin sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a myocilin polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the polypeptides of the present invention, including both exon and (optionally) intron sequences. A "recombinant gene" refers to nucleic acid encoding a myocilin polypeptide and comprising GLC1A-encoding exon sequences, though it may optionally include intron sequences which are either derived from a chromosomal GLC1A gene or from an unrelated chromosomal gene. Exemplary recombinant genes encoding the subject myocilin polypeptides are represented in SEQ ID NO 7 and 9. The term "intron" refers to a DNA sequence present in a given GLC1A gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the GLC1A sequences of the present invention.

The term "interact" as used herein is meant to include detectable interactions between molecules, such as can be detected using, for example, a yeast two hybrid assay. The term interact is also meant to include "binding" interactions between molecules. Interactions may, for example, be protein-protein or protein-nucleic acid in nature.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject GLC1A polypeptides preferably includes no more than 10 kilobases (kb) of nucleic acid sequence which naturally immediately flanks the GLC1A gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, (i.e., activation or stimulation), for example by agonizing; and downregulation, (i.e. inhibition or suppression) for example by antagonizing a myocilin bioactivity.

A "'myocilin bioactivity', 'biological activity' or 'activity'" is meant to refer to a cytoskeletal or antigenic function that is directly or indirectly preformed by a myocilin polypeptide (whether in its native or denatured conformation), or by any subsequence thereof. Cytoskeletal functions include processes involved with the development or structure of ciliated neuroepithelium (e.g. comprising photoreceptor cells). Antigenic functions include possession of an epitope or antigenic site that is capable of cross-reacting with antibodies raised against a naturally occurring or denatured myocilin polypeptide or fragment thereof The "non-human animals" of the invention include mammals such as rodents, non-human primates, sheep, dog, cow, chickens, amphibians, reptiles, etc. Preferred non-human animals are selected from the rodent family including rat and mouse, most preferably mouse, though transgenic amphibians, such as members of the Xenopus genus, and transgenic chickens can also provide important tools for understanding and identifying agents which can affect, for example, embryogenesis and tissue formation. The term "chimeric animal" is used herein to refer to animals in which the recombinant gene is found, or in which the recombinant gene is expressed in some but not all cells of the animal. The term "tissue-specific chimeric animal" indicates that one of the recombinant GLC1A genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a myocilin polypeptide is inserted into a suitable expression vector which is in turn used to transform a host cell to produce the heterologous protein. Moreover, the phrase "derived from", with respect to a recombinant GLC1A gene, is meant to include within the meaning of "recombinant protein" those proteins having an amino acid sequence of a native myocilin protein, or an amino acid sequence similar thereto which is generated by mutations including substitutions and deletions (including truncation) of a naturally occurring form of the protein.

"Small molecule" as used herein, is meant to refer to a composition, which has a molecular weight of less than about 5 kD and most preferably less than about 4 kD. Small molecules can be nucleic acids, peptides, polypeptides, peptidometics, carbohydrates, lipids or other organic carbon containing or inorganic molecules. Extensive libraries of chemical or biological (e.g., fungal, bacterial or algal extracts) mixtures are available for screening with the assays of the invention.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400, 450, 500, 550, 600, 650, 700, 750, 800, 850, 900, 950, 1000, 1050, 1100, 1150, 1200, 1250, 1300, 1350, 1400, 1450, 1460, 1470, 1480, 1490 consecutive nucleotides of a vertebrate, preferably GLC1A gene, such as a GLC1A sequence designated in one of SEQ ID Nos: 7 or 9, or a sequence complementary thereto, or naturally occurring mutants thereof, such that it shows at least 10 times more hybridization, preferably at least 50 times more hybridization, and even more preferably at least 100 times more hybridization than it does to a cellular nucleic acid (e.g., mRNA or genomic DNA) encoding a protein other than a vertebrate GLC1A protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant GLC1A genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of myocilin proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a mammalian myocilin polypeptide or, in the case of anti-sense expression from the transferred gene, the expression of a naturally-occurring form of the myocilin protein is disrupted.

As used herein, the term "transgene" means a nucleic acid sequence (encoding, e.g., one of the mammalian myocilin polypeptides, or pending an antisense transcript thereto), which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the GLC1A proteins, e.g. either agonistic or antagonistic forms. However, transgenic animals in which the recombinant GLC1A gene is silent are also contemplated, as for example, the FLP or CRE recombinase dependent constructs described below. Moreover, "transgenic animal" also includes those recombinant animals in which gene disruption of one or more GLC1A genes is caused by human intervention, including both recombination and antisense techniques.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

4.3 Nucleic Acids of the Present Invention

As described below, one aspect of the invention pertains to isolated nucleic acids comprising nucleotide sequences encoding myocilin polypeptides, and/or equivalents of such nucleic acids. The term equivalent is understood to include nucleotide sequences encoding functionally equivalent myocilin polypeptides or functionally equivalent peptides having an activity of a vertebrate myocilin protein such as described herein. Equivalent nucleotide sequences will include sequences that differ by one or more nucleotide substitutions, additions or deletions, such as allelic variants; and will, therefore, include sequences that differ from the nucleotide sequence of the GLC1A gene shown in SEQ ID Nos: 7 or 9 due to the degeneracy of the genetic code.

Preferred nucleic acids are vertebrate GLC1A nucleic acids. Particularly preferred vertebrate GLC1A nucleic acids are mammalian. Regardless of species, particularly preferred GLC1A nucleic acids encode polypeptides that are at least 90% similar to an amino acid sequence of human GLC1A. Preferred nucleic acids encode a GLC1A polypeptide comprising an amino acid sequence at least 90% homologous and more preferably 94% homologous with an amino acid sequence of a vertebrate GLC1A, e.g., such as a sequence shown in one of SEQ ID Nos: 8 or 10. Nucleic acids which encode polypeptides at least about 95%, and even more preferably at least about 98–99% similarity with an amino acid sequence represented in SEQ ID Nos.: 8 or 10 are also within the scope of the invention. In a particularly preferred embodiment, the nucleic acid of the present invention encodes an amino acid GLC1A sequence shown in one of SEQ ID No: 8 or 10. In one embodiment, the nucleic acid is a cDNA encoding a peptide having at least one bioactivity of the subject GLC1A polypeptide. Preferably, the nucleic acid includes all or a portion of the nucleotide sequence corresponding to the coding region of SEQ ID Nos: 1–7 or 9.

Still other preferred nucleic acids of the present invention encode a GLC1A polypeptide which includes a polypeptide sequence corresponding to all or a portion of amino acid residues of SEQ ID Nos: 8 or 10, e.g., at least 2, 5, 10, 25, 50, 100, 150 or 200 amino acid residues of that region. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 200, 250, 300, 350, 400, 410, 420, 430, 435 or 440 base pairs.

Another aspect of the invention provides a nucleic acid which hybridizes to a nucleic acid represented by one of SEQ ID Nos: 1–7 or 9. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a GLC1A nucleic acid of the present invention will bind to one of SEQ ID Nos 1 or 2 under moderately stringent conditions, for example at about 2.0×SSC and about 40° C. In a particularly preferred embodiment, a GLC1A nucleic acid of the present invention will bind to one of SEQ ID Nos: 1–7 or 9 under high stringency conditions.

Preferred nucleic acids have a sequence at least about 75% homologous and more preferably 80% and even more preferably at least about 85% homologous with an amino acid sequence of a mammalian GLC1A, e.g., such as a sequence shown in one of SEQ ID Nos: 8 and 10. Nucleic acids at least about 90%, more preferably about 95%, and most preferably at least about 98–99% homologous with a nucleic sequence represented in one of SEQ ID Nos: 8 and 10 are of course also within the scope of the invention. In preferred embodiments, the nucleic acid is a mammalian GLC1A gene and in particularly preferred embodiments, includes all or a portion of the nucleotide sequence corresponding to the coding region of one of SEQ ID Nos: 1–7 or 9.

Nucleic acids having a sequence that differs from the nucleotide sequences shown in one of SEQ ID Nos: 1–7 or 9 due to degeneracy in the genetic code are also within the scope of the invention. Such nucleic acids encode functionally equivalent peptides (i.e., a peptide having a biological activity of a myocilin polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a myocilin polypeptide. However, it is expected that DNA sequence polymorphisms that do lead to changes in the amino acid sequences of the subject myocilin polypeptides will exist among mammalians. One skilled in the art will appreciate that these variations in one or more nucleotides (e.g., up to about 3–5% of the nucleotides) of the nucleic acids encoding polypeptides having an activity of a mammalian myocilin polypeptide may exist among individuals of a given species due to natural allelic variation.

As indicated by the examples set out below, myocilin protein-encoding nucleic acids can be obtained from mRNA present in any of a number of eukaryotic cells. It should also be possible to obtain nucleic acids encoding mammalian myocilin polypeptides of the present invention from genomic DNA from both adults and embryos. For example, a gene encoding a myocilin protein can be cloned from either a cDNA or a genomic library in accordance with protocols described herein, as well as those generally known to persons skilled in the art. Examples of tissues and/or libraries suitable for isolation of the subject nucleic acids include photoreceptor cells of the retina, among others. A cDNA encoding a myocilin protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a mammalian myocilin protein can also be cloned using established polymerase chain reaction techniques in accordance with the nucleotide sequence information provided by the invention. The nucleic acid of the invention can be DNA or RNA. A preferred nucleic acid is a cDNA represented by a sequence selected from the group consisting of SEQ ID Nos: 1 and 2.

4.3.1. Vectors.

This invention also provides expression vectors containing a nucleic acid encoding a myocilin polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject mammalian myocilin proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject myocilin polypeptide, or alternatively, encoding a peptide which is an antagonistic form of the myocilin protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject myocilin proteins. Thus, another aspect of the invention features expression vectors for in vivo or in vitro transfection and expression of a myocilin polypeptide in particular cell types so as to reconstitute the function of, or alternatively, abrogate the function of myocilin-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject myocilin polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject myocilin polypeptide gene by the targeted cell. Exemplary targeting means of this type include liposomal derived systems, poly-lysine conjugates, and artificial viral envelopes.

4.3.2. Probes and Primers

Moreover, the nucleotide sequences determined from the cloning of GLC1A genes from mammalian organisms will further allow for the generation of probes and primers designed for use in identifying and/or cloning homologs in other cell types, e.g. from other tissues, as well as homologs from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID Nos: 1–7 or 9, or naturally occurring mutants thereof. For instance, primers based on the nucleic acid represented in SEQ ID Nos: 1–7 or 9 can be used in PCR reactions to clone homologs. Preferred primer pairs of the invention are set forth as SEQ ID Nos. 12 and 13; 14 and 15; 16 and 17; 18 and 19; 20 and 21; 22 and 23; 24 and 25; 26 and 27; 28 and 29; 30 and 31; 32 and 33; 34 and 35; 36 and 37; 38 and 39; 40 and 41; 42 and 43; 44 and 45; and 46 and 47.

Likewise, probes based on the subject GLC1A sequences can be used to detect transcripts or genomic sequences encoding the same or homologous proteins. In preferred embodiments, the probe further comprises a label group attached thereto and able to be detected, e.g. the label group can be selected from amongst radioisotopes, fluorescent compounds, enzymes, and enzyme co-factors, etc.

As discussed in more detail below, such probes can also be used as a part of a diagnostic test kit for identifying cells or tissue which misexpress a myocilin protein, such as by measuring a level of a myocilin-encoding nucleic acid in a sample of cells from a patient; e.g. detecting GLC1A mRNA levels or determining whether a genomic GLC1A gene has been mutated or deleted. Briefly, nucleotide probes can be generated from the subject GLC1A genes which facilitate histological screening of intact tissue and tissue samples for the presence (or absence) of myocilin-encoding transcripts. Similar to the diagnostic uses of anti-myocilin antibodies, the use of probes directed to GLC1A messages, or to genomic GLC1A sequences, can be used for both predictive and therapeutic evaluation of subjects. Used in conjunction with immunoassays as described herein, the oligonucleotide probes can help facilitate the determination of the molecular basis for a developmental disorder which may involve some abnormality associated with expression (or lack thereof) of a myocilin protein. For instance, variation in polypeptide synthesis can be differentiated from a mutation in a coding sequence.

4.3.3. Antisense, Ribozyme and Triplex Techniques

One aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject GLC1A proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a myocilin protein. Alternatively, the antisense construct is an oligonucleotide probe which is generated ex vivo and which, when introduced into the cell causes inhibition of expression by hybridizing with the mRNA and/or genomic sequences of a GLC1A gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions of the GLC1A nucleotide sequence of interest, are preferred.

Antisense approaches involve the design of oligonucleotides (either DNA or RNA) that are complementary to GLC1A mRNA. The antisense oligonucleotides will bind to the GLC1A mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. 1994. *Nature* 372:333). Therefore, oligonucleotides complementary to either the 5' or 3' untranslated, non-coding regions of a GLC1A gene could be used in an antisense approach to inhibit translation of endogenous GLC1A mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of GLC1A mRNA, antisense nucleic acids should be at least six nucleotides in length, and are preferably oligonucleotides ranging from 6 to about 50 nucleotides in length. In certain embodiments, the oligonucleotide is at least 10 nucleotides, at least 17 nucleotides, at least 25 nucleotides, or at least 50 nucleotides.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al., 1988, *BioTechniques* 6:958–976) or intercalating agents. (See, e.g., Zon, 1988, *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof In yet another embodiment, the antisense oligonucleotide is an α-anomeric oligonucleotide. An α-anomeric oligonucleotide forms specific double-stranded hybrids with complementary RNA in which, contrary to the usual conformation, the strands run parallel to each other (Gautier et al., 1987, *Nucl. Acids Res.* 15:6625–6641). The oligonucleotide is a 2'-O-methylribonucleotide (Inoue et al., 1987, *Nucl. Acids Res.* 15:6131–6148), or a chimeric RNA-DNA analogue (Inoue et al., 1987, *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nuci. Acids Res.* 16:3209), methylphosphonate oligonucleotides can be prepared by use of controlled pore glass polymer supports (Sarin et al., 1988, *Proc. Natl. Acad. Sci. U.S.A.* 85:7448–7451), etc.

While antisense nucleotides complementary to the GLC1A coding region sequence could be used, those complementary to the transcribed untranslated region are most preferred.

The antisense molecules should be delivered to cells which express the myocilin in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous GLC1A transcripts and thereby prevent translation of the GLC1A mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3' long terminal repeat of Rous sarcoma virus (Yamamoto et al., 1980, *Cell* 22:787–797), the herpes thyrnidine kinase promoter (Wagner et al., 1981, *Proc. Natl. Acad. Sci. U.S.A.* 78:1441–1445), the regulatory sequences of the metallothionein gene (Brinster et al, 1982, *Nature* 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave GLC1A mRNA transcripts can also be used to prevent translation of GLC1A mRNA and expression of myocilin. (See, e.g., PCT International Publication WO 90/11364, published Oct. 4, 1990; Sarver et al., 1990, *Science* 247:1222–1225). While ribozymes that cleave mRNA at site specific recognition sequences can be used to destroy GLC1A mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, *Nature*, 334:585–591. There are hundreds of potential hammerhead ribozyme cleavage sites within the nucleotide sequence of human GLC1A cDNA. Preferably the ribozyme is engineered so that the cleavage recognition site is located near the 5' end of the GLC1A mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, *Science*, 224:574–578; Zaug and Cech, 1986, *Science*, 231:470–475; Zaug, et al., 1986, Nature, 324:429–433; published International patent application No. WO 88/04300 by University Patents Inc.; Been and Cech, 1986, *Cell*, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in GLC1A.

As in the antisense approach, the ribozymes can be composed of modified oligonucleotides (e.g. for improved stability, targeting, etc.) and should be delivered to cells which express the GLC1A in vivo e.g., hypothalamus and/or the choroid plexus. A preferred method of delivery involves using a DNA construct "encoding" the ribozyme under the control of a strong constitutive pol III or pol II promoter, so that transfected cells will produce sufficient quantities of the ribozyme to destroy endogenous GLC1A messages and inhibit translation. Because ribozymes unlike antisense molecules, are catalytic, a lower intracellular concentration is required for efficiency.

Endogenous GLC1A gene expression can also be reduced by inactivating or "knocking out" the GLC1A gene or its promoter using targeted homologous recombination. (E.g., see Smithies et al., 1985, *Nature* 317:230–234; Thomas & Capecchi, 1987, *Cell* 51:503–512; Thompson et al., 1989 *Cell* 5:313–321; each of which is incorporated by reference herein in its entirety). For example, a mutant, non-functional GLC1A (or a completely unrelated DNA sequence) flanked by DNA homologous to the endogenous GLC1A gene (either the coding regions or regulatory regions of the GLC1A gene) can be used, with or without a selectable marker and/or a negative selectable marker, to transfect cells that express GLC1A in vivo. Insertion of the DNA construct, via targeted homologous recombination, results in inactivation of the GLC1A gene. Such approaches are particularly suited in the agricultural field where modifications to ES (embryonic stem) cells can be used to generate animal offspring with an inactive GLC1A (e.g., see Thomas &

Capecchi 1987 and Thompson 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous GLC1A gene expression can be reduced by targeting deoxyribonucleotide sequences complementary to the regulatory region of the GLC1A gene (i.e., the GLC1A promoter and/or enhancers) to form triple helical structures that prevent transcription of the GLC1A gene in target cells in the body. (See generally, Helene, C. 1991, *Anticancer Drug Des.*, 6(6):569–84; Helene, C., et al., 1992, Ann, N.Y. *Acad. Sci.*, 660:27–36; and Maher, L. J., 1992, *Bioassays* 14(12):807–15).

Likewise, the antisense constructs of the present invention, by antagonizing the normal biological activity of one of the myocilin proteins, can be used in the manipulation of tissue, e.g. tissue differentiation, both in vivo and for ex vivo tissue cultures.

Furthermore, the anti-sense techniques (e.g. mnicroinjection of antisense molecules, or transfection with plasmids whose transcripts are antisense with regard to a GLC1A mRNA or gene sequence) can be used to investigate role of myocilin in developmental events, as well as the normal cellular function of myocilin in adult tissue. Such techniques can be utilized in cell culture, but can also be used in the creation of transgenic animals, as detailed below.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding myocilin proteins.

Specific ribozyme cleavage sites within any potential RNA target are initially identified by scanning the molecule of interest for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features, such as secondary structure, that may render the oligonucleotide sequence unsuitable. The suitability of candidate sequences may also be evaluated by testing their accessibility to hybridization with complementary oligonucleotides, using ribonuclease protection assays.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

4.4. Polypeptides of the Present Invention

The present invention also makes available myocilin polypeptides, which are isolated from, or otherwise substantially free of other cellular proteins, especially other signal transduction factors and/or transcription factors which may normally be associated with the myocilin polypeptide. The term "substantially free of other cellular proteins" (also referred to herein as "contaminating proteins") or "substantially pure or purified preparations" are defined as encompassing preparations of myocilin polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified GLC1A preparations will lack any contaminating proteins from the same animal from which myocilin is normally produced, as can be accomplished by recombinant expression of, for example, a human myocilin protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated myocllin polypeptides can include all or a portion of an amino acid sequences corresponding to a myocilin polypeptide represented in SEQ ID Nos: 8 or 10. Isolated peptidyl portions of myocilin proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a myocilin polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") myocilin protein.

Another aspect of the present invention concerns recombinant forms of the myocilin proteins. Recombinant polypeptides preferred by the present invention, in addition to native myocilin proteins, are at least 91%, 92%, 93%, 94%, 95%, 96%, 97%, 98%, or 99% homologous with an amino acid sequence represented by SEQ ID Nos: 8 or 10. In a preferred embodiment, a myocilin protein of the present invention is a myocilin protein. In a particularly preferred embodiment, a myocilin protein comprises the coding sequence of one of SEQ ID No.: 1–7, or 9. In particularly preferred embodiments, a myocilin protein has a myocilin bioactivity.

The present invention further pertains to recombinant forms of one of the subject myocilin polypeptides which are encoded by genes derived from a mammalian organism, and which have amino acid sequences evolutionarily related to the myocilin proteins represented in SEQ ID Nos: 8 or 10. Such recombinant myocilin polypeptides preferably are capable of functioning in one of either role of an agonist or antagonist of at least one biological activity of a wild-type ("authentic") myocilin protein of the appended sequence listing. The term "evolutionarily related to", with respect to amino acid sequences of myocilin proteins, refers to both polypeptides having amino acid sequences which have arisen naturally, and also to mutational variants of myocilin polypeptides which are derived, for example, by combinatorial mutagenesis. Such evolutionarily derived myocilin polypeptides preferred by the present invention have a myocilin bioactivity and are at least 91%, 92%, 93%, 94%, 95%, 96%, 97%, 98% or 99% homologous with the amino acid sequence selected from the.group consisting of SEQ ID Nos: 8 or 10.

In general, polypeptides referred to herein as having an activity of a myocilin protein (e.g., are "bioactive") are defined as polypeptides which include an amino acid sequence corresponding (e.g., identical or homologous) to all or a portion of the amino acid sequences of a myocilin protein shown in SEQ ID Nos: 8 or 10 and which mimic or antagonize all or a portion of the biological/biochemical activities of a naturally occurring myocilin protein. According to the present invention, a polypeptide has biological activity if it is a specific agonist or antagonist of a naturally-occurring form of a myocilin protein.

The present invention further pertains to methods of producing the subject myocilin polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant myocilin polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant myocilin polypeptide is a fusion protein containing a domain which facilitates its purification, such as GST fusion protein or poly(His) fusion protein.

Moreover, it will be generally appreciated that, under certain circumstances, it may be advantageous to provide homologs of one of the subject myocilin polypeptides which function in a limited capacity as one of either a myocilin agonist (mimetic) or a myocilin antagonist, in order to promote or inhibit only a subset of the biological activities of the naturally-occurring form of the protein. Thus, specific biological effects can be elicited by treatment with a homolog of limited function, and with fewer side effects relative to treatment with agonists or antagonists which are directed to all of the biological activities of naturally occurring forms of myocilin proteins.

Homologs of each of the subject myocilin proteins can be generated by mutagenesis, such as by discrete point mutation(s), or by truncation. For instance, mutation can give rise to homologs which retain substantially the same, or merely a subset, of the biological activity of the myocilin polypeptide from which it was derived. Alternatively, antagonistic forms of the protein can be generated which are able to inhibit the function of the naturally occurring form of the protein, such as by competitively binding to a downstream or upstream member of the biochemical pathway, which includes the myocilin protein. In addition, agonistic forms of the protein may be generated which are constitutively active. Thus, the human myocilin protein and homologs thereof provided by the subject invention may be either positive or negative regulators of gene expression.

The recombinant myocilin polypeptides of the present invention also include homologs of the authentic myocilin proteins, such as versions of those protein which are resistant to proteolytic cleavage, as for example, due to mutations which alter ubiquitination or other enzymatic targeting associated with the protein.

Myocilin polypeptides may also be chemically modified to create derivatives by forming covalent or aggregate conjugates with other chemical moieties, such as glycosyl groups, lipids, phosphate, acetyl groups and the like. Covalent derivatives of myocilin proteins can be prepared by linking the chemical moieties to functional groups on amino acid sidechains of the protein or at the N-terminus or at the C-terminus of the polypeptide.

Modification of the structure of the subject myocilin polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the myocilin polypeptides described in more detail herein. Such modified peptides can be produced, for instance, by amino acid substitution, deletion, or addition.

For example, it is reasonable to expect that an isolated replacement of a leucine with an isoleucine or vaiine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, WH Freeman and Co.: 1981). Whether a change in the amino acid sequence of a peptide results in a functional myocilin homolog (e.g. functional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject myocilin proteins as well as truncation mutants, and is especially useful for identifying potential variant sequences (e.g. homologs) that are functional in modulating gene expression. The purpose of screening such combinatorial libraries is to generate, for example, novel myocilin homologs which can act as either agonists or antagonist, or alternatively, possess novel activities all together.

Likewise, myocilin homologs can be generated by the present combinatorial approach to selectively inhibit gene expression. For instance, mutagenesis can provide myocilin homologs which are able to bind other signal pathway proteins (or DNA) yet prevent propagation of the signal, e.g. the homologs can be dominant negative mutants. Moreover, manipulation of certain domains of myocilin by the present method can provide domains more suitable for use in fusion proteins.

In one embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential GLC1A sequences are expressible as individual polypeptides, or alternatively, as a set of larger fusion proteins (e.g. for phage display) containing the set of GLC1A sequences therein.

There are many ways by which such libraries of potential myocilin homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential myocilin sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier ppg. 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

Likewise, a library of coding sequence fragments can be provided for a GLC1A clone in order to generate a variegated population of myocilin fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a GLC1A coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of GLC1A homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate GLC1A sequences created by combinatorial mutagenesis techniques. Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the myocilin proteins to generate mimetics, e.g. peptide or non-peptide agents, which are able to disrupt binding of a mammalian myocilin polypeptide of the present invention with either upstream or downstream components. Thus, such mutagenic techniques as described above are also useful to map the determinants of the myocilin proteins which participate in protein-protein interactions involved in, for example, binding of the subject myocilin polypeptide to proteins which may function upstream (including both activators and repressors of its activity) or to proteins or nucleic acids which may function downstream of the myocilin polypeptide, whether they are positively or negatively regulated by it. To illustrate, the critical residues of a subject myocilin polypeptide which are involved in molecular recognition of a component upstream or downstream of myocilin can be determined and used to generate myocilin-derived peptidomimetics which competitively inhibit binding of the authentic myocilin protein with that moiety. By employing, for example, scanning mutagenesis to map the amino acid residues of each of the subject myoctlin proteins which are involved in binding other extracellular proteins, peptidomimetic compounds can be generated which mimic those residues of the myocilin protein which facilitate the interaction. Such mimetics may then be used to interfere with the normal function of a myocilin protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffinan et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and b-aminoalcohols (Gordon et al. (1985) *Biochem Biophys Res Commun* 126:419; and Dann et al. (1986) *Biochem Biophys Res Commun* 134:71).

4.4.1. Cells Expressing Recombinant Myocilin Polypeptides.

This invention also pertains to a host cell transfected to express a recombinant form of the subject myocilin polypeptides. The host cell may be any prokaryotic or eukaryotic cell. Thus, a nucleotide sequence derived from the cloning of myocilin proteins, encoding all or a selected portion of the full-length protein, can be used to produce a recombinant form of a myocilin polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial) cells, are standard procedures used in producing other well-known proteins, e.g. MAP kinase, pg. 53, WT1, PTP phosphotases, SRC, and the like. Similar procedures, or modifications thereof, can be employed to prepare recombinant myocilin polypeptides by microbial means or tissue-culture technology in accord with the subject invention.

The recombinant GLC1A genes can be produced by ligating nucleic acid encoding a myocilin protein, or a portion thereof, into a vector suitable for expression in either prokaryotic cells, eukaryotic cells, or both. Expression vectors for production of recombinant forms of the subject myocilin polypeptides include plasmids and other vectors. For instance, suitable vectors for the expression of a myocilin polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a myocilin polypeptide is produced recombinantly utilizing an expression vector generated by sub-cloning the coding sequence of one of the GLC1A genes represented in SEQ ID Nos: 1–7 or 9.

The preferred mammalian expression vectors contain both prokaryotic sequences, to facilitate the propagation of the vector in bacteria, and one or more eukaryotic transcription units that are expressed in eukaryotic cells. The pcDNA/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant myocilin polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a myocilin protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing myocilin-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

4.4.2 Fusion Proteins and Immunogens.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a myocilin protein. For example, the VP6 capsid protein of rotavirus can be used as an immunologic carrier protein for portions of the myocilin polypeptide, either in the monomeric form or in the form of a viral particle. The nucleic acid sequences corresponding to the portion of a subject myocilin protein to which antibodies are to be raised can be incorporated into a fusion gene construct which includes coding sequences for a late vaccinia virus structural protein to produce a set of recombinant viruses expressing fusion proteins comprising myocilin epitopes as part of the virion. It has been demonstrated with the use of immunogenic fusion proteins utilizing the Hepatitis B surface antigen fusion proteins that recombinant Hepatitis B virions can be utilized in this role as well. Similarly, chimeric constructs coding for fusion proteins containing a portion of a myocilin protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a myocilin polypeptide is obtained directly from organo-chemical synthesis of the peptide onto an oligomeric branching lysine core (see, for example, Posnett et al. (1988) *JBC* 263:1719 and Nardelli et al. (1992) *J. Immunol.* 148:914). Antigenic determinants of myocilin proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the myocilin polypeptides of the present invention. For example, myocilin polypeptides can be generated as glutathione-S-transferase (GST-fusion) proteins. Such GST-fusion proteins can enable easy purification of the myocilin polypeptide, as for example by the use of glutathione-derivatized matrices (see, for example, *Current Protocols in Molecular Biology*, eds. Ausubel et al. (N.Y.: John Wiley & Sons, 1991)).

In another embodiment, a fusion gene coding for a purification leader sequence, such as a poly-(His)/enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972). Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive.gene fragments which can subsequently be annealed to generate a chimeric gene sequence (see, for example, *Current Protocols in Molecular Biology*, eds. Ausubel et al. John Wiley & Sons: 1992).

4.4.3. Antibodies

Another aspect of the invention pertains to an antibody or binding fragment thereof, which is specifically reactive with a myocilin protein. For example, by using immunogens derived from a myocilin protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a myocilin polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a myocilin protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a myocilin protein of a mammal, e.g. antigenic determinants of a protein represented by SEQ ID No: 2 or closely related homologs (e.g. at least 92% homologous, and more preferably at least 94% homologous).

Following immunization of an animal with an antigenic preparation of a myocilin polypeptide, anti-myocilin antisera can be obtained and, if desired, polyclonal anti-myocilin antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, an include, for example, the hybridoma technique (originally developed by Kohler and Milstein, (1975) *Nature*, 256: 495–497), the human B cell hybridoma technique (Kozbar et al., (1983) *Immunology Today*, 4: 72), and the EBV-hybridoma technique to produce human monoclonal antibodies (Cole et al., (1985) *Monoclonal Antibodies and Cancer Therapy*, Alan R. Liss, Inc.

pp. 77–96). Hybridoma cells can be screened immunochemically for production of antibodies specifically reactive with a myocilin polypeptide of the present invention and monoclonal antibodies isolated from a culture comprising such hybridoma cells.

The term antibody as used herein is intended to include fragments thereof which are also specifically reactive with one of the subject mammalian myocilin polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific and chimeric molecules having affinity for a myocilin protein conferred by at least one CDR region of the antibody.

Antibodies which specifically bind myocilin epitopes can also be used in immunohistochemical staining of tissue samples in order to evaluate the abundance and pattern of expression of each of the subject myocilin polypeptides. Anti-myocilin antibodies can be used diagnostically in immuno-precipitation and immuno-blotting to detect and evaluate myocilin protein levels in tissue as part of a clinical testing procedure. For instance, such measurements can be useful in predictive valuations of the onset or progression of proliferative disorders. Likewise, the ability to monitor myocilin protein levels in an individual can allow determination of the efficacy of a given treatment regimen for an individual afflicted with such a disorder. The level of myocilin polypeptides may be measured from cells in bodily fluid, such as in samples of cerebral spinal fluid or amniotic fluid, or can be measured in tissue, such as produced by biopsy. Diagnostic assays using anti-myocilin antibodies can include, for example, immunoassays designed to aid in early diagnosis of a degenerative disorder, particularly ones which are manifest at birth. Diagnostic assays using anti-myocilin polypeptide antibodies can also include immunoassays designed to aid in early diagnosis and phenotyping neoplastic or hyperplastic disorders.

Another application of anti-myocilin antibodies of the present invention is in the immunological screening of cDNA libraries constructed in expression vectors such as gt11, gt18–23, ZAP, and ORF8. Messenger libraries of this type, having coding sequences inserted in the correct reading frame and orientation, can produce fusion proteins. For instance, gt11 will produce fusion proteins whose amino termini consist of β-galactosidase amino acid sequences and whose carboxy termini consist of a foreign polypeptide. Antigenic epitopes of a myocilin protein, e.g. other orthologs of a particular myocilin protein or other paralogs from the same species, can then be detected with antibodies, as, for example, reacting nitrocellulose filters lifted from infected plates with anti-myocilin antibodies. Positive phage detected by this assay can then be isolated from the infected plate. Thus, the presence of myocilin homologs can be detected and cloned from other animals, as can alternate isoforms (including splicing variants) from humans.

4.5 Transgenic Animals

The invention further provides for transgenic animals, which can be used for a variety of purposes, e.g., to identify myocilin therapeutics. Transgenic animals of the invention include non-human animals containing a heterologous GLC1A gene or fragment thereof under the control of a GLC1A promoter or under the control of a heterologous promoter. Accordingly, the transgenic animals of the invention can be animals expressing a transgene encoding a wild-type myocilin protein or fragment thereof or variants thereof, including mutants and polymorphic variants thereof Such animals can be used, e.g., to determine the effect of a difference in amino acid sequence of a myocilin protein from the sequence set forth in SEQ ID NOS. 8 or 10, such as a polymorphic difference. These animals can also be used to determine the effect of expression of a myocilin protein in a specific site or for identifying myocilin therapeutics or confirming their activity in vivo.

The transgenic animals can also be animals containing a transgene, such as reporter gene, under the control of a GLC1A promoter or fragment thereof These animals are useful, e.g., for identifying drugs that modulate production of myocilin, such as by modulating GLC1A gene expression. A GLC1A gene promoter can be isolated, e.g., by screening of a genomic library with a GLC1A cDNA fragment and characterized according to methods known in the art. In a preferred embodiment of the present invention, the transgenic animal containing said GLC1A reporter gene is used to screen a class of bioactive molecules known as steroid hormones for their ability to modulate GLC1A expression.

Yet other non-human animals within the scope of the invention include those in which the expression of the endogenous GLC1A gene has been mutated or "knocked out". A "knock out" animal is one canying a homozygous or heterozygous deletion of a particular gene or genes. These animals could be used to determine whether the absence of GLC1A will result in a specific phenotype, in particular whether these mice have or are likely to develop a specific disease, such as high susceptibility to heart disease or cancer. Furthermore these animals are useful in screens for drugs which alleviate or attenuate the disease condition resulting from the mutation of the GLC1A gene as outlined below. These animals are also useful for determining the effect of a specific amino acid difference, or allelic variation, in a GLC1A gene. That is, the GLC1A knock out animals can be crossed with transgenic animals expressing, e.g., a mutated form or allelic variant of GLC1A, thus resulting in an animal which expresses only the mutated protein and not the wild-type myocilin protein.

Methods for obtaining transgenic and knockout non-human animals are well known in the art. Knock out mice are generated by homologous integration of a "knock out" construct into a mouse embryonic stem cell chromosome which encodes the gene to be knocked out. In one embodiment, gene targeting, which is a method of using homologous recombination to modify an animal's genome, can be used to introduce changes into cultured embryonic stem cells. By targeting a GLC1A gene of interest in ES cells, these changes can be introduced into the germ lines of animals to generate chimeras. The gene targeting procedure is accomplished by introducing into tissue culture cells a DNA targeting construct that includes a segment homologous to a target GLC1A locus, and which also includes an intended sequence modification to the GLC1A genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a GLC1A gene function through the use of a targeting transgene construct designed to undergo homologous recombination with one or more GLC1A genomic sequences. The targeting construct can be arranged so that, upon recombination with an element of a GLC1A gene, a positive selection marker is inserted into (or replaces) coding sequences of the gene. The inserted sequence functionally disrupts the GLC1A gene, while also providing a positive selection trait. Exemplary GLC1A targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) *J. Embryol. Exp.* 87:27–45). Any line of ES cells can be used, however, the line chosen is typically selected for the ability of the cells to integrate into and become part of the germ line of a developing embryo so as to create germ line transmission of the knockout construct. Thus, any ES cel line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) *PNAS* 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C. [1987]); by Bradley et al. (1986) *Current Topics in Devel. Biol.* 20:357–371); and by Hogan et al. (Manipulating the Mouse Embryo: A Laboratory Manual, Cold Spring Harbor Laboratory Press, Cold Spring Harbor, N.Y. [1986]).

A knock out construct refers to a uniquely configured fragment of nucleic acid which is introduced into a stem cell line and allowed to recombine with the genome at the chromosomal locus of the gene of interest to be mutated. Thus a given knock out construct is specific for a given gene to be targeted for disruption. Nonetheless, many common elements exist among these constructs and these elements are well known in the art. A typical knock out construct contains nucleic acid fragments of not less than about 0.5 kb nor more than about 10.0 kb from both the 5' and the 3' ends of the genomic locus which encodes the gene to be mutated. These two fragments are separated by an intervening fragment of nucleic acid which encodes a positive selectable marker, such as the neomycin resistance gene (neo$^R$). The resulting nucleic acid fragment, consisting of a nucleic acid from the extreme 5' end of the genomic locus linked to a nucleic acid encoding a positive selectable marker which is in turn linked to a nucleic acid from the extreme 3' end of the genomic locus of interest, omits most of the coding sequence for GLC1A or other gene of interest to be knocked out. When the resulting construct recombines homologously with the chromosome at this locus, it results in the loss of the omitted coding sequence, otherwise known as the structural gene, from the genomic locus. A stem cell in which such a rare homologous recombination event has taken place can be selected for by virtue of the stable integration into the genome of the nucleic acid of the gene encoding the positive selectable marker and subsequent selection for cells expressing this marker gene in the presence of an appropriate drug (neomycin in this example). Variations on this basic technique also exist and are well known in the art. For example, a "knock-in" construct refers to the same basic arrangement of a nucleic acid encoding a 5' genomic locus fragment linked to nucleic acid encoding a positive selectable marker which in turn is linked to a nucleic acid encoding a 3' genomic locus fragment, but which differs in that none of the coding sequence is omitted and thus the 5' and the 3' genomic fragments used were initially contiguous before being disrupted by the introduction of the nucleic acid encoding the positive selectable marker gene. This "knock-in" type of construct is thus very useful for the construction of mutant transgenic animals when only a limited region of the genomic locus of the gene to be mutated, such as a single exon, is available for cloning and genetic manipulation. Alternatively, the "knock-in" construct can be used to specifically eliminate a single functional domain of the targeted gene, resulting in a transgenic animal which expresses a polypeptide of the targeted gene which is defective in one function, while retaining the function of other domains of the encoded polypeptide. This type of "knock-in" mutant frequently has the characteristic of a so-called "dominant negative" mutant because, especially in the case of proteins which homomultimerize, it can specifically block the action of (or "poison") the polypeptide product of the wild-type gene from which it was derived. In a variation of the knock-in technique, a marker gene is integrated at the genomic locus of interest such that expression of the marker gene comes under the control of the transcriptional regulatory elements of the targeted gene. A marker gene is one that encodes an enzyme whose activity can be detected (e.g., β-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

As mentioned above, the homologous recombination of the above described "knock out" and "knock in" constructs is very rare and frequently such a construct inserts nonhomologously into a random region of the genome where it has no effect on the gene which has been targeted for deletion, and where it can potentially recombine so as to disrupt another gene which was otherwise not intended to be altered. Such nonhomologous recombination events can be selected against by modifying the abovementioned knock out and knock in constructs so that they are flanked by negative selectable markers at either end (particularly through the use of two allelic variants of the thymidine kinase gene, the polypeptide product of which can be selected against in expressing cell lines in an appropriate tissue culture medium well known in the art—i.e. one containing a drug such as 5-bromodeoxyuridine). Thus a preferred embodiment of such a knock out or knock in construct of the invention consist of a nucleic acid encoding a negative selectable marker linked to a nucleic acid encoding a 5' end of a genomic locus linked to a nucleic acid of a positive selectable marker which in turn is linked to a nucleic acid encoding a 3' end of the same genomic locus which in turn is linked to a second nucleic acid encoding a negative selectable marker Nonhomologous recombination between the resulting knock out construct and the genome will usually result in the stable integration of one or both of these negative selectable marker genes and hence cells which have undergone nonhomologous recombination can be selected against by growth in the appropriate selective media (e.g. media containing a drug such as 5-bromodeoxyuridine for example). Simultaneous selection for the positive selectable marker and against the negative selectable marker will result in a vast enrichment for clones in which the knock out construct has recombined homologously at the locus of the gene intended to be mutated. The presence of the predicted chromosomal alteration at the targeted gene locus in the resulting knock out stem cell line can be confirmed by means of Southern blot analytical techniques which are well known to those familiar in the art. Alternatively, PCR can be used.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. For example, if the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knock out construct as explained above. Where more than one construct is to be introduced into the ES cell, each knockout construct can be introduced simultaneously or one at a time.

After suitable ES cells containing the knockout construct in the proper location have been identified by the selection techniques outlined above, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the knockout construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the GLC1A gene knocked out in various tissues of the offspring by probing the Western blot with an antibody against the particular myocilin protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a GLC1A-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

A GLC1A transgene can encode the wild-type form of the protein, or can encode homologs thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a myocilin protein can be essential for many forms of lineage analysis and can additionally provide a means to assess the effects of, for example, lack of GLC1A expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques, which allow for the expression of transgenes can be regulated via site-specific genetic manipulation in vivo, are known to those skilled in the art. For instance, genetic systems are available which allow for the regulated expression of a recombinase that catalyzes the genetic recombination of a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject myocilin proteins. For example, excision of a target sequence which interferes with the expression of a recombinant GLC1A gene, such as one which encodes an antagonistic homolog or an antisense transcript, can be designed to activate expression of that gene. This interference with expression of the protein can result from a variety of mechanisms, such as spatial separation of the GLC1A gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *PNAS* 89:6232–6236; Orban et al. (1992) *PNAS* 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant myocilin protein can be regulated via control of recombinase expression.

Use of the cre/loxP recombinase system to regulate expression of a recombinant myocilin protein requires the construction of a transgenic animal containing transgenes encoding both the Cre recombinase and the subject protein. Animals containing both the Cre recombinase and a recombinant GLC1A gene can be provided through the construction of "double" transgenic animals. A convenient method for providing such animals is to mate two transgenic animals each containing a transgene, e.g., a GLC1A gene and recombinase gene.

Similar conditional transgenes can be provided using prokaryotic promoter sequences which require prokaryotic proteins to be simultaneous expressed in order to facilitate expression of the GLC1A transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a GLC1A transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Ml.). Preferred strains are those with H-$2^b$, H-$2^d$ or H-2q haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred.

It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a myocilin protein (either agonistic or antagonistic), and antisense transcript, or a myocilin mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona peilucida (*Manipukrtng the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) *PNAS* 82:6148–6152). Transfection is easily and efficiently obtained by culturing the blastomeres on a monolayer of virus-producing cells (Van der Putten, supra; Stewart et al. (1987) *EMBO J*. 6:383–388). Alternatively, infection can be performed at a later stage. Virus or virus-producing cells can be injected into the blastocoele (Jahner et al. (1982) *Nature* 298:623– 628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) *PNAS* 83: 9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.6. Drug Screening Assays for GLC1A Therapeutics

Based on the discovery of the GLC1A gene and specific mutations in the gene that correlate with the existence of glaucoma, one of skill in the art is able to use any of a variety of standard assays to screen for drugs, which will interfere with or otherwise prevent the development of glaucoma. By addressing the molecular basis of glaucoma, these agents are expected to be superior to existing therapies.

For example, identification of the precise phenotype associated with these mutations can be used to identify functionally important regions of the protein. These specific mutations can then be used in other experiments which will include overexpression in cell lines and the creation of transgenic animals. Ideally, one could identify mutations which reproducibly cause glaucoma at very different times in the person's life and then be able to show that these mutations had similar differences of effect in a cellular expression system or a transgenic animal.

In addition, proteins that interact with the GLC1A gene product and genes encoding the proteins can now be identified, since proteins that interact with GLC1A gene product will be important targets for involvement in the pathogenesis of various types of glaucoma.

Further, studies will be undertaken to discover whether mutations known to cause glaucoma in human beings alter protein trafficking in tissue culture as well as animal models, since one mechanism through which mutations in the GLC1A gene could cause disease would be to alter the expression of other important gene products. This can occur by affecting overall protein trafficking within the cell caused for example by increased removal of mutant proteins at the level of the endoplasmic reticulum.

Further understanding of the pathogenesis of glaucoma is useful for identifying new classes of drugs which can be useful in the treatment of glaucoma. For example, the GLC1A gene has been found to be induced by exposure of cells to steroids. Therefore, drugs which are capable of blocking this steroid effect should prove useful for preventing or delaying the development of glaucoma.

As further described below, in vitro assays which are suitable for very high throughput screening of compounds can be performed. As the simplest example of this approach, one could use antibodies to the GLC1A gene product to develop a simple ELISA assay for the induction of the GLC1A gene product and then perform this assay in a 96 well microtiter plate format to screen a large number of drugs for the efficacy in blocking the steroid induction of the gene product. In this way, automated methods could be used to screen several thousand potentially therapeutic compounds for efficacy.

Also, knowledge of the structure/function of the GLC1A gene immediately suggests other genes which might be involved in glaucoma. Such clues will come from studies of homology, evolution, evaluation of structural motifs within the gene, and genetic studies using analyses designed to identify genes causing polygenic disease.

In the original linkage study described herein, it was recognized that 3 of obligate carriers of the glaucoma gene failed to manifest a severe glaucoma phenotype. This information suggests that other genes are capable of mitigating the effect of the GLC1A mutation. One powerful way to search for such mitigator genes is to express a glaucoma-causing gene in different backgrounds. This can be done by creating transgenic animals and then breeding the glaucoma-causing gene on different genetic mouse strains. If the phenotype is altered in different strains these animals can be back crossed in such a way that the mitigating gene can be identified.

Some of the assays mentioned above, will now be described in further detail below.

4.6.1 Cell-free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the myocilin polypeptide, whether they are positively or negatively regulated by it. To the mixture of the compound and the upstream or downstream element is then added a composition containing a myocilin polypeptide. Detection and quantification of complexes of myocilin with it's upstream or downstream elements provide a means for determining a compound's efficacy at inhibiting (or potentiating) complex formation between myocilin and a myocilin-binding element. The efficacy of the compound can be assessed by generating dose response curves from data obtained using various concentrations of the test compound. Moreover, a control assay can also be performed to provide a baseline for comparison. In the control assay, isolated and purified myocilin polypeptide is added to a composition containing the myocilin-binding element, and the formation of a complex is quantitated in the absence of the test compound.

Complex formation between the myocilin polypeptide and a myocilin binding element may be detected by a variety of techniques. Modulation of the formation of complexes can be quantitated using, for example, detectably labeled proteins such as radiolabeled, fluorescently labeled, or enzymatically labeled myocilin polypeptides, by immunoassay, or by chromatographic detection.

Typically, it will be desirable to immobilize either myocilin or its binding protein to facilitate separation of complexes from uncomplexed forms of one or both of the proteins, as well as to accommodate automation of the assay. Binding of myocilin to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/myocilin (GST/myocilin) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintilant), or in the supernatant after the complexes are subsequently dissociated. Alternatively, the complexes can be dissociated from the matrix, separated by SDS-PAGE, and the level of myocilin-binding protein found in the bead fraction quantitated from the gel using standard electrophoretic techniques such as described in the appended examples.

Other techniques for immobilizing proteins on matrices are also available for use in the subject assay. For instance, either myocilin or its cognate binding protein can be immobilized utilizing conjugation of biotin and streptavidin. For instance, biotinylated myocilin molecules can be prepared from biotin-NHS (N-hydroxy-succinimide) using techniques well known in the art (e.g., biotinylation kdt, Pierce Chemicals, Rockford, Ill.), and immobilized in the wells of streptavidin-coated 96 well plates (Pierce Chemical). Alternatively, antibodies reactive with myocilin but which do not interfere with binding of upstream or downstream elements can be derivatized to the wells of the plate, and myocilin trapped in the wells by antibody conjugation. As above, preparations of a myocilin-binding protein and a test compound are incubated in the myocilin-presenting wells of the plate, and the amount of complex trapped in the well can be quantitated. Exemplary methods for detecting such complexes, in addition to those described above for the GST-immobilized complexes, include immunodetection of complexes using antibodies reactive with the myocilin binding element, or which are reactive with myocilin protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the myocllin-BP. To illustrate, the myocilin-BP can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) J Biol Chem 249:7130).

For processes which rely on immunodetection for quantitating one of the proteins trapped in the complex, antibodies against the protein, such as anti-myocilin antibodies, can be used. Alternatively, the protein to be detected in the complex can be "epitope tagged" in the form of a fusion protein which includes, in addition to the myocilin sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) J Biol Chem 266:21150–21157) which includes a 10-residue sequence from c-myc, as well as the pFLAG system (International Biotechnologies, Inc.) or the pEZZ-protein A system (Pharamacia, NJ).

4.6.2. Cell Based Assays

In addition to cell-free assays, such as described above, the readily available source of mutant and functional GLC1A nucleic acids and proteins provided by the present invention also facilitates the generation of cell-based assays for identifying small molecule agonists/antagonists and the like. For example, cells can be caused to overexpress a recombinant myocilin protein in the presence and absence of a test agent of interest, with the assay scoring for modulation in myocilin responses by the target cell mediated by the test agent. As with the cell-free assays, agents which produce a statistically significant change in myocilin-dependent responses (either inhibition or potentiation) can be identified. In an illustrative embodiment, the expression or activity of a myocilin is modulated in cells and the effects of compounds of interest on the readout of interest (such as tissue differentiation, proliferation, tumorigenesis) are measured. For example, the expression of genes which are up- or down-regulated in response to a myocilin-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Exemplary cells or cell lines may be derived from ocular tissue (e.g. trabecular meshwork or ciliary body epithelia); as well as generic mammalian cell lines such as HeLa cells and COS cells, e.g., COS-7 (ATCC# CRL-1651). Further, the transgenic animals discussed herein may be used to generate cell lines containing one or more cell types involved in glaucoma, that can be used as cell culture models for this disorder. While primary cultures derived from the glaucomatous transgenic animals of the invention may be utilized, the generation of continuous cell lines is preferred. For examples of techniques which may be used to derive a continuous cell line from the transgenic animals, see Small et al., 1985, Mol. Cell Biol. 5:642–648.

Using these cells, the effect of a test compound on a variety of end points can be tested including cell proliferation, migration, phagocytosis, adherence and/or biosynthesis (e.g. of extracellular matrix components). The cells can then be examined for phenotypes associated with glaucoma, including, but not limited to changes in cellular morphology, cell proliferation, cell migration, and cell adhesion.

In the event that the myocilin proteins themselves, or in complexes with other proteins, are capable of binding DNA and modifying transcription of a gene, a transcriptional based assay could be used, for example, in which a myocilin responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject myocilin polypeptides can be used to generate a "two hybrid" assay (see, for example, U.S. Pat. No. 5,283,317; Zervos et al. (1993) Cell 72:223–232; Madura et al. (1993) *J Biol Chem* 268:12046–12054; Bartel et al. (1993) Biotechniques 14:920–924; Iwabuchi et al. (1993) Oncogene 8:1693–1696; and Brent WO 94/10300), for isolating coding sequences for other cellular proteins which bind to or interact with myocilin ("myocilin-binding proteins" or "myocilin-bp).

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a myocilin polypeptide. The second hybrid protein encodes a transcriptional activation domain fused in frame to a sample gene from a cDNA library. If the bait and sample hybrid proteins are able to interact, e.g., form a myocilin-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the myocilin and sample proteins.

This invention further pertains to novel agents identified by the above-described screening assays and uses thereof for treatments as described herein.

4.7 Methods of Treating Disease

In addition to glaucoma, there may be a variety of pathological conditions for which myocilin therapeutics of the present invention can be used in treatment.

A "myocilin therapeutic," whether an antagonist or agonist of wild type myocilin, can be, as appropriate, any of the preparations described above, including isolated polypeptides, gene therapy constructs, antisense molecules, peptidomimetics, non-nucleic acid, non-peptidic small molecules, or agents identified in the drug assays provided herein.

As described herein, subjects having certain mutant GLC1A genes tend to develop glaucoma. Down-regulation of mutant GLC1A gene expression and/or a resultant decrease in the activity of a mutant myocilin protein (e.g. using antisense, ribozyme, triple helix or antibody molecules) and/or up-regulation of a wildtype GLC1A gene expression and/or a resultant increase in the activity of a wildtype myocilin protein (e.g. using gene therapy or protein replacement therapies) should therefore prove useful in ameliorating disease symptoms. Compounds identified as increasing or decreasing GLC1A gene expression or myocilin protein activity can be administered to a subject at therapeutically effective dose to treat or ameliorate symptoms associated with glaucoma.

4.7.1. Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.7.2. Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic GLC1A gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *PNAS* 91: 3054–3057). A GLC1A gene, such as any one of the sequences represented in the group consisting of SEQ ID NO: 1 or 2, or a sequence homologous thereto can be delivered in a gene therapy construct by electroporation using techniques described, for example, by Dev et al. ((1994) *Cancer Treat Rev* 20:105–115). Gene therapy vectors comprised of viruses that provide specific effective and highly localized treatment of eye diseases are described in Published International Patent Application No. WO 95/34580 to U. Eriksson et al.

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil such as a blister pack. The pack or dispenser device may be accompanied by instructions for administration.

4.8 Predictive Medicine

The invention further features predictive medicines, which are based, at least in part, on the identity of the novel GLC1A genes and alterations in the genes and related pathway genes, which affect the expression level and/or function of the encoded myocilin protein in a subject.

For example, information obtained using the diagnostic assays described herein (alone or in conjunction with information on another genetic defect, which contributes to the same disease) is useful for diagnosing or confirming that a symptomatic subject (e.g. a subject symptomatic for glaucoma), has a genetic defect (e.g. in a GLC1A gene or in a gene that regulates the expression of an GLC1A gene), which causes or contributes to glaucoma. Alternatively, the information (alone or in conjunction with information on another genetic defect, which contributes to the same disease) can be used prognostically for predicting whether a non-symptomatic subject is likely to develop glaucoma. Based on the prognostic information, a doctor can recommend a regimen or therapeutic protocol, useful for preventing or prolonging onset of glaucoma in the individual.

In addition, knowledge of the particular alteration or alterations resulting in defective or deficient GLC1A genes or proteins in an individual (the GLC1A genetic profile), alone or in conjunction with information on other genetic defects contributing to glaucoma (the genetic profile of glaucoma) allows customization of therapy to the individual's genetic profile, the goal of "pharmacogenomics". For example, an individual's GLC1A genetic profile or the genetic profile of glaucoma, can enable a doctor to: 1) more effectively prescribe a drug that will address the molecular basis of glaucoma; and 2) better determine the appropriate dosage of a particular drug. For example, the expression level of myocilin proteins, alone or in conjunction with the expression level of other genes, known to contribute to glaucoma, can be measured in many patients at various stages of the disease to generate a transcriptional or expression profile of glaucoma. Expression patterns of individual patients can then be compared to the expression profile of glaucoma to determine the appropriate drug and dose to administer to the patient.

The ability to target populations expected to show the highest clinical benefit, based on the GLC1A or glaucoma genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of GLC1A as a marker is useful for optimizing effective dose).

These and other methods are described in further detail in the following sections.

4.8.1. Prognostic and Diagnostic Assays

The present methods provide means for determining if a subject has (diagnostic) or is at risk of developing (prognostic) glaucoma.

In one embodiment, the method comprises determining whether a subject has an abnormal GLC1A mRNA and/or myocilin protein level, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the level of GLC1A mRNA or myocilin level is determined and compared to the mRNA or protein level in a healthy subject. An abnormal level of GLC1A mRNA or myocilin therefor being indicative of an aberrant myocilin bioactivity. In another embodiment, the method comprises measuring at least one activity of myocilin. Similarly, the constant of affinity of a myocilin protein of a subject with a binding partner can be determined. Comparison of the results obtained with results from similar analysis performed on myocilin proteins from healthy subjects is indicative of whether a subject has an abnormal myocilin activity.

In preferred embodiments, the methods for determining whether a subject has or is at risk for developing glaucoma is characterized as comprising detecting, in a sample of cells from the subject, the presence or absence of a genetic alteration characterized by at least one of (i) an alteration affecting the integrity of a gene encoding a myocilin polypeptide, or (ii) the mis-expression of the GLC1A gene. For example, such genetic alterations can be detected by ascertaining the existence of at least one of (i) a deletion of one or more nucleotides from a GLC1A gene, (ii) an addition of one or more nucleotides to a GLC1A gene, (iii) a substitution of one or more nucleotides of a GLC1A gene, (iv) a gross chromosomal rearrangement of a GLC1A gene, (v) a gross alteration in the level of a messenger RNA transcript of a GLC1A gene, (vi) aberrant modification of a GLC1A gene, such as of the methylation pattern of the genomic DNA, (vii) the presence of a non-wild type splicing pattern of a messenger RNA transcript of a GLC1A gene, (viii) a non-wild type level of a myocilin polypeptide, (ix) allelic loss of a GLC1A gene, and/or (x) inappropriate post-translational modification of a myocilin polypeptide. As set out below, the present invention provides a variety of assay techniques for detecting alterations in a GLC1A gene. These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in GLC1A genes, can be identified by determining the nucleotide sequence of genes in populations of individuals. If a polymorphic region, e.g., SNP is identified, then the link with a specific disease can be determined by studying specific populations of individuals, e.g, individuals which developed glaucoma. A polymorphic region can be located in any region of a gene, e.g., exons, in coding or non-coding regions of exons, introns, and promoter region.

It is likely that GLC1A genes comprise polymorphic regions, specific alleles of which may be associated with specific diseases or conditions or with an increased likelihood of developing such diseases or conditions. Thus, the invention provides methods for determining the identity of the allele or allelic variant of a polymorphic region of a GLC1A gene in a subject, to thereby determine whether the subject has or is at risk of developing a disease or disorder associated with a specific allelic variant of a polymorphic region.

In an exemplary embodiment, there is provided a nucleic acid composition comprising a nucleic acid probe including a region of nucleotide sequence which is capable of hybridizing to a sense or antisense sequence of a GLC1A gene or naturally occurring mutants thereof, or 5' or 3' flanking sequences or intronic sequences naturally associated with the subject GLC1A genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect alterations or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants, such as single nucleotide polymorphisms, are attached to a solid phase support, e.g., a "chip". Oligonucleotides can be bound to a solid support by a variety of processes, including lithography. For example a chip can hold up to 250,000 oligonucleotides. Mutation detection analysis using these chips comprising oligonucleotides, also termed "DNA probe arrays" is described e.g., in Cronin et al. (1996) Human Mutation 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the alteration comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the GLC1A gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a GLC1A gene under conditions such that hybridization and amplification of the GLC1A gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, Proc. Natl. Acad. Sci. USA 87:1874–1878), transcriptional amplification system (Kwoh, D. Y. et al., 1989, Proc. Natl. Acad. Sci. USA 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In a preferred embodiment of the subject assay, mutations in, or allelic variants, of a GLC1A gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the GLC1A gene and detect mutations by comparing the sequence of the sample GLC1A with the corresponding wild-type (control) sequence. Exemplary sequencing reactions include those based on techniques developed by Maxim and Gilbert (*Proc. Natl Acad Sci USA* (1977) 74:560) or Sanger (Sanger et al (1977) *Proc. Nat. Acad. Sci* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127–162; and Griffin et al. (1993) *Appl Biochem Biotechnol* 38:147–159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type GLC1A sequence with potentially mutant RNA or DNA obtained from a tissue sample. The double-stranded duplexes are treated with an agent which cleaves single-stranded regions of the duplex as will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl Acad Sci USA* 85:4397; Saleeba et al (1992) Methods Enzymol. 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in GLC1A cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a GLC1A sequence, e.g., a wild-type GLC1A sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in GLC1A genes. For example, single strand conformation polymorphism (SSCP) may be used to detect differences in electrophoretic mobility between mutant and wild type nucleic acids (Orita et al. (1989) *Proc Natl. Acad Sci USA* 86:2766, see also Cotton (1993) *Mutat Res* 285:125–144; and Hayashi (1992) *Genet Anal Tech Appl* 9:73–79). Single-stranded DNA fragments of sample and control GLC1A nucleic acids are denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet 7:5).

In yet another embodiment, the movement of mutant or wild-type fragments in polyacrylamide gels containing a gradient of denaturant is assayed using denaturing gradient gel electrophoresis (DGGE) (Myers et al (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys Chem 265:12753).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al (1989) *Nucleic Acids Res*. 17:2437–2448) or at the extreme 3' end of one primer where, under appropriate conditions, mismatch can prevent, or reduce polymerase extension (Prossner (1993) *Tibtech* 11:238. In addition it may be desirable to introduce a novel restriction site in the region of the mutation to create cleavage-based detection (Gasparini et al (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren, U. et al., Science 241:1077–1080 (1988). The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson, D. A. et al., Proc. Natl. Acad. Sci. (U.S.A.) 87:8923–8927 (1990). In this method, PCR is used to achieve the exponential amplification of target DNA, which is then detected using OLA.

Several techniques based on this OLA method have been developed and can be used to detect specific allelic variants of a polymorphic region of a GLCI1A gene. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996) Nucleic Acids Res 24: 3728), OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

The invention further provides methods for detecting single nucleotide polymorphisms in a GLC1A gene. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy, C. R. (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method is advantageous, since it does not require the determination of large amounts of extraneous sequence data.

In another embodiment of the invention, a solution-based method is used for determining the identity of the nucleotide of a polymorphic site. Cohen, D. et al. (French Patent 2,650,840; PCT Appln. No. WO 91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet, P. et al. (PCT Appln. No. 92/15712). The method of Goelet, P. et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Appln. No. WO 091/02087) the method of Goelet, P. et al. is preferably a heterogeneous phase assay, in which the primer or the target molecule is immobilized to a solid phase.

Recently, several primer-guided nucleotide incorporation procedures for assaying polymorphic sites in DNA have been described (Komher, J. S. et al., Nucl. Acids. Res. 17:7779–7784 (1989); Sokolov, B. P., Nucl. Acids Res. 18:3671 (1990); Syvanen, A. -C., et al., Genomics 8:684–692 (1990); Kuppuswamy, M. N. et al., Proc. Natl. Acad. Sci. (U.S.A.) 88:1143–1147 (1991); Prezant, T. R. et al., Hum. Mutat. 1:159–164 (1992); Ugozzoli, L. et al., GATA 9:107–112 (1992); Nyren, P. et al., Anal. Biochem. 208:171–175 (1993)). These methods differ from GBA TM in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. -C., et al., Amer. J. Hum. Genet. 52:46–59 (1993)).

For mutations that produce premature termination of protein translation, the protein truncation test (PTT) offers an efficient diagnostic approach (Roest, et. al., (1993) *Hum. Mol. Genet.* 2:1719–21; van der Luijt, et. al., (1994) *Genomics* 20:1–4). For PTT, RNA is initially isolated from available tissue and reverse-transcribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of glaucoma.

Any cell type or tissue may be utilized in the diagnostics described below. In a preferred embodiment a bodily fluid, e.g., blood, is obtained from the subject to determine the presence of a mutation or the identity of the allelic variant of a polymorphic region of a GLC1A gene. A bodily fluid, e.g., blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

When using RNA or protein to determine the presence of a mutation or of a specific allelic variant of a polymorphic region of a GLC1A gene, the cells or tissues that may be utilized must express the GLC1A gene. Preferred cells for use in these methods include photoreceptors cells of retina. Alternative cells or tissues that can be used, can be identified by determining the expression pattern of the specific GLC1A gene in a subject, such as by Northern blot analysis.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ hybridization: protocols and applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant myocilin polypeptides or allelic variants thereof, which are discussed above, may also be used in disease diagnostics and prognostics. Such diagnostic methods, may be used to detect abnormalities in the level of myocilin polypeptide expression, or abnormalities in the structure and/or tissue, cellular, or subcellular location of a myocilin polypeptide. Structural differences may include, for example, differences in the size, electronegativity, or antigenicity of the mutant myocilin polypeptide relative to the normal myocilin polypeptide. Protein from the tissue or cell type to be analyzed may easily be detected or isolated using techniques which are well known to one of skill in the art, including but not limited to western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of myocilin polypeptides. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the myocilin polypeptide, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-myocilin polypeptide specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamnine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

4.8.2. Pharmacogenomics

Knowledge of the particular alteration or alterations, resulting in defective or deficient GLC1A genes or proteins in an individual (the GLC1A genetic profile), alone or in conjunction with information on other genetic defects contributing to glaucoma (the genetic profile of glaucoma) allows a customization of the therapy for glaucoma to the individual's genetic profile, the.goal of "pharmacogenomics". For example, subjects having a specific allele of a GLC1A gene may or may not exhibit symptoms of glaucoma or be predisposed to developing symptoms glaucoma. Further, if those subjects are symptomatic, they may or may not respond to a certain drug, e.g., a specific GLC1A therapeutic, but may respond to another. Thus, generation of a GLC1A genetic profile, (e.g., categorization of alterations in GLC1A genes which are associated with the development of glaucoma), from a population of subjects, who are symptomatic for glaucoma (a glaucoma genetic population profile) and comparison of an individual's GLC1A profile to the population profile, permits the selection or design of drugs that should be safer and more effective for a particular patient or patient population (i.e., a group of patients having the same genetic alteration).

For example, a GLC1A population profile can be performed, by determining the GLC1A profile, e.g., the identity of GLC1A genes, in a patient population having glaucoma. Optionally, the GLC1A population profile can further include information relating to the response of the population to a GLC1A therapeutic, using any of a variety of methods, including, monitoring: 1) the severity of symptoms associated with the GLC1A related disease, 2) GLC1A gene expression level, 3) GLC1A mRNA level and/or 4) GLC1A protein level. and (iii) dividing or categorizing the population based on the particular genetic alteration or alterations present in its GLC1A gene or a GLC1A pathway gene. The GLC1A genetic population profile can also, optionally, indicate those particular alterations in which the patient was either responsive or non-responsive to a particular therapeutic. This information or population profile, is then useful for predicting which individuals should respond to particular drugs, based on their individual GLC1A profile.

In a preferred embodiment, the GLC1A profile is a transcriptional or expression level profile and step (i) is comprised of determining the expression level of GLC1A proteins, alone or in conjunction with the expression level of other genes, known to contribute to the same disease. The GLC1A profile can be measured in many patients at various stages of the disease.

Pharmacogenomic studies can also be performed using transgenic animals. For example, one can produce transgenic mice, e.g., as described herein, which contain a specific allelic variant of a GLC1A gene. These mice can be created, e.g, by replacing their wild-type GLC1A gene with an allele of the human GLC1A gene. The response of these mice to specific GLC1A therapeutics can then be determined.

4.8.3. Monitoring of Effects of GLC1A Therapeutics During Clinical Trials

The ability to target populations expected to show the highest clinical benefit, based on the GLC1A or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since the use of GLC1A as a marker is useful for optimizing effective dose).

The treatment of an individual with a GLC1A therapeutic can be monitored by determining GLC1A characteristics, such as myocilin protein level or activity, GLC1A mRNA level, and/or transcriptional level. This measurements will indicate whether the treatment is effective or whether it should be adjusted or optimized. Thus, GLC1A can be used as a marker for the efficacy of a drug during clinical trials.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate, for example a drug candidate identified by the screening assays described herein) comprising the steps of (i) obtaining a preadministration sample from a subject prior to administration of the agent; (ii) detecting the level of expression of a myocilin protein, mRNA, or genomic DNA in the preadministration sample; (iii) obtaining one or more post-administration samples from the subject; (iv) detecting the level of expression or activity of the myocilin protein, mRNA, or genomic DNA in the post-administration samples; (v) comparing the level of expression or activity of the myocilin protein, mRNA, or genomic DNA in the preadministration sample with the myocilin protein, mRNA, or genomic DNA in the post administration sample or samples; and (vi) altering the administration of the agent to the subject accordingly. For example, increased administration of the agent may be desirable to increase the expression of a wildtype GLC1A gene or activity of a wildtype myocilin protein to higher levels than detected. Alternatively, decreased administration of the agent may be desirable to decrease expression of a mutant GLC1A gene or activity of a mutant myocilin protein to lower levels than detected.

Cells of a subject may also be obtained before and after administration of a GLC1A therapeutic to detect the level of expression of genes other than GLC1A, to verify that the GLC1A therapeutic does not increase or decrease the expression of genes which could be deleterious. This can be done, e.g., by using the method of transcriptional profiling. Thus, mRNA from cells exposed in vivo to a GLC1A therapeutic and mRNA from the same type of cells that were not exposed to the GLC1A therapeutic could be reverse transcribed and hybridized to a chip containing DNA from numerous genes, to thereby compare the expression of genes in cells treated and not treated with a GLC1A therapeutic. If, for example a GLC1A therapeutic turns on the expression of a proto-oncogene in an individual, use of this particular GLC1A therapeutic may be undesirable.

The present invention is fuirther illustrated by the following examples which should not be construed as limiting in any way. The contents of all cited references (including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo*, (Cold Spring Harbor Laboratory Press, Cold Spring Harbor, N.Y., 1986).

The present invention is further illustrated by the following examples which should not be construed as limiting in any way. The contents of all cited references (including literature references, issued patents, published patent applications, and co-pending patent applications) cited throughout this application are hereby expressly incorporated by reference.

5.1 Genetic Linkage of Familial Open Angle Glaucoma to Chromosome 1q21-q31

Materials and Methods

Pedigree

A family in which five consecutive.generations have been affected with juvenile-onset, open-angle glacoma without iridocorneal angle abnormalities was identified. The family comprised descendants of a woman who emigrated from Germany to the midwestern United States in the late 1800s. The disease state in affected family members included onset during the first 3 decades of life, normal anterior chamber angles, high intraocular pressures, lack of systemic or other ocular abnormalities, and need for surgery to control the glaucoma in affected individuals. A total of 35 family members at 50% risk for glaucoma had complete eye examinations including visual acuity with refraction, slit-lamp biomicroscopy, applanation tomometry, gonioscopy, stereo disc photography and Humphrey, Goldmann or Octopus perimetry. Two other affected patients were ascertained by reviewing records of other ophthalmologists. Patients were considered to be affected for linkage if they had documented pressures greater than 30 mm Hg and evidence of optic nerve or visual field damage; or, if they had intraocular pressures greater than 22 mm Hg and an obviously affected child. Affected family members are characterized by an early age of diagnosis, a normal appearing trabecular meshwork, very high intraocular pressures (often above 50 mm Hg), and relatively pressure-resistant optic nerves. FIG. 1 is a pictorial representation of the pedigree.

DNA typing

Blood samples were obtained from all living affected family members as well as six spouses of affected patients with children. 10 ml blood were obtained from each patient in EDTA-containing glass tubes. DNA was prepared from the blood using a non-organic extraction procedure (Grimberg, J. et al. Nucl. Acids Res 17, 8390 (1989)). Short tandem repeat polymorphisms (STRPs) distributed across the entire autosomal genome were selected from the literature or from those kindly provided by J. L. Weber. The majority were [dC-dA]-[dG-dT] dinucleotide repeats. Oligonucleotide primers flanking each STRP were synthesized using standard phosphoramidite chemistry (Applied Biosystems model 391 DNA synthesizer). Amplification of each STRP was performed with 50 ng of each patient's DNA in a 8.35 1 PCR containing each of the following: 1.25 1 10×buffer (100 mM Tris-HCl pH 8.8, 500 mM KCl, 15 mM MgCl$_2$, 0.01% w/v gelatin), 300 M each of dCTP, dGTP and dTTP, 37M dATP, 50 pmoles each primer, 0.25 1-$^{35}$S-dATP (Amersham,>1000 Ci mmol$^{-1}$), and 0.25 U Taq polymerase (Perkin-Elmer/Cetus). Samples were incubated in a DNA thermocycler Perkin-Elmer/Cetus) for 35 cycles under the following conditions: 94C for 30 s, 55C for 30 s, and 72C for 30 s. Following amplification, 51 of stop solution (95% formamide, 10 mM NaOH, 0.05% Bromophenol Blue, 0.05% Xylene Cyanol) was added to each sample. Following denaturation for 3 min at 95C, 5 1 of each sample was immediately loaded onto prewarmed polyacrylamide gels (6% polyacrylamide, 7 M urea) and electrophoresed for 3–4 h. Gels were then placed on Whatman, 3 mm paper and dried in a slab gel dryer. Autoradiographs were created by exposing Kodak Xomat AR film to the dried gels for 24–36 h.

Linkage Analysis

Genotypic data from the autoradiographs were entered into a Macintosh computer. A Hypercard-based program (Nichols, B E et al., Am J Hum Genet 51 A369 (1992)) was used to store and retrieve marker data as well as to export it to a DOS-compatible machine for analysis with the computer program LINKAGE (version 5.1) (Lathrop, G M and LaLouel, J M 359, 794–801 (1992)). Allele frequencies were assumed to be equal for each marker. The MLINK routine was used for pairwise analysis. The relative odds of all possible orders of the disease and two markers (D1S191 and D1S194) was performed under the ILINK program. Significance of linkage was evaluated using the standard criterion ($Z_{max}$>3.0).

Results

Clinical Findings

All of the 37 family members studied were at 50% risk of having the disease because of a known affected parent or sibling. Nineteen of these patients had elevated intraocular pressures and visual field defects consistent with the diagnosis of primary open angle glacoma. Three more patients had moderately elevated intraocular pressures and obviously affected children.

Linkage Analysis

Over 90 short tandem repeat polymorphisms were typed the family before linkage was detected with markers that map to the long arm of chromosome 1. Two-point maximum likelihood calculations using all available family members and 33 chromosome 1 markers revealed significant linkage to eight of them (Table 2). D1S212 was fully informative for all affected members of the family, and pairwise linkage analysis produced a lod score of 6.5 (=0). Multipoint linkage analysis did not add to the peak lod score. The glaucoma locus was therefore determined to be located in a region of about 20 centiMorgans (cM) in size between D1S191 and D1S194. Both of these markers demonstrated multiple recombinants (two and three, respectively) in affected individuals in the family. The order D1S191-glaucoma-D1S194 was more than 1,000 times more likely than the other two possible orders.

TABLE 6

Pairwise linkage data

| Recombination Fraction | | | | | | | | | |
|---|---|---|---|---|---|---|---|---|---|
| | 0.15 | 0.20 | 0.25 | 0.30 | 0.40 | $Z_{max}$ | Locus | $\hat{\theta}$ | |
| D1S212 | 6.0 | 5.4 | 4.8 | 4.2 | 3.6 | 2.9 | 1.4 | 6.5 | 0.00 | 1 |
| D1S215 | 5.1 | 4.6 | 4.0 | 3.5 | 2.9 | 2.3 | 1.0 | 5.6 | 0.00 | 1 |
| D1S218 | 4.7 | 4.3 | 3.8 | 3.3 | 2.7 | 2.2 | 1.0 | 5.2 | 0.00 | 1 |
| D1S238 | 4.4 | 4.2 | 3.9 | 3.4 | 2.9 | 2.4 | 1.2 | 4.4 | 0.04 | 1 |
| D1S117 | 3.8 | 3.6 | 3.3 | 2.8 | 2.3 | 1.8 | 0.7 | 3.8 | 0.04 | 1q |
| D1S104 | 3.2 | 2.9 | 2.6 | 2.3 | 2.0 | 1.6 | 0.7 | 3.4 | 0.00 | 1q21–q23 |
| D1S191 | 3.0 | 3.2 | 3.0 | 2.7 | 2.4 | 1.9 | 0.9 | 3.2 | 0.09 | 1 |
| D1S196 | 2.9 | 2.6 | 2.3 | 2.0 | 1.6 | 1.3 | 0.5 | 3.1 | 0.00 | 1 |

Table 6 Pairwise linkage data
Recombination fraction
0.05 0.19

5.2 Genetic Fine Mapping of the Juvenile Primary Open Angle Glaucoma Locus and Identification and Characterization of a Glaucoma Gene Once primary linkage has been identified, the next step in identifying any disease gene by positional cloning is the narrowing of the candidate locus to the smallest possible genetic region. The initial study described in Example 5.1 demonstrated that a primary open angle glacoma gene lies within an approximately 20 cM region flanked by markers D1S194 and D1S191 on chromosome 1q. Additional markers and families were obtained and used to refine the genetic locus to a 2.5 cM region using two of these families. The third family should allow the interval to be further narrowed.

In addition to the family resources, polymorphic DNA markers and genetic maps were used to refine the 1q glaucoma locus. Using STRPs, the genotype of each family member was determined. Amplification of each STRP was performed using the following protocol:

1) Dilute genomic DNA (about 1 g/l) 1/50 i.e. 20l "stock" DNA and 980 dd $H_2O$.
2) Use 2.5 l of "dilute" DNA as template for PCR
3) Prepare PCR reaction mix as follows:
   1.25l 10×Buffer (Stratagene)
   0.12l of each primer (50 pmoles each primer)
   0.5l dNTPs (5 mM C, T, & G and 0.625 mM A "cold")
   3.5l dd $H_2O$
   0.25l $^{35}$S-dATP
   0.1l Taq polymerase
   oil (one drop)
4) Perform PCR at optimal conditions for given primers (usually 94 30 s, 55 30 s and 72 30 s) and run for 35 cycles.
5) Add 5l stop solution (95% formamide, 10 mM NaOH, 0.05% bromophenol blue, 0.05% xylene cyanol) to each tube.
6) Denature samples at 95C for 3 minutes and load immediately onto a prewarmed polyacrylamide gel.
7) Dry gels on Whatmann paper and expose autoradiography film for 1–2 days.

Where possible, multiple loadings of different STRPs on gels were performed. Up to 6 markers per gel have been successfully loaded. In addition, the PCR amplification (up to three markers) have been successfully multiplexed. The juvenile glaucoma gene is believed to lie between markers AFM238 and AT3 (an 8 centimorgan interval) based on observed recombinations within the families studied. Haplotypic analysis between families has further narrowed this interval to the 2 centimorgan interval between D1S210 and AT3.

Since the genetic interval has been narrowed significantly physical mapping strategies can be used. The closest flanking markers to screen total human genomic yeast artificial chromosome (YAC) libraries to identify YACs mapping to the region of interest. The CEPH and CEPH mega-YAC libraries can be used for this purpose (available from the Centre dEtude du Polymorphisme Humain (CEPH) Paris, France). Forty-four percent of the clones in the CEPH mega-YAC library have an average size of 560 kb, an additional 21% have an average size of 800 kb, and 35% have an average size of 120 kb. This library is available in a gridded micro-titer plate format such that only 50–200 PCR reactions need to be performed using a specific sequence tagged site (STS) to identify a unique YAC containing the STS. The YAC contigs identified by CEPH have been used to begin constructing a contig across the 1q candidate region (see FIG. 3). YAC contigs using YAC ends can be constructed to identify additional YACs. YAC ends can be rescued using anchored PCR (Riley, J. et al (1990) Nucleic Acids Res 18:2887–2890), the ends can then be sequenced and the sequence can be used to develop a sequence tagged site (STS). The STS can be used to rescreen the YAC library to obtain an overlapping adjacent YAC.

Because some YACs have been shown to be chimeric or to contain deletions or rearrangements, particularly those from the mega YAC library, the correctness of each YAC contig should be verified by constructing a pulse field map of the region. In addition, chimeric YACs are minimized by ensuring that the YAC maps to a single chromosome by fluorescent in situ hybridization (FISH) or that the two YAC ends map to the same chromosome using monochromosomal somatic cell hybrids (NIGMs Panel 2). In addition, the YAC chimera problem can be minimized by not relying on any single YAC to span a given chromosome segment, but rather by obtaining at least two overlapping independent YACs to ensure coverage of a given region.

Once a YAC contig spanning the candidate region has been isolated, this reagent can be used to generate additional genetic markers for potentially finer genetic mapping. In addition, the YACs can be used to make higher resolution physical mapping reagents such as region specific lambda and cosmid clones. Lambda and cosmid clones can be used for isolation of candidate genes. A modification of "exon trapping" (Duyk, G. M. (1990) Proc Natl Acad Sci USA 87:8995–8999) known as exon amplification (Buckler, A. J. (1991) Proc Natl Acad Sci USA 88:4005–4009) can be used to identify exons from genes within the region. Exons trapped from the candidate region can be used as probes to screen eye cDNA libraries to isolate cDNAs. Where necessary, other strategies can be utilized to identify genes in genomic DNA including screening cDNA libraries with YAC fragments subcloned into cosmids, zoo blot analysis, coincidence cloning strategies such as direct selection of cDNAs with biotin-streptavidin tagged cosmid clones (Morgan, J. G. et al (1992) Nucleic Acid Res 20 (19) :5173–5179), and HTF island analysis (Bird, A. P. (1987) Trends Genet 3:342–247). Promising genes will be further evaluated by searching for mutations using GC-clamped denaturing gradient gel electrophoresis (Sheffield, V. C. et al (1989) Genomics 16:325–332), single strand conformational gel polymorphism (SSCP) analysis (Orita, M. et al (1989) Proc Natl Acad Sci USA 86:2766–2770) and direct DNA sequencing.

5.3 Primer Pairs for Use in Identifying Subjects Having a Predisposition to Glaucoma Two primer pairs that can be used in conjunction with the polymerase chain reaction to amplify a 190 base pair sequence from human genomic DNA that harbors mutations causing glaucoma (primers 1 and 2 in Table 7) have been identified.

TABLE 7

| Primer 1 | forward - ATACTGCCTAGGCCACTGGA (SEQ ID NO. 12) reverse - CAATGTCCGTGTAGCCACC (SEQ ID NO. 13) |
|---|---|
| Primer 2 | forward - GAACTCGAACAAACCTGGGA (SEQ ID NO. 14) reverse - CATGCTGCTGTACTTATAGCGG (SEQ ID NO. 15) |

These primers were used to screen 410 patients with glaucoma and 81 normal individuals. Four amino acid altering sequence changes were detected in a total of 12 glaucoma patients (2.9%). No amino acid altering sequence changes were observed in the normal individuals.

The prevalence of mutations in the segment of DNA amplified by these primer pairs suggest that use of these primers in conjunction with an appropriate detection method can be used to identify a predisposition to glaucoma in approximately 100 thousand patients in the United States alone.

5.4 Additional Primer Pairs and Their Use in Identifying Subjects Having a Predisposition to Glaucoma The study was approved by the Human Subjects Review Committee at the University of Iowa and informed consent was obtained from all study participants. Primary open angle glacoma was defined as the presence of an intraocular pressure over 21 mm Hg as well as evidence of glaucomatous optic nerve head damage. Visible optic nerve head damage alone was accepted if there was documented enlargement of the optic nerve head cup. Otherwise, both a large optic nerve head cup with a thin neural rim and characteristic optic nerve related visual field loss were required. Patients were excluded if they had a history of eye surgery prior to the diagnosis of glaucoma or evidence of secondary glaucoma, such as exfoliation or pigment dispersion. Normal volunteers were over 40 years of age, had intraocular pressures under 20 mm Hg, and had no family or personal history of glaucoma. 716 unrelated patients affected with primary open angle glaucoma (POAG) and 91 volunteers were screened for mutations in the coding sequence of the GLC1A gene. This was accomplished with an electrophoretic procedure known as single strand conformation polymorphism analysis (SSCP). The sequences of the oligonucleotide primers used for the GLC1A assay are presented in Table 8.

TABLE 8

Primer Pairs

| Exon | Forward Primer | Reverse Primer |
|---|---|---|
| 1 | SEQ ID No. 16 | SEQ ID No. 17 |
| 1 | SEQ ID No. 18 | SEQ ID No. 19 |
| 1 | SEQ ID No. 20 | SEQ ID No. 21 |
| 1 | SEQ ID No. 22 | SEQ ID No. 23 |
| 1 | SEQ ID No. 24 | SEQ ID No. 25 |
| 1 | SEQ ID No. 26 | SEQ ID No. 27 |
| 2 | SEQ ID No. 28 | SEQ ID No. 29 |
| 3 | SEQ ID No. 30 | SEQ ID No. 31 |
| 3 | SEQ ID No. 32 | SEQ ID No. 33 |
| 3 | SEQ ID No. 34 | SEQ ID No. 35 |
| 3 | SEQ ID No. 36 | SEQ ID No. 37 |
| 3 | SEQ ID No. 38 | SEQ ID No. 39 |
| 3 | SEQ ID No. 40 | SEQ ID No. 41 |

Mutations were confirmed with automated DNA sequencing. 227 of the patients (32%) were ascertained because of a positive family history of glaucoma while 402 (56%) were ascertained consecutively in a single glaucoma clinic (the University of Iowa). Overall, 563 of the patients were ascertained in Iowa, 97 in Australia and the remainder from elsewhere in the United States. All of the normal volunteers were collected in Iowa. More than 75% of the patients in each group were Caucasian. A portion of the GLC1A gene had been previously evaluated for mutations in 330 of these same glaucoma patients and all 91 normal volunteers (see above). However, in this study, the entire coding region was evaluated. An additional 505 unrelated control individuals with an unknown glaucoma status were also evaluated for sequence changes. Three hundred and eighty of these control patients had been previously screened for mutations in a portion exon 3. 184 of these general population controls were commected in Iowa 13 in Australia. Family members of the probands found to harbor GLC1A sequence changes were also evaluated for mutations. Efforts were made to examine or review the medical records of all molecularly affected family members. The age of onset and the highest recorded intraocular pressures were associated with six different mutations were evaluated with a Kruskal-Wallis non-parametric analysis of variance. All p values were two-tailed. In the four largest families, co-segregation of a GLC1A mutation and the disease phenotype was evaluated with the LOD score method as described above 5.5 Cloning and Sequencing Human and Mouse GLC1A and Northern Blot Analysis of Expression BAC screening. BAC clones containing the human GLCIA gene were identified by screening human BAC library pools (Research Genetics, Huntsville, Ala.) with a PCR-based assay. One microliter of BAC pool DNA was used as template in an 8.35 $\mu$l PCR reaction containing 1.25 $\mu$l of 10×buffer (100 mM tris-HCl, pH 8.3, 500 mM Kcl, 15 mM $MgCl_2$); deoxynucleotides dCTP, dATP, dTTP, and DGTP (300 $\mu$M each); 1 pmol of each primer; and 0.25 units of Taq polymerase (Boehringer Mannheim, Indianapolis, Ind.). The primers used in the screening assay were specific for exon three of GLC1A (FWD: 5' ATACTGCCTAGGC-CACTGGA 3' (SEQ ID No. 34) and REV: 5' CAATGTC-CGTGTAGCCACC 3' (SEQ ID No. 35)). Samples were denatured at 94° C. for 5 minutes and incubated for 35 cycles at 94° C. 30s, 55° C. 30s, 72° C. 30s thermocycler (Omnigene, Teddington, Middlesex, UK). After amplification, 5 $\mu$l of stop solution (95% formamide, 10 mM NaOH, 0.5% bromophenyl blue, 0.05% xylene cyanol) were added. Amplification products were electrophoresed on 6% polyacrylamide-5% glycerol gels at 50 W for approximately 2 hours. After electrophoresis, gels were stained with silver nitrate (Bassam 1991). A BAC containing the mouse GLCIA orthologue was identified by screening the mouse 129 BAC library pools (Research Genetics, Huntsville Ala.). Primers specific for exon three of the human GLCIA gene (FWD: 5' TGGCTACCACGGACAGTTC 3' (SEQ ID No. 36) and REV: 5' CATTGGCCACTGACTGCTTA 3' (SEQ ID No. 37) were used for a primary PCR-based screen as described above. The primary screen identified sub-pools of BACs which contained the mouse GLCIA gene. Filters blotted with the BACs in the subpools (Research Genetics, Huntsville, Ala.) were screened by hybridization with a digoxigenin probe using the Genius System hybridization kit (Boehringer Mannheim, Indianapolis, Ind.). Digoxigenin labeled probe for hybridization was generated by PCR amplifying 50 ng of mouse 129 DNA in a 25 $\mu$l reaction containing 3.75 $\mu$l of 10×buffer; 1.5 $\mu$l of labeling dNTP mixture (1 mM dATP, 1 mM dCTP, 1 mM dGTP 0.65 mM dTTP, and 0.35 mM of digoxigenin conjugated dUTP); 7.6 pmoles each of FWD and REV primer; and 1.25 units of Taq polymerase (Boehringer Mannheim, Indianapolis, Ind.). PCR reaction conditions were as described above. Hybridization conditions were as recommended by the manufacturer.

The human GLCIA cDNA sequence was used to select PCR primers that produced an amplification product of identical size when using both human and mouse genomic DNA as template. The amplification products were sequenced to confirm that they were from the human GLCIA gene and the mouse orthologue of this gene. The PCR primers were then used to screen both a human and mouse BAC library. Both human and mouse BACs containing the GLCIA gene were identified, subcloned into plasmids, and several clones covering each GLCIA gene were identified. These subclones were used to generate both human and mouse genomic GLCIA sequence.

Subcloning. The mouse and human BACs containing the GLCIA gene were digested with either EcoR 1, Aval, Accl, or BamHI and ligated into either pT7-blue (Novagen, Milwaukee, Wis.) or pUC19.

Sequencing. PCR products and BAC subclones were sequenced with fluorescent dideoxynucleotides on an Applied Biosystems (ABI) model 373 or 377 automated sequencer.

GLCIA CA repeat polymorphisms. The CA repeat polymorphism upstream of the GLCIA gene was PCR amplified with primers 5'-TTCCTTCAGGTTGGGAGATG-3' (SEQ ID No. 42) and 5'-GAGAGCACCAGGAGATGGAG-3' (SEQ ID No. 43). The PCR reaction conditions were as described in the BAC screening section. Allele frequencies for the upstream polymorphism are: Allele 1, 1.1%; Allele 2, 2.2%; Allele 3, 48.9%; Allele 4, 1.1%; Allele 5, 21.1%; Allele 6, 25.6%. Allele frequencies for the downstream polymorphism are: Allele 1, 25.3%; Allele 2, 13%, Allele 3, 60.3%, Allele 4, 1.4%.

Sequence comparison. DNA sequences were aligned and contigs were formed using the Sequencher DNA analysis package (DNA Codes, Ann Arbor, Mich.). Putative enhancer and promoter elements were identified using the internet resource TESS (http://agave.humgen.upenn.edu/utess/) and the transcription factor binding site data set TRANSFAC v3.2. The predicted protein sequence was analyzed with PROSITE, Tmpred, NetOgly, and SignalP software packages available on the internet at http://expasy.hcuge.chsprot/prosite.html; http://ulrec3.unil.ch/software/TMPED_form.html; http://genome.cbs.dtu.dk/services/netOGLYC/; http://www.cbs.dtu.dk/services/SignalP/. Data base searches for expression of the GLCIA gene used the program BLAST and the data bases dbest and NR available on the internet at http://www.ncbi.nlm.nih.gov/cgi-bin/BLAST/nph-blast?Jform=0.

Northern blot analysis. Human Multiple Tissue Northern (MTN) blots (Clontech, San Francisco, Calif.) were probed either with the entire human GLCIA cDNA sequence or with a section of exon three of the human GLCIA gene corresponding to codon 315 to the termination site. The probes were labeled with $^{32}$P-(dCTP) using Ready-To-Go DNA Labeling Beads (-dCTP) (Pharmacia Biotech, Piscataway, N. J.). Hybridization was for 16 hours at 42° C. in 50% formamide, 5×standard saline citrate (5×SSC: 0.75M sodium chloride, 0.075M sodium acetate), 1×Denhardt's solution, 20 mM phosphate buffer (pH 7.5), 1% sodium dodecyl sulfate (SDS), 100 µg/ml salmon sperm DNA, and 10% dextran sulfate. Following hybridization, blots were washed twice at room temperature in 1×SSC, rinsed twice in 1×SSC/1% SDS at 65° C., and washed once in 0.1×SSC, 0.1% SDS to confirm the specificity of the hybridization. Autoradiography was performed with Kodak XAR-5 film at −70° C. with DuPont Cronex Lightning Plus intensifying screens (DuPont, Wilmington, Del.).

What is claimed is:

1. An isolated polynucleotide consisting of a nucleic acid molecule or the complement of a nucleic acid molecule set forth in any of SEQ ID Nos. 18, 19, 20, 21, 22, 23, 27, 28, 29, 30, 32, 33, 36, 37, 40, 41, 42 or 43.

2. An isolated polynucleotide consisting of a nucleic acid molecule or the complement of a nucleic acid molecule obtained by amplifying a GLC1A gene with a primer pair selected from the group consisting of SEQ ID Nos 16 and 17, SEQ ID Nos 18 and 19, SEQ ID Nos 20 and 21, SEQ ID Nos 22 and 23, SEQ ID Nos 26 and 27, SEQ ID Nos 28 and 29, SEQ ID Nos 30 and 31, SEQ ID Nos 32 and 33, SEQ ID Nos 36 and 37, SEQ ID Nos 40 and 41, SEQ ID Nos 42 and 43.

3. An isolated polynucleotide of claim 2 from Exon 1 of FIG. 1A or the complement of a nucleic acid molecule from Exon 1.

4. An isolated polynucleotide of claim 2 from Exon 2 of FIG. 1B or the complement of a nucleic acid molecule from Exon 2.

5. An isolated polynucleotide of claim 2 from Exon 3 of FIG. 1C or the complement of a nucleic acid molecule from Exon 3.

6. An isolated polynucleotide of claim 3, wherein the primer pair is selected from the group consisting of: SEQ ID Nos. 16 and 17; SEQ ID Nos. 18 and 19; SEQ ID Nos. 20 and 21; SEQ ID Nos. 22 and 23; and SEQ ID Nos. 26 and 27.

7. An isolated polynucleotide of claim 4, wherein the primer pair is comprised of SEQ ID Nos. 28 and 29.

8. An isolated polynucleotide of claim 5, wherein the primer pair is comprised of SEQ ID Nos 30 and 31, SEQ ID Nos 32 and 33, SEQ ID Nos 36 and 37, SEQ ID Nos 40 and 41.

9. An isolated polynucleotide of claim 2, which is upstream of the GLC1A gene and is amplified by SEQ ID Nos 42 and 43.

10. A method for determining whether a subject has or has the potential for developing primary open angle glacoma, comprising the steps of:
a) obtaining a biological sample containing genomic DNA, or mRNA or a complement thereof from a subject;
b) performing an amplification on the genomic DNA, or mRNA or complement thereof using a primer pair selected from the group consisting of SEQ ID Nos 16 and 17, SEQ ID Nos 18 and 19, SEQ ID Nos 20 and 21, SEQ ID Nos 22 and 23, SEQ ID Nos 26 and 27, SEQ ID Nos 28 and 29, SEQ ID Nos 30 and 31, SEQ ID Nos 32 and 33, SEQ ID Nos 36 and 37, SEQ ID Nos 40 and 41, SEQ ID Nos 42 and 43, thereby obtaining an amplification product; and
c) analyzing the amplification product for the presence of a mutation, wherein the presence of a mutation indicates that the subject has or has the potential for developing primary open angle glacoma.

11. A screening method of claim 10, wherein in step c), the amplification product is analyzed using single strand conformation polymorphism (SSCP) analysis.

12. A screening method of claim 10, wherein in step c), the amplification product is analyzed by sequencing.

13. A kit for diagnosing a subject as having primary open angle glacoma comprising:
a) a primer pair selected from the group consisting of: SEQ ID Nos 16 and 17, SEQ ID Nos 18 and 19, SEQ ID Nos 20 and 21, SEQ ID Nos 22 and 23, SEQ ID Nos 26 and 27, SEQ ID Nos 28 and 29, SEQ ID Nos 30 and 31, SEQ ID Nos 32 and 33, SEQ ID Nos 36 and 37, SEQ ID Nos 40 and 41, SEQ ID Nos 42 and 43; and
b) instructions for using the primer pair to perform an amplification.

* * * * *

UNITED STATES PATENT AND TRADEMARK OFFICE
CERTIFICATE OF CORRECTION

PATENT NO.     : 6,403,307 B1
DATED          : June 11, 2002
INVENTOR(S)    : Stone et al.

It is certified that error appears in the above-identified patent and that said Letters Patent is hereby corrected as shown below:

<u>Column 108,</u>
Lines 2, 19 and 26, please delete "glacoma" and substitute therefor -- glaucoma --

Signed and Sealed this

Twentieth Day of August, 2002

*Attest:*

*Attesting Officer*

JAMES E. ROGAN
*Director of the United States Patent and Trademark Office*